(12) United States Patent
Kriesel et al.

(10) Patent No.: US 7,169,128 B2
(45) Date of Patent: Jan. 30, 2007

(54) MULTICHANNEL FLUID DELIVERY DEVICE

(75) Inventors: Marshall S. Kriesel, St. Paul, MN (US); Alan Langerud, Plymouth, MN (US)

(73) Assignee: BioQuiddity, Inc., San Francisco, CA (US)

( * ) Notice: Subject to any disclaimer, the term of this patent is extended or adjusted under 35 U.S.C. 154(b) by 730 days.

(21) Appl. No.: 10/634,487

(22) Filed: Aug. 4, 2003

(65) Prior Publication Data

US 2005/0038387 A1 Feb. 17, 2005

(51) Int. Cl.
*A61M 37/00* (2006.01)

(52) U.S. Cl. .................. 604/133; 604/890.1; 604/151; 604/246

(58) Field of Classification Search ........ 604/131–134, 604/151–153, 244, 246, 247, 248, 139, 890.1, 604/181, 183
See application file for complete search history.

(56) References Cited

U.S. PATENT DOCUMENTS

| | | | |
|---|---|---|---|
| 3,731,681 A | 5/1973 | Blackshear et al. | |
| 4,381,006 A | 4/1983 | Genese | |
| 4,557,728 A | 12/1985 | Sealfon et al. | |
| 4,608,042 A | 8/1986 | Vanderveen et al. | |
| 4,681,566 A | 7/1987 | Fenton, Jr. et al. | |
| 4,755,172 A | 7/1988 | Baldwin | |
| 4,772,263 A | 9/1988 | Dorman et al. | |
| 4,850,807 A | 7/1989 | Frantz | |
| 4,863,429 A | 9/1989 | Baldwin | |
| 5,014,750 A | 5/1991 | Winchell et al. | |
| 5,098,377 A | 3/1992 | Borsanyi et al. | |
| 5,100,389 A | 3/1992 | Vaillancourt | |
| 5,176,641 A | 1/1993 | Idriss | |
| 5,205,820 A * | 4/1993 | Kriesel | 604/85 |
| 5,236,418 A | 8/1993 | Kriesel | |
| 5,290,259 A | 3/1994 | Fischer | |
| 5,306,257 A | 4/1994 | Zdeb | |
| 5,314,405 A | 5/1994 | Kriesel et al. | |
| 5,336,188 A * | 8/1994 | Kriesel | 604/132 |
| 5,346,476 A | 9/1994 | Elson | |
| 5,380,287 A | 1/1995 | Kikuchi et al. | |
| 5,411,480 A | 5/1995 | Kriesel | |
| 5,419,771 A | 5/1995 | Kriesel | |
| 5,484,410 A | 1/1996 | Kriesel et al. | |
| 5,499,968 A | 3/1996 | Milijasevic et al. | |
| 5,514,090 A | 5/1996 | Kriesel et al. | |
| 5,545,139 A | 8/1996 | Kriesel | |
| 5,620,420 A | 4/1997 | Kriesel | |
| 5,693,018 A | 12/1997 | Kriesel et al. | |
| 5,720,729 A | 2/1998 | Kriesel | |
| 5,721,382 A | 2/1998 | Kriesel et al. | |
| 5,735,818 A | 4/1998 | Kriesel et al. | |
| 5,741,242 A | 4/1998 | Kriesel | |

(Continued)

*Primary Examiner*—Nicholas Lucchesi
*Assistant Examiner*—Theodore J. Stigell
(74) *Attorney, Agent, or Firm*—James E. Brunton, Esq.

(57) ABSTRACT

A compact fluid dispenser for use in controllably dispensing fluid medicaments, such as antibiotics, oncolytics, hormones, steroids, blood clotting agents, analgesics, and like medicinal agents from a plurality of prefilled containers at a uniform rate. The dispenser uniquely includes a plurality of stored energy source that are provided in the form of compressible-expandable members of novel construction that provide the force necessary to continuously and uniformly expel fluid from a plurality of device reservoirs. The apparatus further includes a plurality of fluid flow control assemblies that precisely control the flow of the medicament solutions from the plurality of device reservoirs to the patient.

37 Claims, 42 Drawing Sheets

U.S. PATENT DOCUMENTS

| | | | |
|---|---|---|---|
| 5,743,879 A * | 4/1998 | Kriesel | 604/132 |
| 5,766,149 A | 6/1998 | Kriesel et al. | |
| 5,779,676 A | 7/1998 | Kriesel et al. | |
| 5,807,323 A | 9/1998 | Kriesel et al. | |
| 5,836,484 A | 11/1998 | Gerber | |
| 5,858,005 A | 1/1999 | Kriesel | |
| 5,885,250 A | 3/1999 | Kriesel et al. | |
| 5,897,530 A | 4/1999 | Jackson | |
| 5,921,962 A | 7/1999 | Kriesel et al. | |
| 5,925,017 A | 7/1999 | Kriesel et al. | |
| 5,957,891 A | 9/1999 | Kriesel et al. | |
| 5,993,425 A | 11/1999 | Kriesel | |
| 6,010,482 A | 1/2000 | Kriesel et al. | |
| 6,027,472 A | 2/2000 | Kriesel et al. | |
| 6,030,363 A | 2/2000 | Kriesel | |
| 6,045,533 A | 4/2000 | Kriesel et al. | |
| 6,063,059 A | 5/2000 | Kriesel | |
| 6,068,613 A | 5/2000 | Kriesel et al. | |
| 6,068,614 A | 5/2000 | Kimber et al. | |
| 6,086,561 A | 7/2000 | Kriesel et al. | |
| 6,090,071 A | 7/2000 | Kriesel | |
| 6,095,491 A | 8/2000 | Kriesel | |
| 6,126,637 A | 10/2000 | Kriesel et al. | |
| 6,126,642 A | 10/2000 | Kriesel et al. | |
| 6,152,898 A | 11/2000 | Olsen | |
| 6,159,180 A | 12/2000 | Kriesel et al. | |
| 6,176,845 B1 | 1/2001 | Kriesel et al. | |
| 6,183,441 B1 | 2/2001 | Kriesel et al. | |
| 6,190,359 B1 | 2/2001 | Heruth | |
| 6,210,368 B1 | 4/2001 | Rogers | |
| 6,236,624 B1 | 5/2001 | Kriesel et al. | |
| 6,245,041 B1 | 6/2001 | Kriesel | |
| 6,258,062 B1 | 7/2001 | Thielen et al. | |
| 6,270,481 B1 | 8/2001 | Mason et al. | |
| 6,273,133 B1 | 8/2001 | Williamson et al. | |
| 6,277,095 B1 | 8/2001 | Kriesel et al. | |
| 6,293,159 B1 | 9/2001 | Kriesel et al. | |
| 6,319,235 B1 | 11/2001 | Yoshino | |
| 6,355,019 B1 | 3/2002 | Kriesel et al. | |
| 6,391,006 B1 | 5/2002 | Kriesel et al. | |
| 6,394,980 B2 | 5/2002 | Kriesell et al. | |
| 6,398,760 B1 | 6/2002 | Danby | |
| 6,485,461 B1 | 11/2002 | Mason et al. | |
| 6,537,249 B2 | 3/2003 | Kriesell et al. | |
| 6,542,350 B1 | 4/2003 | Rogers | |
| 6,569,125 B2 | 5/2003 | Jepson et al. | |
| 6,645,175 B2 | 11/2003 | Kriesel et al. | |
| 6,669,668 B1 | 12/2003 | Kleeman et al. | |

* cited by examiner

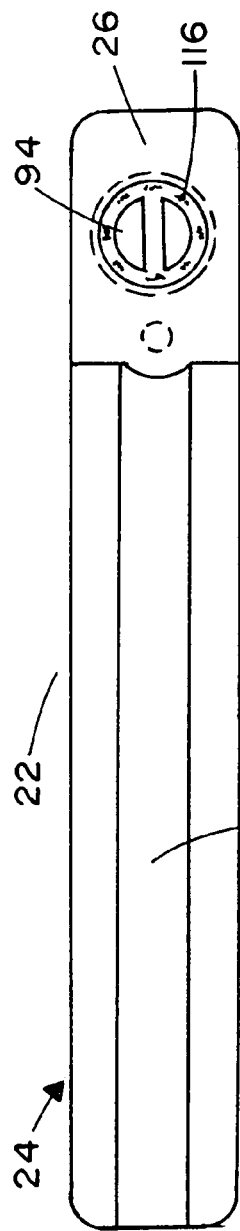
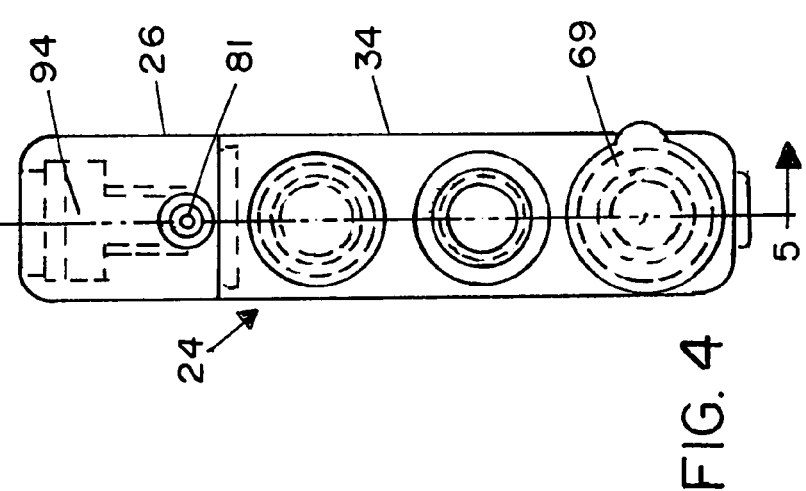
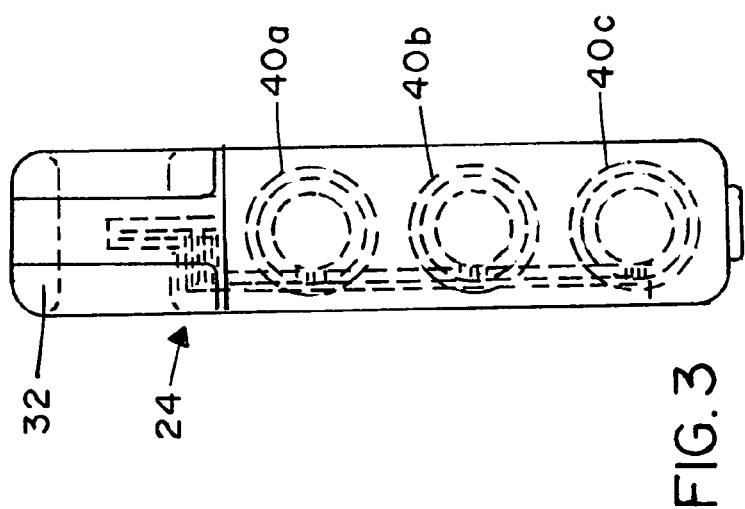
FIG. 2
FIG. 4
FIG. 3

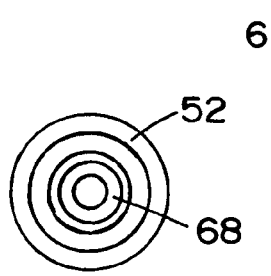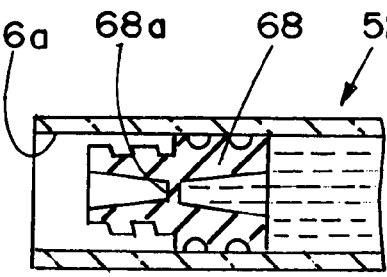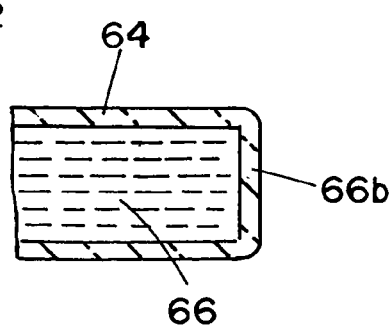
FIG.14　　FIG.15
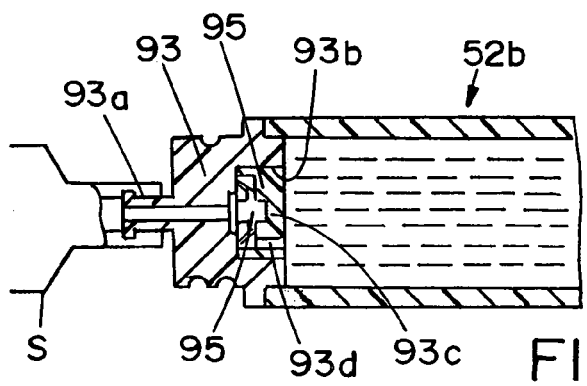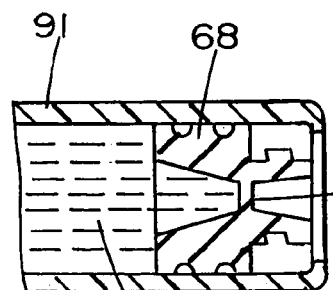
FIG.15A
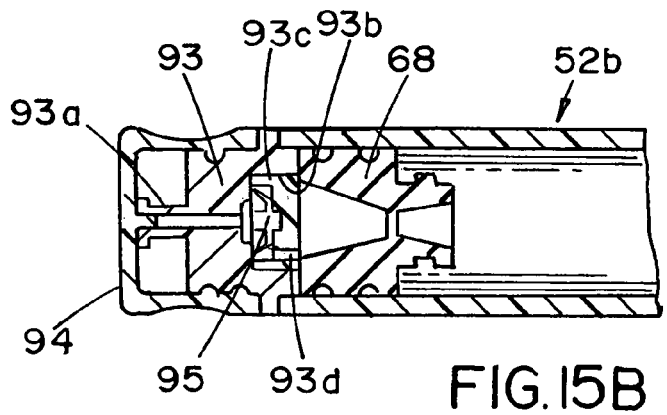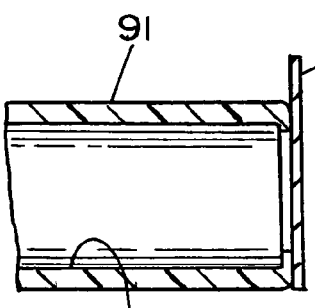
FIG.15B

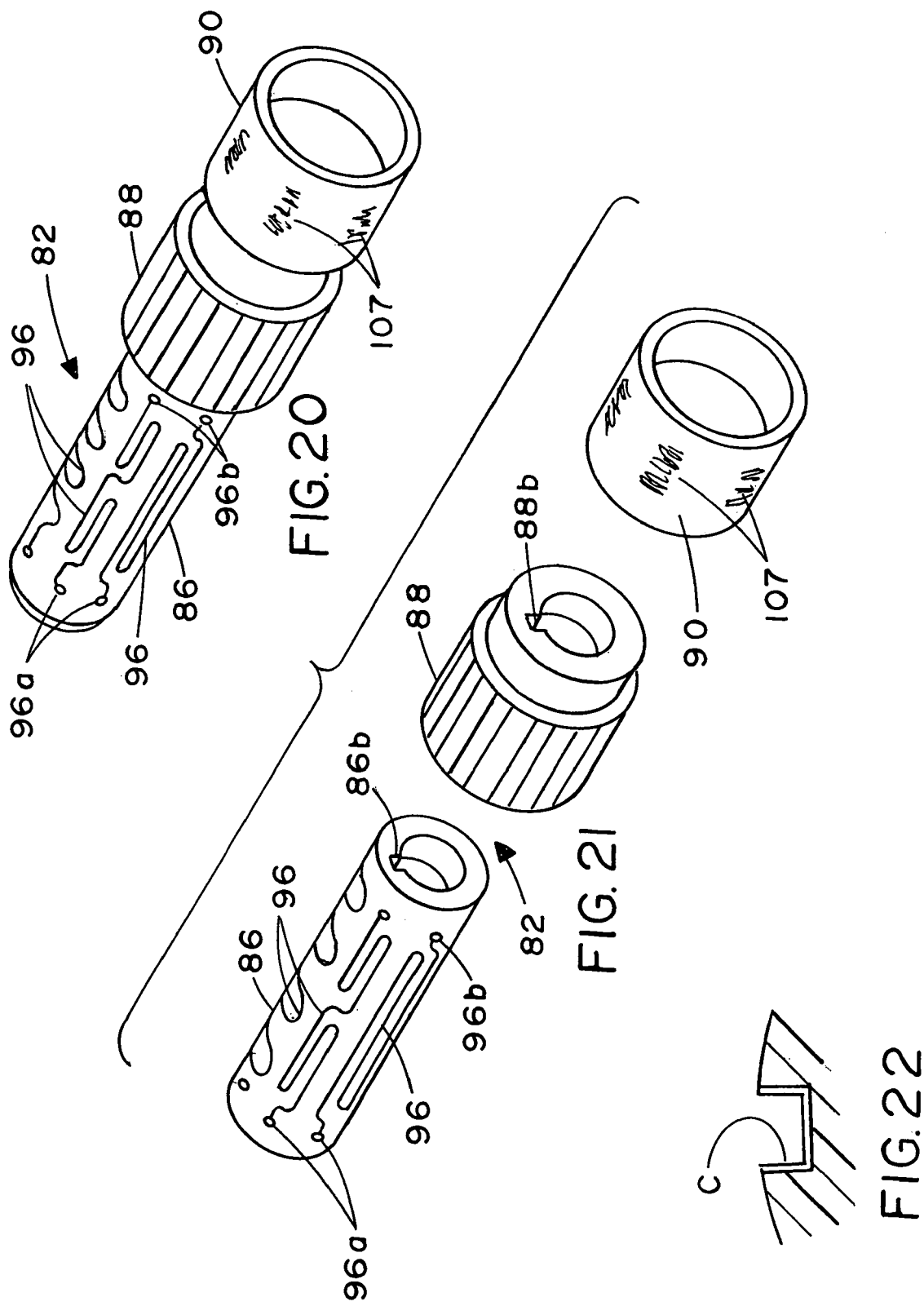

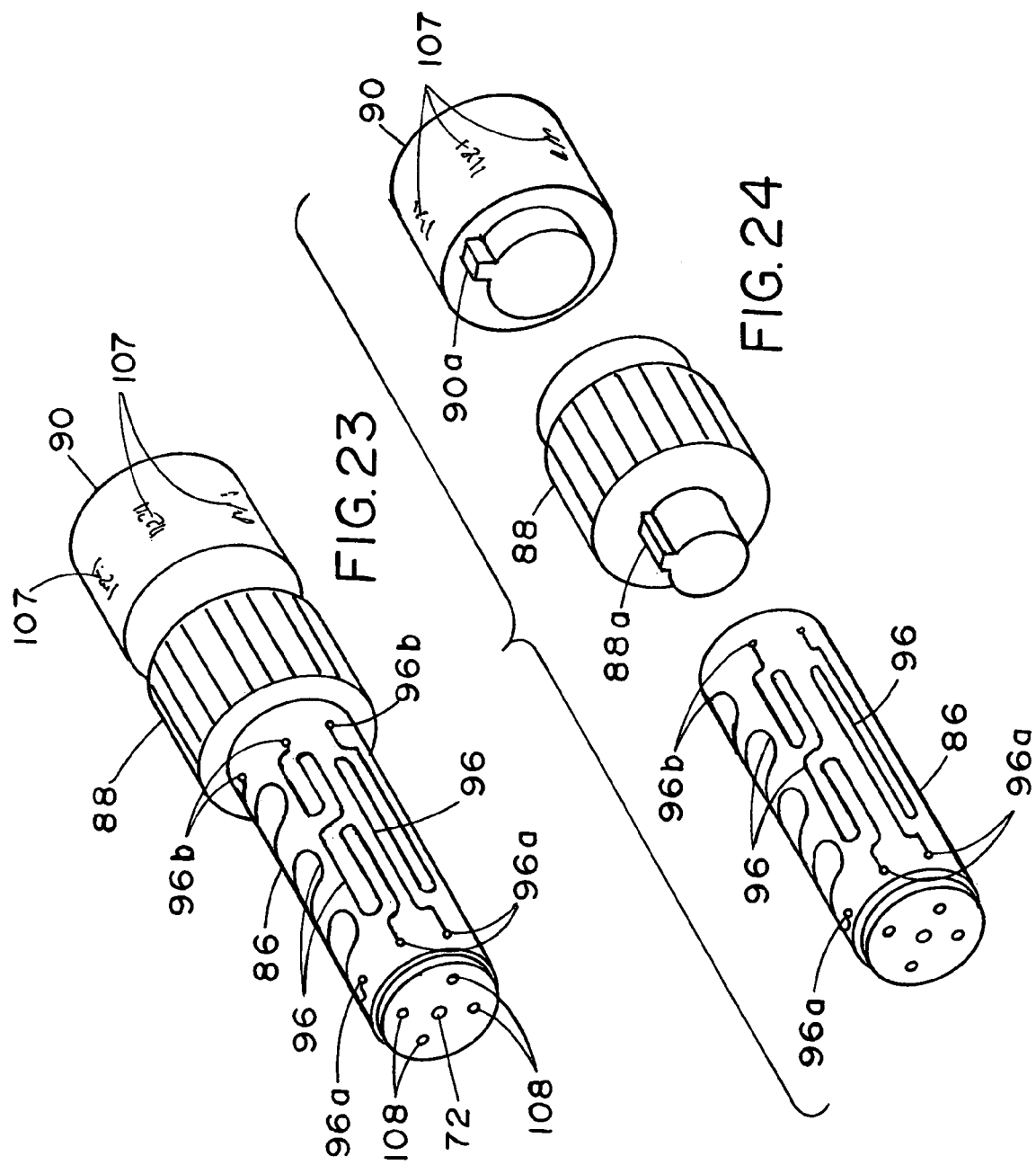

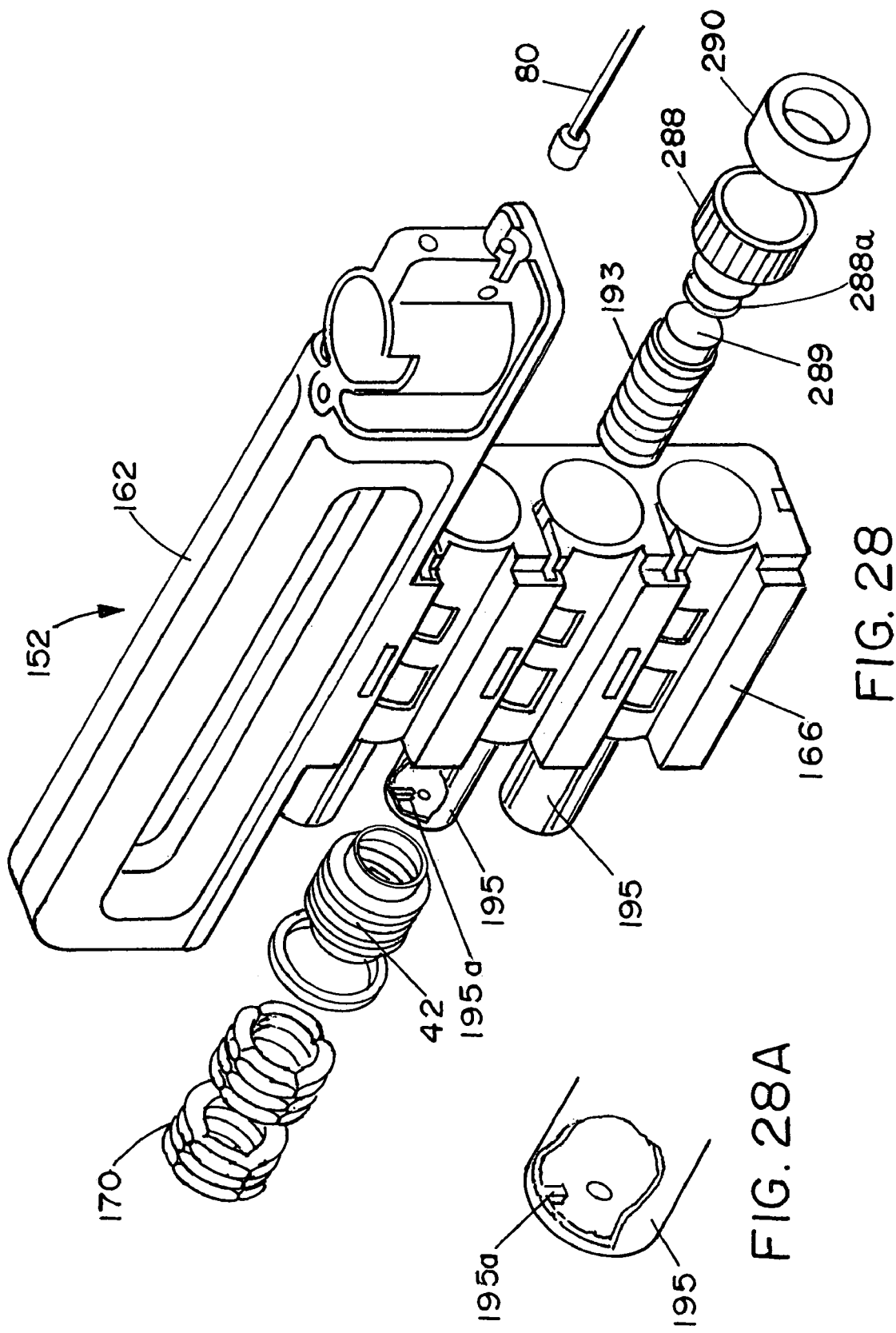

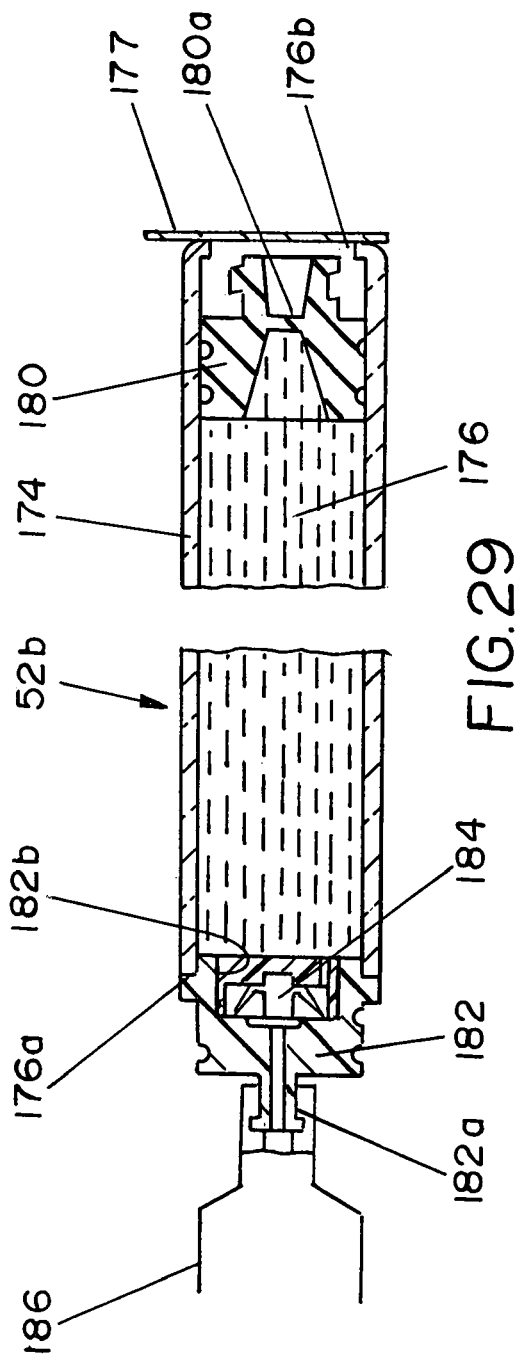
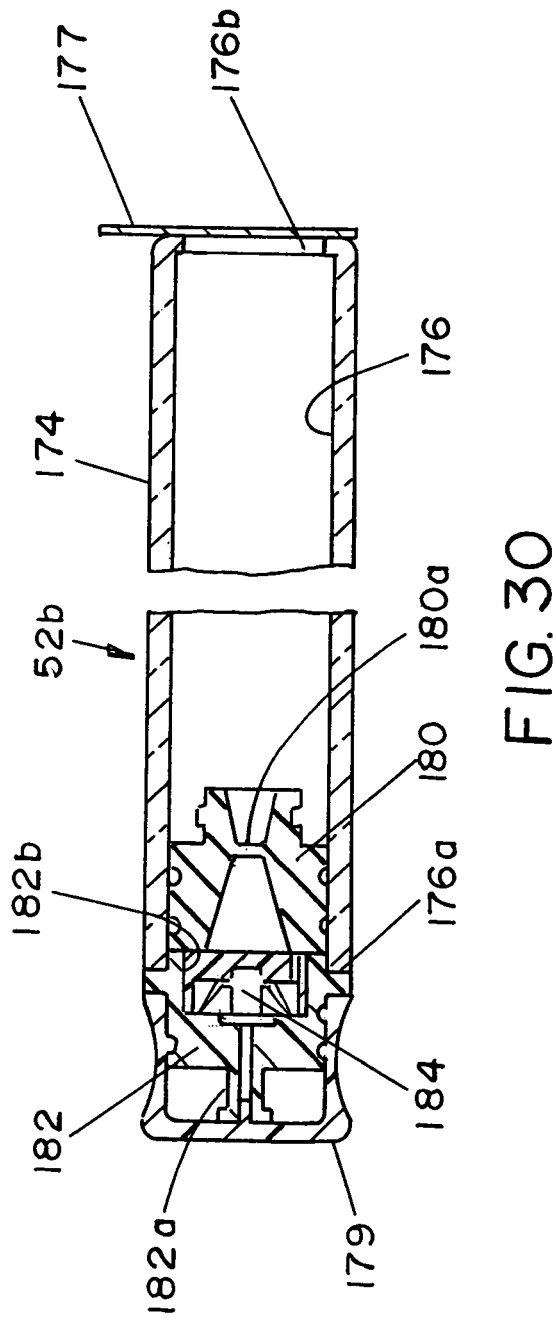
FIG. 29
FIG. 30

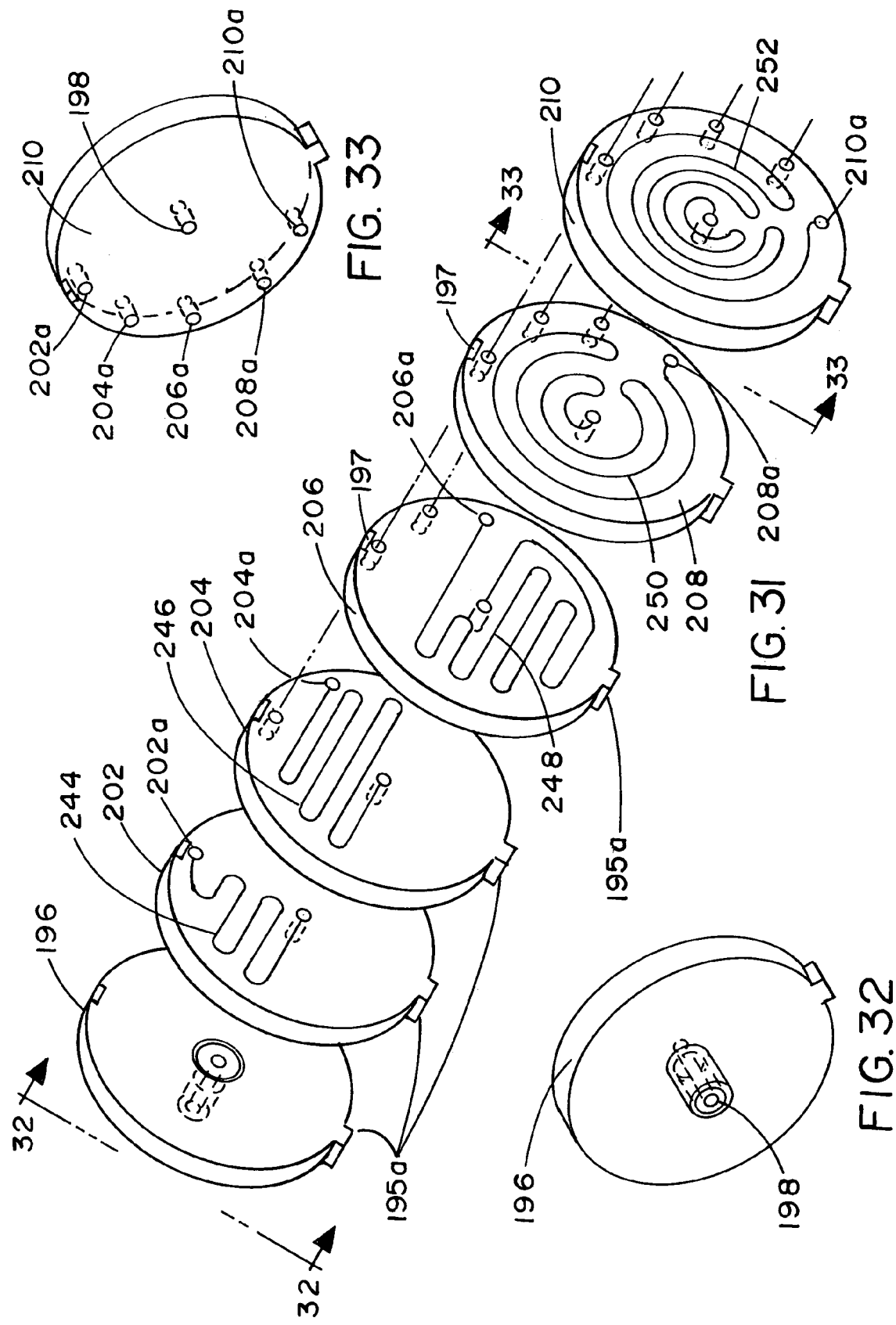

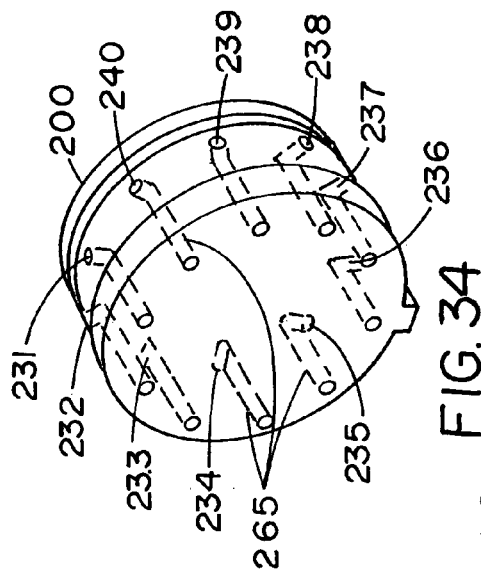
FIG. 34
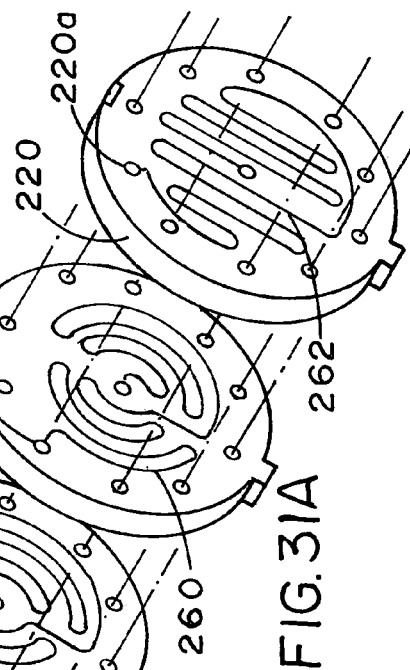
FIG. 31A
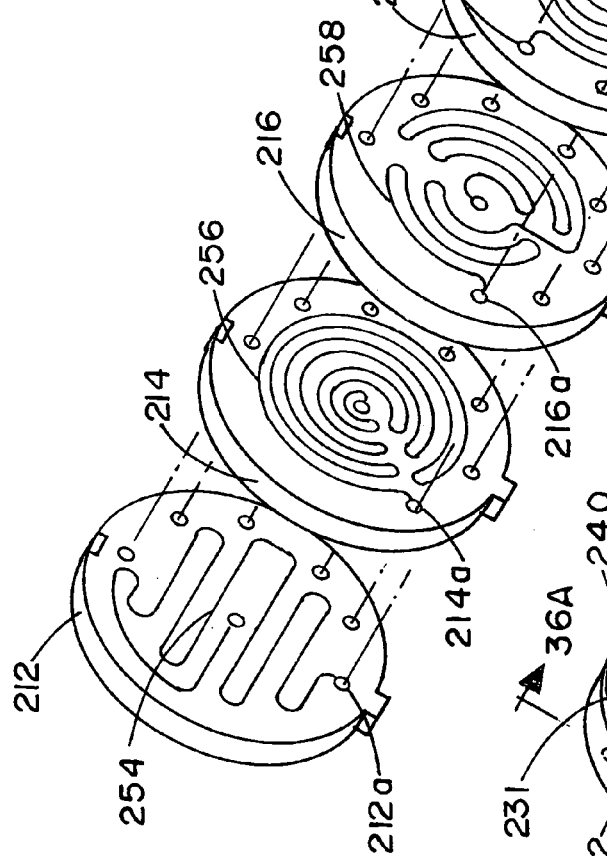
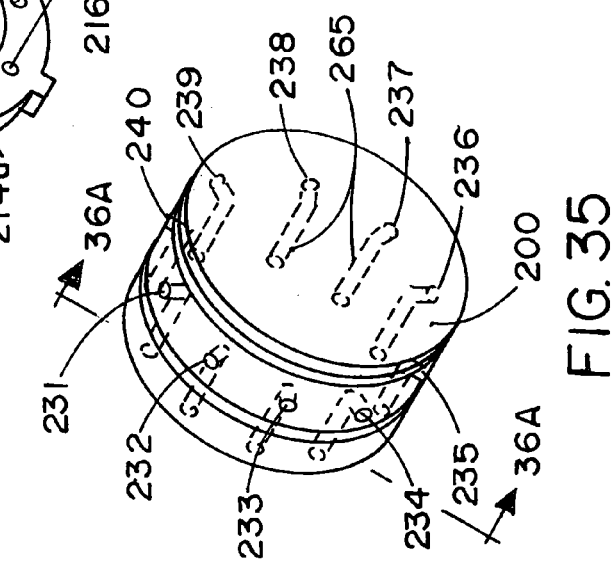
FIG. 35

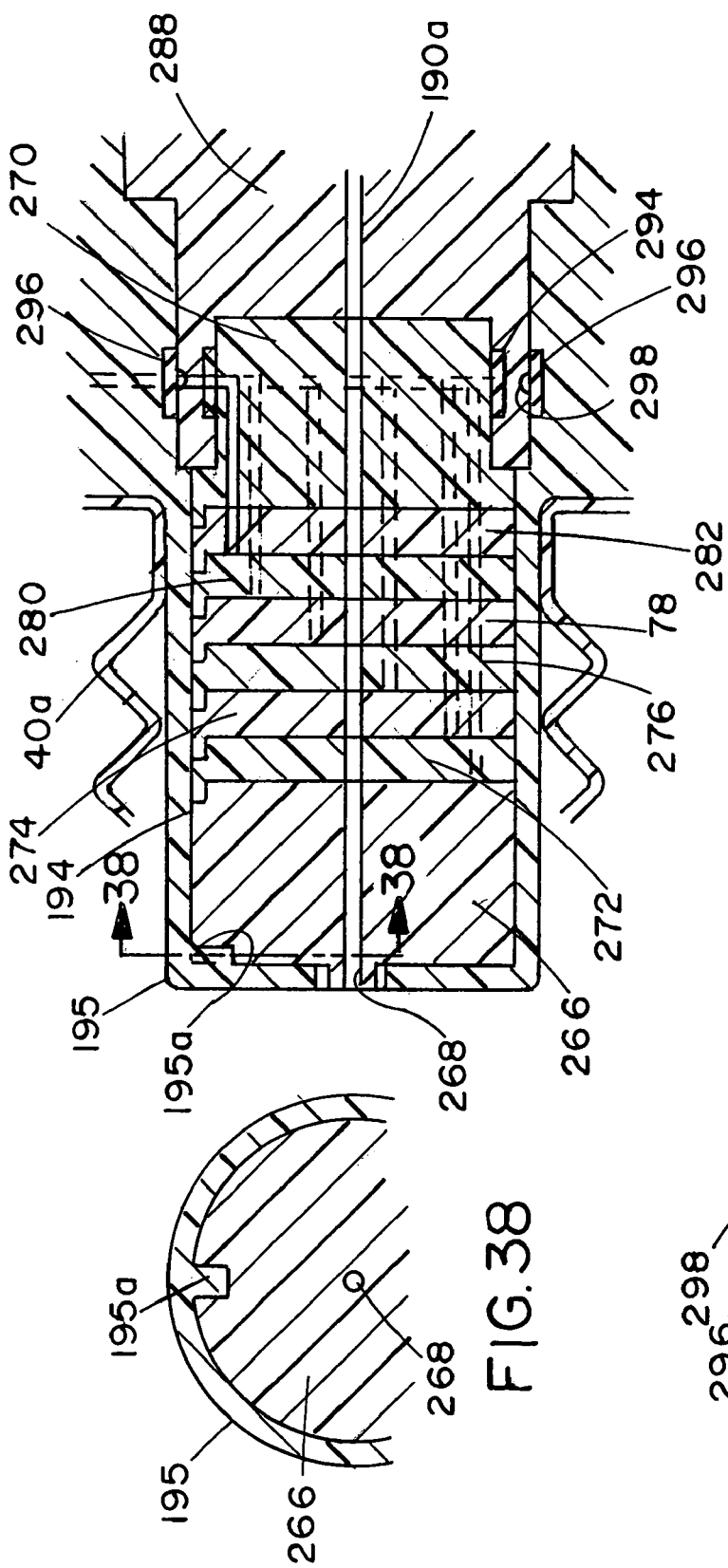
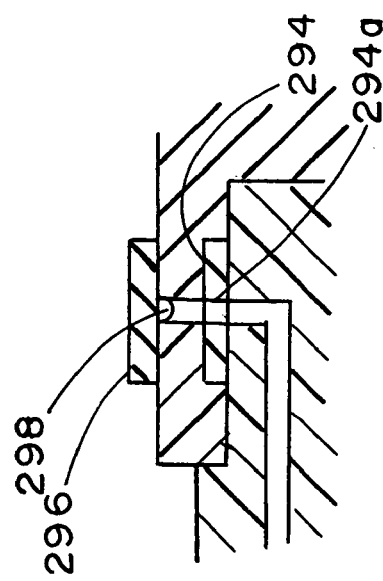
FIG. 37
FIG. 37A
FIG. 38

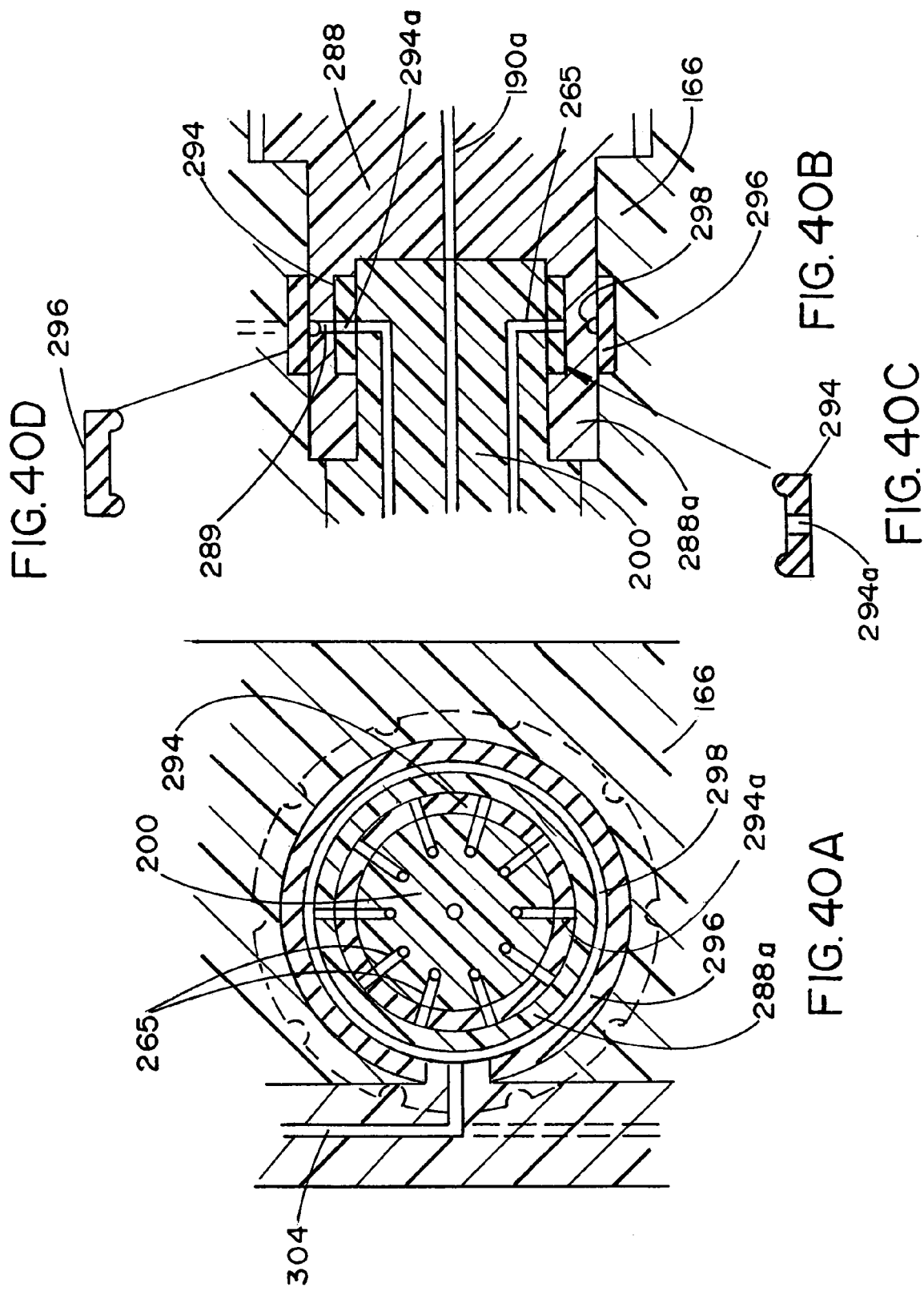

| CONFIG. | | |
|---|---|---|
| F CONFIG. | (multiwave stack) | (ring) MULTIWAVE COMP. SPRING |
| G CONFIG. | (belleville stack) | (washer) BELLEVILLE SPRING WASHER |
| H CONFIG. | (belleville stacked) | (washer) BELLEVILLE WASHER (STACKED) |
| I CONFIG. | (disc-spring stack) | (toothed disc) DISC-SPRING (INT. TOOTH) |
| J CONFIG. | (disc-spring stacked) | (toothed disc) DISC-SPRING (INT. TOOTH) STACKED |

FIG. 41B (A) DISC SPRING STACK CONSISTING OF DISC SPRINGS OF DIFFERENT THIKNESSES.

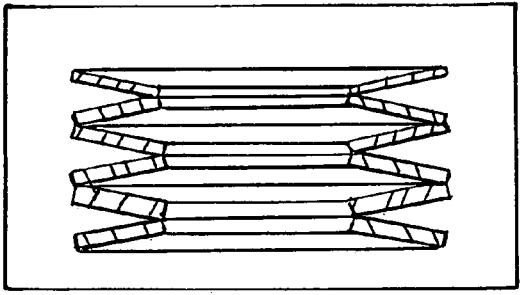

(D) GUIDING BY CYLINDRICAL "SHOULDERS" AT THE INSIDE & OUTSIDE DIA'S.

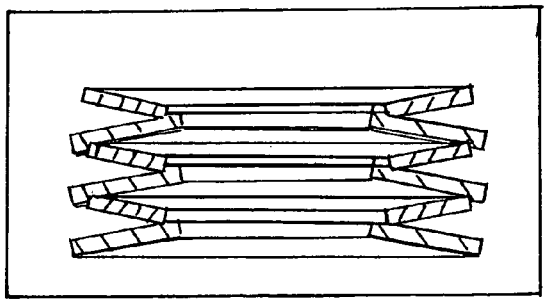

(B) DISC SPRING STACKS OF PARALLEL COMPONENTS OF DIFFERENT NUMBERS OF DISC SPRINGS ARRANGED IN SERIES.

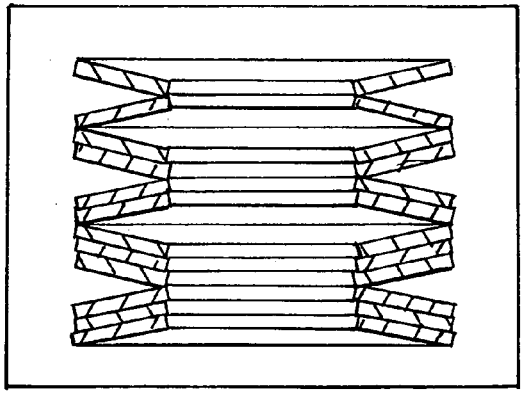

(E) GUIDING BY MEANS OF INTERMEDIATE RINGS.

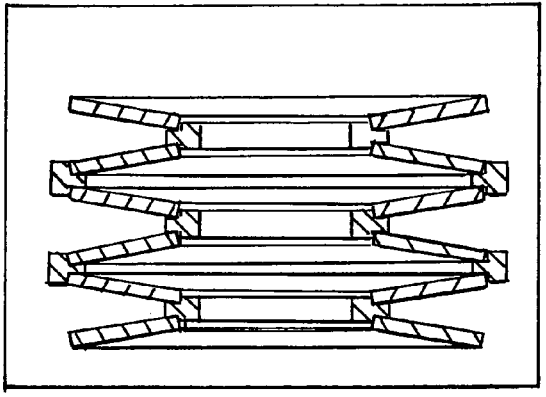

(C) DISC SPRING STACKS WITH DEFLECTION LIMITING RINGS OF DIFFERENT THICKNESSES

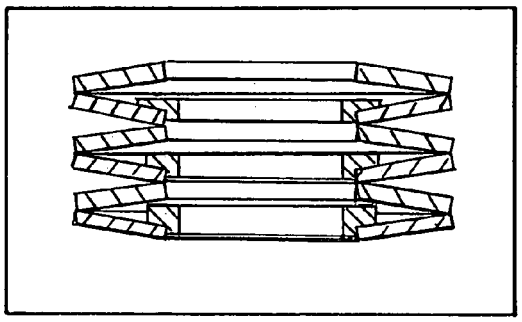

(F) GUIDING BY BALLS OR WIRE RINGS.

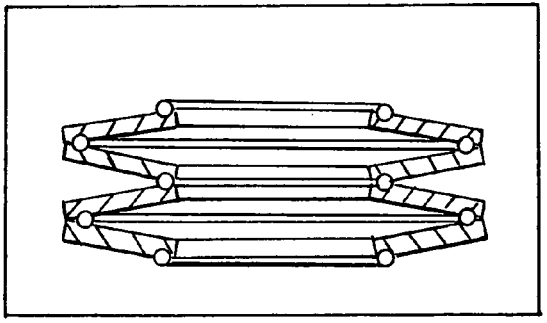

FIG. 41E

MULTICHANNEL FLUID DELIVERY DEVICE

BACKGROUND OF THE INVENTION

1. Field of the Invention

The present invention relates generally to fluid delivery devices. More particularly, the invention concerns an improved multi-channel apparatus for infusing various medicinal agents into an ambulatory patient at specific rates of flow over extended periods of time. The apparatus includes a novel energy source, a novel fill means for filling the reservoirs of the apparatus and a unique adjustable, multi-channel flow rate control means for precisely adjustably controlling the rate of fluid flow from individual reservoirs of the device toward the patient.

2. Discussion of the Prior Art

A number of different types of medicament dispensers for dispensing medicaments to ambulatory patients have been suggested. Many of the devices seek either to improve or lo replace the traditional gravity flow and hypodermic syringe methods, which have been the standard for delivery of liquid medicaments for many years.

The prior art gravity flow methods typically involve the use of intravenous administration sets and the familiar flexible solution bag suspended above the patient. Such gravametric methods are cumbersome, imprecise and require bed confinement of the patient. Periodic monitoring of the apparatus by the nurse or doctor is required to detect malfunctions of the infusion apparatus.

Many medicinal agents require an intravenous route for administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose can result in a toxic reaction.

For those patients that require frequent injections of the same or different amounts of medicament, the use of the hypodermic syringe method of delivery is common. However for each injection, it is necessary to first draw the injection dose into the syringe, then check the dose and, after making certain that all air has been expelled from the syringe, finally, inject the dose either under bolus or slow push protocol. This cumbersome and tedious procedure creates an unacceptable probability of debilitating complications, particularly for the elderly and the infirm.

As will be appreciated from the discussion, which follows, the apparatus of the present invention is uniquely suited to provide precise, multi-channel fluid delivery management in those cases where a variety of precise dosage schemes are of utmost importance. An important aspect of the apparatus of the present invention is the provision of novel fill means for filling the reservoirs of the device using a plurality of conventional medicament vials, each having a pierceable septum. Another unique feature of the apparatus of the present invention is an embedded microcapillary multi-channel flow rate control means, which enables precise control of the rate of fluid flow of the medicament to the patient. More particularly, the apparatus of the present invention, includes a unique, adjustable fluid flow rate mechanism which enables the fluid contained within the various reservoirs of the device to be precisely dispensed at selected rates.

The apparatus of the present invention can be used with minimal professional assistance in an alternate health care environment, such as the home. By way of example, devices of the invention are readily portable and can be used for the continuous infusion of injectable anti-infectives, hormones, steroids, blood clotting agents, analgesics and like medicinal agents. Similarly, the devices oft the invention can be used for most I-V chemotherapy and can accurately deliver fluids to the patient in precisely the collect quantities and at extended micro fusion rates over time.

By way of summary, the apparatus of the present invention uniquely overcomes the drawbacks of the prior art by providing a novel, disposable dispenser of simple but highly reliable construction. A particularly important aspect of the apparatus of the present invention resides in the provision of a novel, self-contained energy source in the form of a substantially constant-force compressible, expandable or retractable member that provides the force necessary to uniformly and precisely dispense various solutions, including medicament mixtures from a plurality of standard, prefilled vial containers that can be conveniently loaded into the apparatus. Because of the simplicity of construction of the apparatus of the invention, and the straightforward nature of the energy source, the apparatus can be manufactured at low cost without in any way sacrificing accuracy and reliability.

With regard to the prior art, one of the most versatile and unique fluid delivery apparatus developed in recent years is that developed by the present inventor and described in. U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly.

Another prior art patent issued to the present applicant, namely U.S. Pat. No. 5,743,879) discloses an injectable medicament dispenser for use in controllably dispensing fluid medicaments from a prefilled container at a uniform rate. The dispenser, which is quite dissimilar in construction and operation from that of the present invention, includes a stored energy source in the form of a compressively deformable, polymeric elastomeric member that provides the force necessary to controllably discharge the medicament from a prefilled container which is housed within the body of the device. After having been deformed, the polymeric, elastomeric member will return to its starting configuration in a highly predictable manner.

Another important prior art fluid delivery device is described in the U.S. Pat. No. 6,063,059 also issued to the present inventor. This device, while being of a completely different construction embodies a compressible-expandable stored energy source somewhat similar to that used in the apparatus of the present invention.

Still another prior art fluid delivery device, in which the present invention is also named as an inventor, is described in U.S. Pat. No. 6,086,561. This latter patent incorporates a fill system that makes use of conventional vials and cartridge medicament containers.

SUMMARY OF THE INVENTION

It is an object of the present invention to provide a compact fluid dispenser for use in controllably dispensing fluid medicaments, such as, antibiotics, oncolytics, hormones, steroids, blood clotting agents, analgesics, and like medicinal agents from prefilled or field filled containers at a uniform rate.

Another object of the invention is to provide a small, compact fluid dispenser that includes a housing to which fill vials can be connected for filling the dispenser reservoir with the injectable fluid.

Another object of the invention is to provide a dispenser in which a stored energy source is provided in the form of a compressible, expandable or retractable member of novel construction that provides the force necessary to continuously and uniformly expel fluid from the device reservoir.

Another object of the invention is to provide a dispenser of the class described which includes a fluid flow control assembly that precisely controls the flow of the medicament solution to the patient.

Another object of the invention is to provide a dispenser that includes precise variable flow rate selection.

Another object of the invention is to provide a fluid dispenser, which is adapted to be used with conventional prefilled drug containers to deliver beneficial agents therefrom in a precise and sterile manner.

Another object of the invention is to provide a fluid dispenser of the class described which is compact, lightweight, is easy for ambulatory patients to use, is filly disposable, and is extremely accurate so as to enable the infusion of precise doses of medicament over prescribed periods of time.

Another object of the invention is to provide a fluid dispenser as described in the preceding paragraphs that can be used to dispense a selected medicament, or alternatively a controlled mixture of various medicaments and diluents.

Another object of the invention is to provide a device of the character described which embodies a novel fluid volume indicator that provides a readily discernible visual indication of the volume of fluid remaining in the device reservoir.

Another object of the invention is to provide a point-of-care, self-contained Medicament dispenser that is of very simple construction and includes vials that can be filled in the pharmacy or in the field at time of use.

An other object of the invention is to provide a fluid dispenser as described in the preceding paragraphs that is easy and inexpensive to manufacture in large quantities.

Another object of the invention is to provide a fluid dispenser as described in the preceding paragraphs that is easy and inexpensive to manufacture in large quantities.

BRIEF DESCRIPTION OF THE DRAWINGS

FIG. 2 is a top plan view of the apparatus shown in FIG. 1.

FIG. 3 is a left and view of the apparatus shown

FIG. 4 is a right in the view of the apparatus shown in FIG. 2.

FIG. 13B is a fragmentary, cross-sectional view of a portion of the bellows structure of the apparatus of the invention.

FIG. 14 is an end view of one of the fill vials of the apparatus of the invention for filing one of the fluid reservoirs of the apparatus.

FIG. 15 is a cross-sectional view taken along lines 15—15 of FIG. 4.

FIG. 15A is a cross-sectional view of an alternate form of syringe fill vial of the apparatus of the invention that can be filled in the field and can be used to fill the lowermost fluid reservoirs of the apparatus.

FIG. 15B is cross-sectional view of the alternate form of field fill vial of the apparatus shown in FIG. 1 5A, but showing the vial as it appears prior to being filled.

FIG. 20 is a generally perspective, front view of one form of the fluid flow control assembly of the apparatus of the invention.

FIG. 21 is a generally perspective, exploded front view of the fluid flow control assembly shown in FIG. 20.

FIG. 22 is a fragmentary cross-sectional view of one of the flow control channels formed in the flow control member shown in the left-hand portion of FIG. 20.

FIG. 23 is a generally perspective, rear view of the fluid flow control assembly of the apparatus of the invention shown in FIG. 20.

FIG. 24 is a generally perspective, exploded rear view of the fluid flow control assembly shown in FIG. 20.

FIG. 27A is an enlarged, cross-sectional view of the area designated as 27A in FIG. 27.

FIG. 28 is a generally perspective, exploded view of the primary operating components of the apparatus of the invention shown in FIG. 27.

FIG. 28A is a generally perspective, fragmentary view of the ullage portion of the apparatus of the invention shown in FIG. 28 for insuring the expulsion of substantially all of the fluid from the fluid reservoirs of the apparatus.

FIG. 29 is a cross-sectional view of the alternate form of the syringe fill vial of the apparatus of the invention that can be filled in the field and can be used to fill the lowermost fluid reservoirs of the apparatus.

FIG. 30 is cross-sectional view of the alternate form of field fill vial of the apparatus shown in FIG. 29, but showing the vial as it appears prior to being filled.

FIGS. 31 and 31A, when considered together, comprise an enlarged, generally perspective, exploded view of an alternate form of the flow rate control means of the apparatus of the invention for controlling the rate of fluid flow toward the patient.

FIG. 32 is a view taken along lines 32—32 of FIG. 31.

FIG. 33 is a view taken along lines 33—33 of FIG. 31.

FIG. 34 is a generally perspective, rear view of the outlet manifold of the flow control means of the invention.

FIG. 35 is a generally perspective, front view of the outlet manifold of the flow control means of the invention.

FIG. 36A is a front view of the outlet manifold of the flow control means of the invention.

FIG. 37 is an enlarged, cross-sectional view of the area designated in FIG. 27 by the numeral 37, illustrating an alternate form of flow rate control assembly.

FIG. 37A is an enlarged, cross-sectional view of the area designated as 37A in FIG. 37.

FIG. 38 is a view taken along lines 38—38 of FIG. 37.

FIG. 40A is a greatly enlarged cross-sectional view of the central portion of the apparatus shown in FIG. 39.

FIG. 40B is an enlarged cross-sectional view of the area designated in FIG. 40 by the numeral 40B.

FIG. 40C is an, cross-sectional view of the uncompressed lower portion of the elastomeric band shown in FIG. 40B.

FIG. 40D is an enlarged, cross-sectional view of the uncompressed upper portion of the elastomeric band shown in FIG. 40B.

FIGS. 41A, 41B, 41C and 41D when considered together comprise a generally diagrammatic, tabular view illustrating various forms of the spring type stored energy means of the invention (hereinafter collectively referred to as FIG. 41)

FIG. 41E is a generally diagrammatic, tabular view further illustrating various stacking configurations of disc type springs of the stored energy means of the invention.

DESCRIPTION OF THE INVENTION

Figure 1:
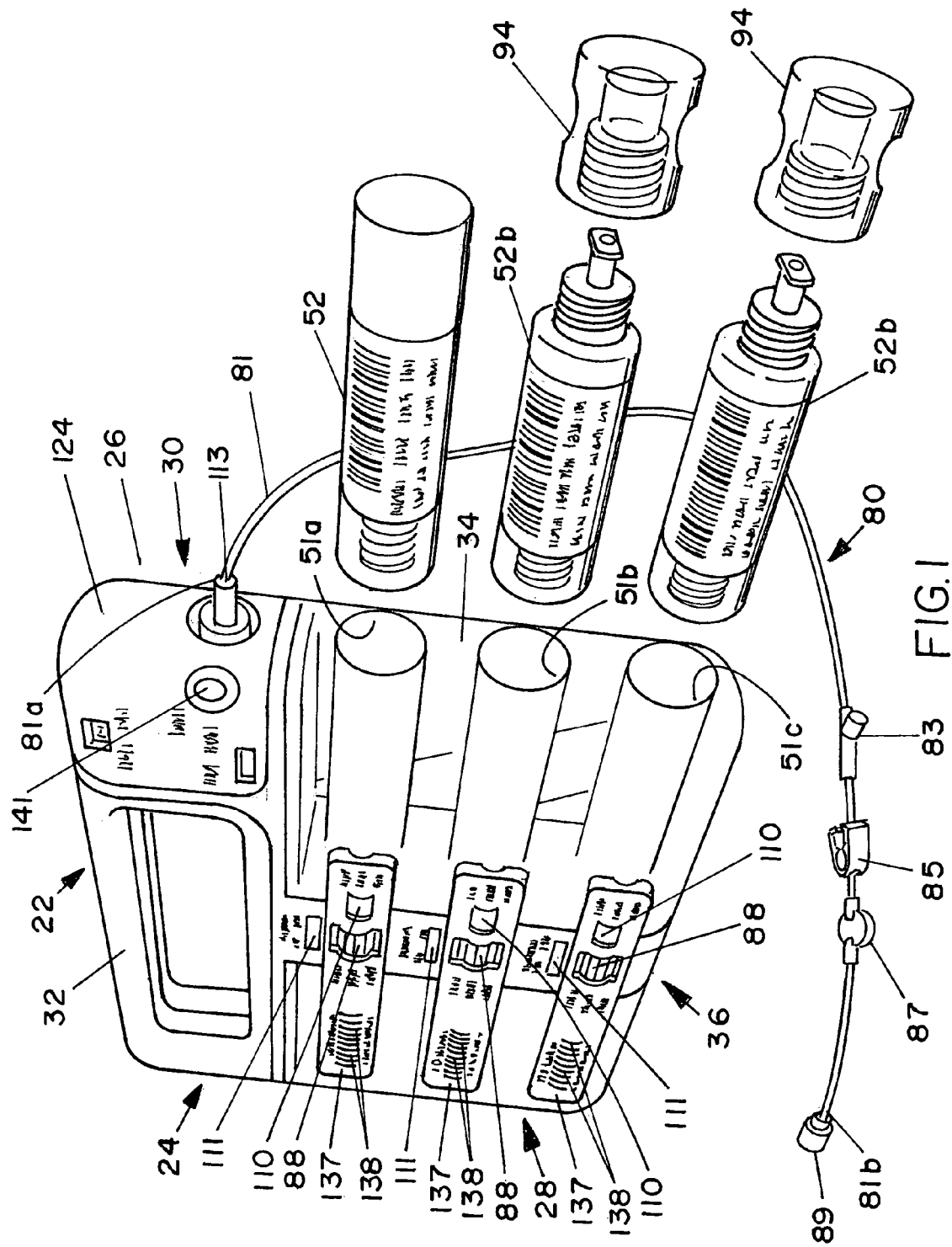
FIG. 1 is a generally perspective view of one embodiment of the multi-channel fluid delivery apparatus of the present invention for dispensing fluids at a uniform rate showing the medicament fill containers in position to be mated with the infusion device component of the apparatus.
Figure 1A:
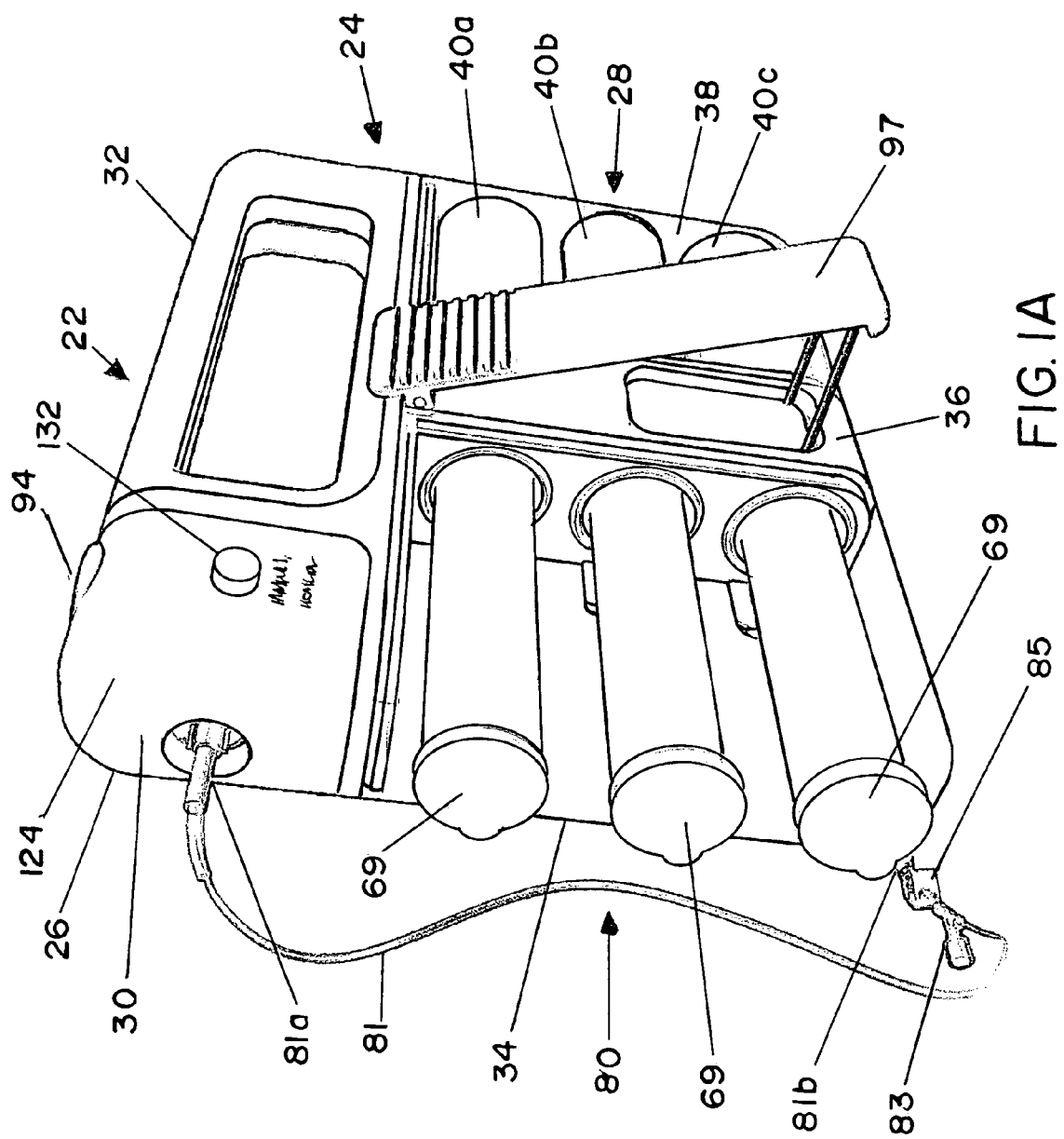
FIG. 1A is a generally perspective view of the fluid delivery apparatus of the invention shown in FIG. 1 as it appears prior to mating the medicament fill containers with the infusion apparatus.
Figure 5A:
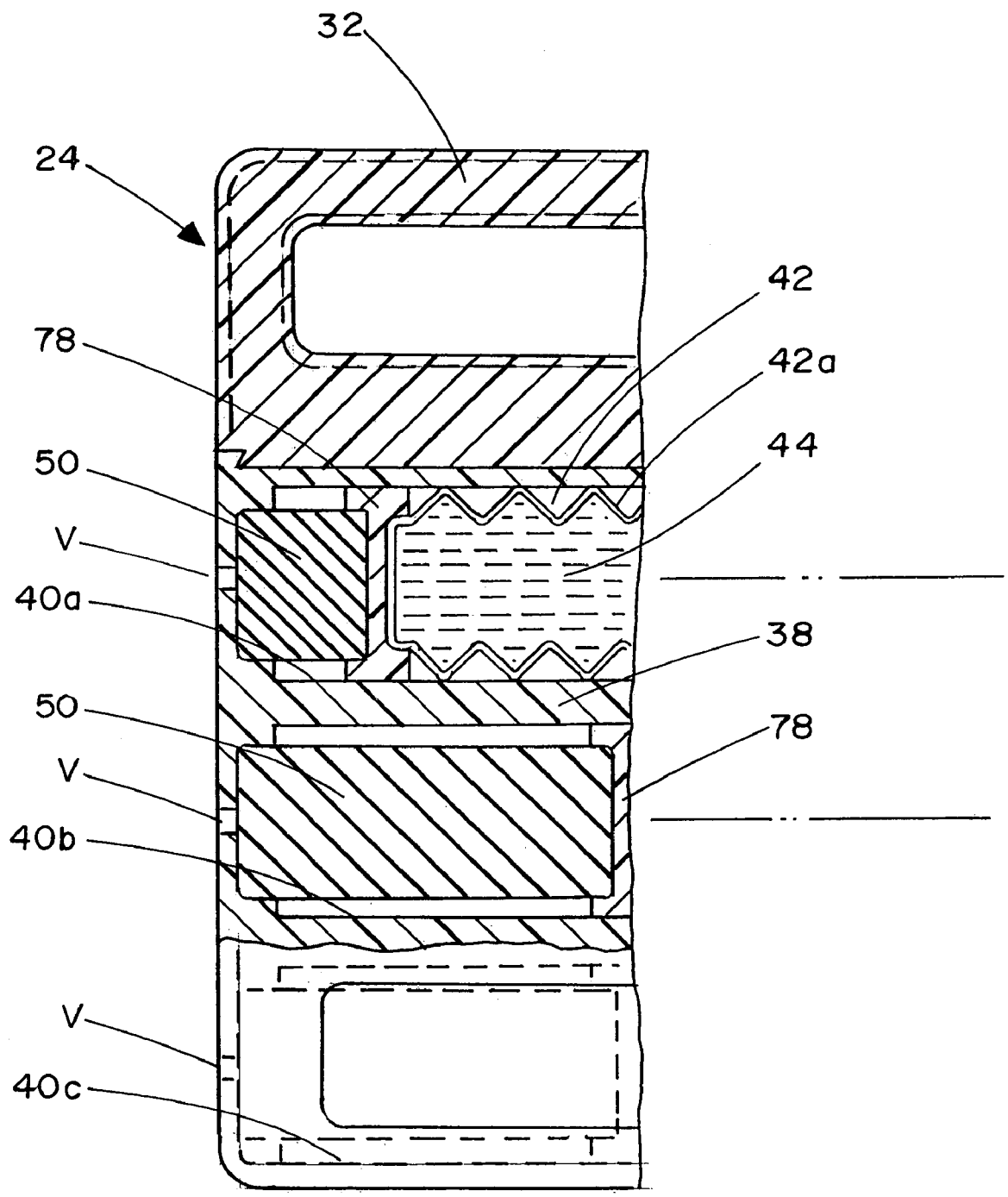
FIGS. 5A, 5B and 5C when considered together comprise a cross-sectional view taken along lines 5—5 of FIG. 4 (hereinafter collectively referred to as FIG. 5)
Figure 5B:
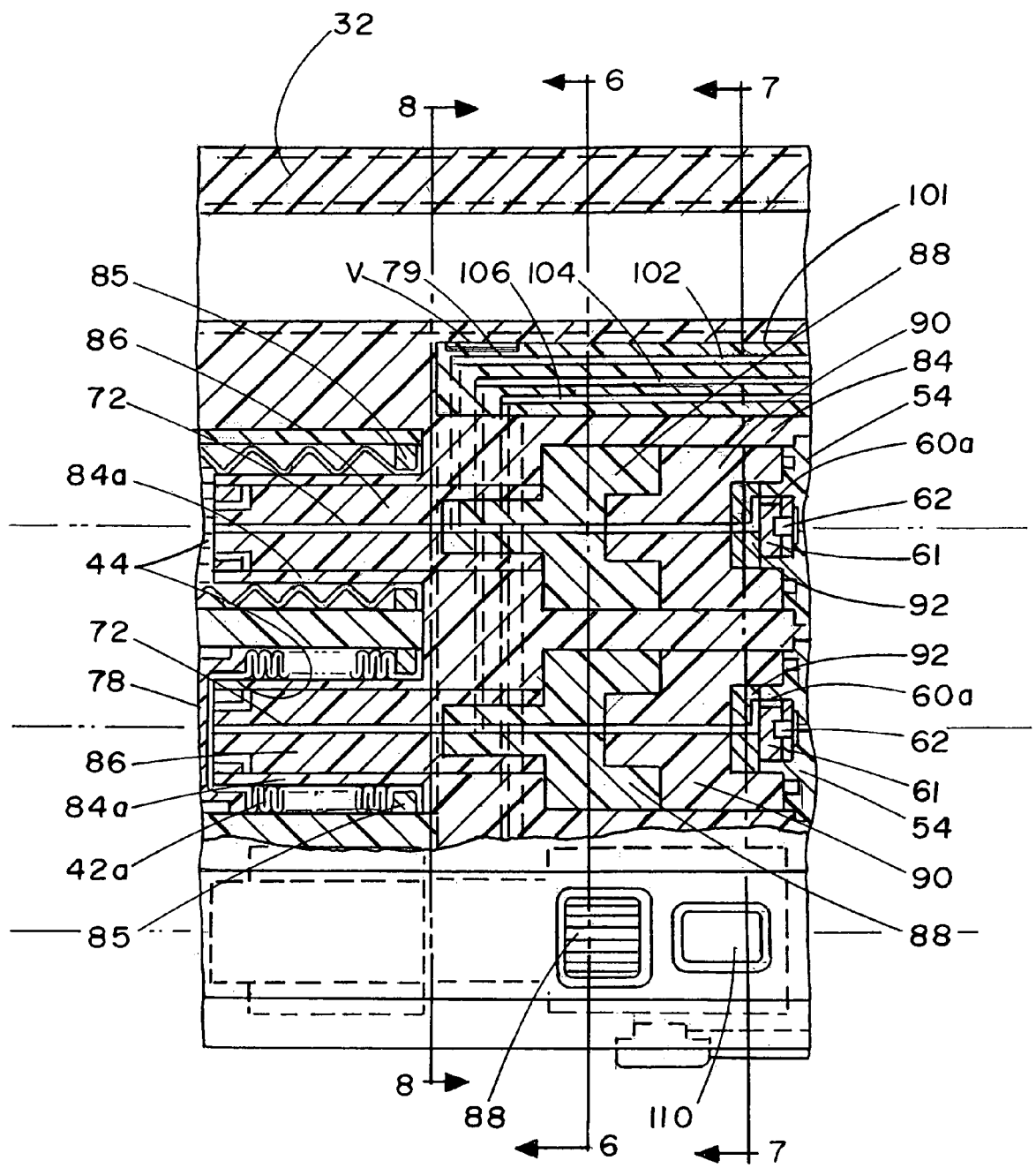
Figure 5C:
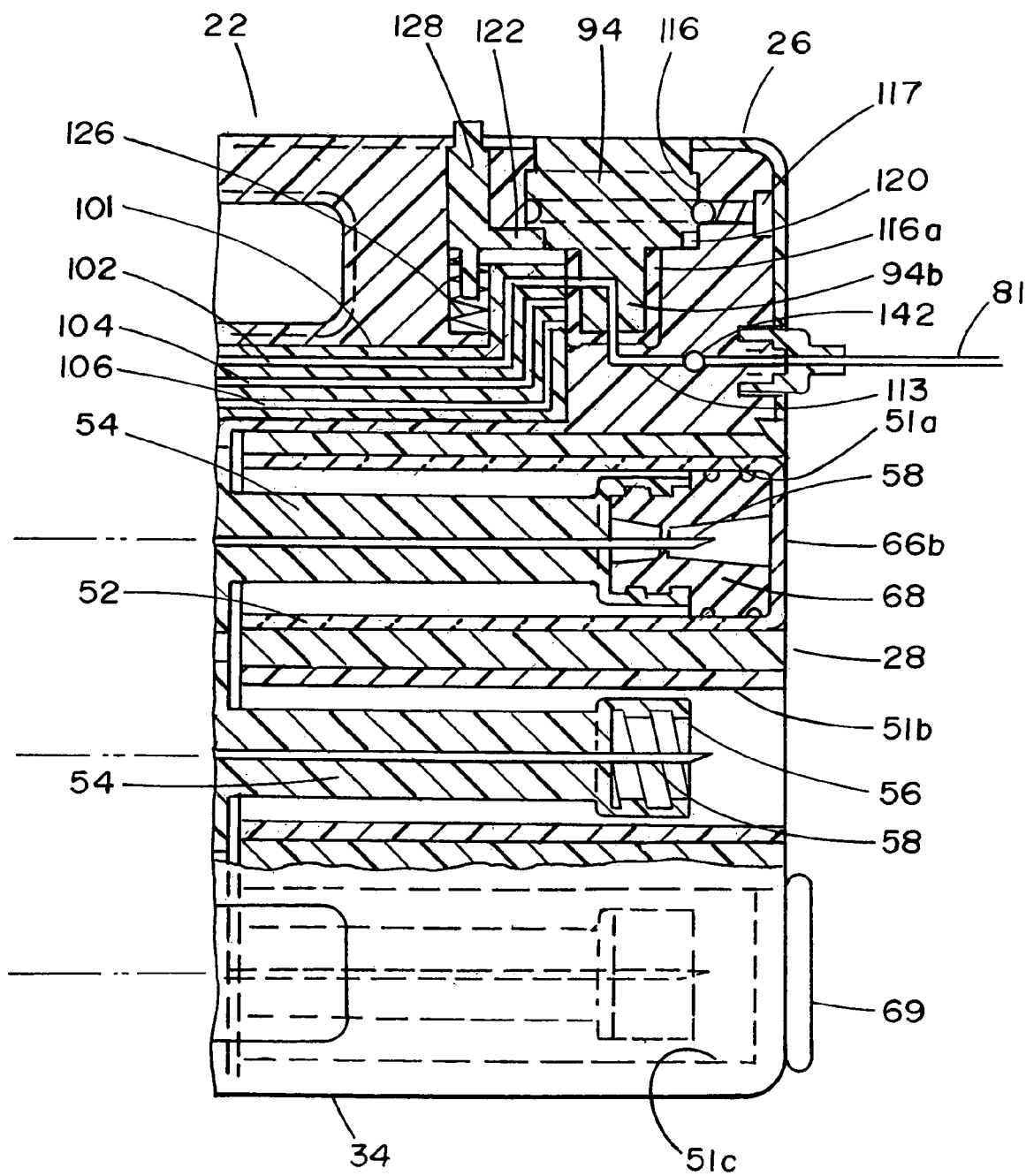
Figure 7:
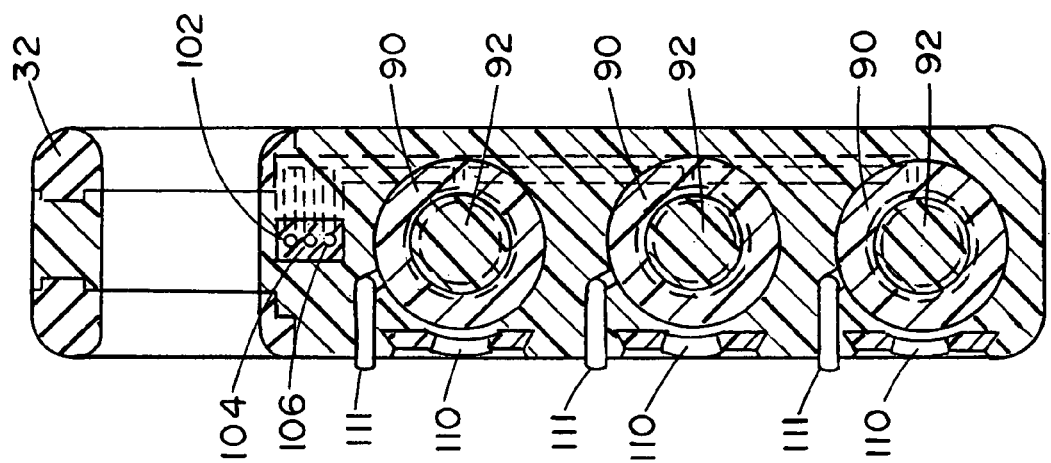
FIG. 7 is a cross-sectional view taken along lines 7—7 of FIG. 5.
Figure 6:
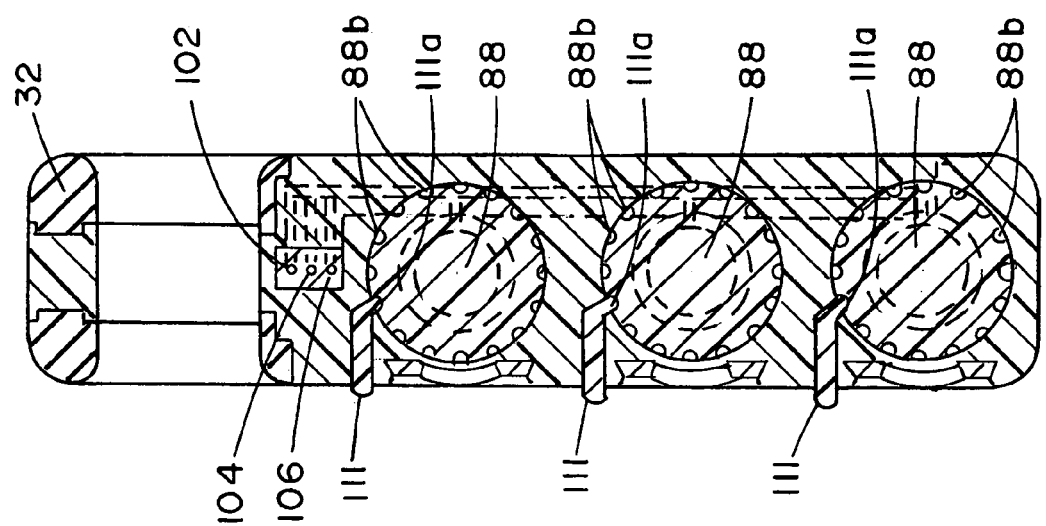
FIG. 6 is a cross-sectional view taken along lines 6—6 of FIG. 5.

Referring to the drawings and particularly to FIGS. 1 through 5, one embodiment of the multi-channel fluid dispensing apparatus of the present invention is there illustrated and generally designated by the numeral 22. As best seen in FIGS. 1, 1A and 5, the apparatus here comprises an outer housing 24 having upper and lower portions 26 and 28 respectively. Upper portion 26 includes a fluid dispensing portion 30 and a handle portion 32. Lower portion 28 of the housing comprises a first end, or fill portion 34, a central, or control portion 36 and a second end, or fluid reservoir portion 38. In one form of the invention, housing 24 is constructed from a moldable plastic such as polycarbonate, acrylic and like materials.

Figures 13, 13B:
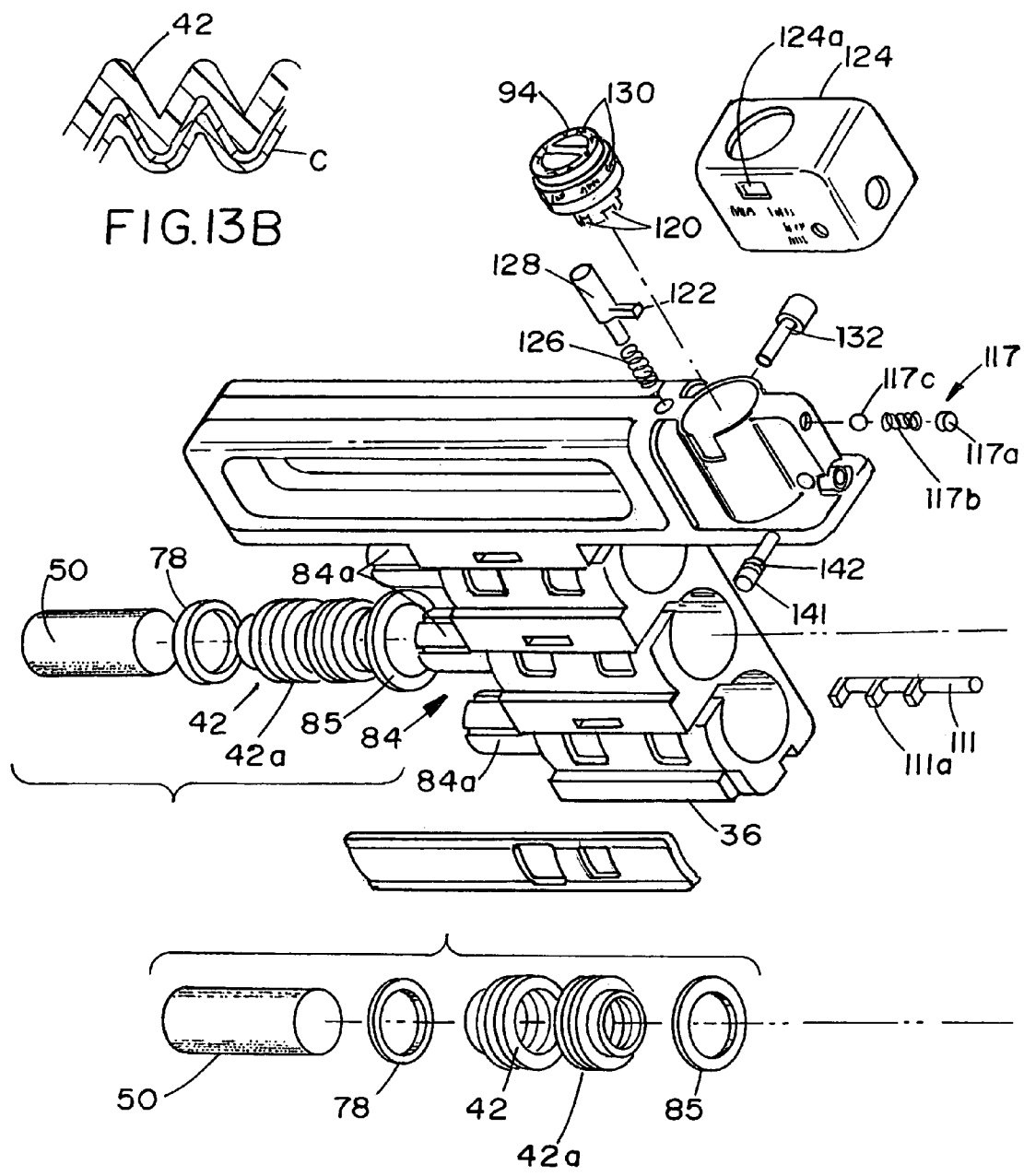
FIGS. 13A and 13B when considered together comprise a generally perspective exploded view of key portions of the apparatus of the invention shown in FIG. 1 (hereinafter collectively referred to as FIG. 13)

Considering first the fluid reservoir portion 38, as best seen in FIG. 5, this portion of the apparatus houses three vertically spaced apart fluid reservoir assemblies 40a, 40b and 40c, which are of substantially identical construction and operation. Disposed within each of the fluid reservoir assemblies 40a, 40b and 40c is an inner, expandable housing 42 having a fluid reservoir 44 provided with an inlet 46 (FIG. 5) for permitting fluid flow into the fluid reservoir. Expandable housings 42, which can be constructed from a metal or plastic material, comprise a bellows structure having an expandable and compressible, accordion-like, annular-shaped sidewall 42a, the configuration of which is best seen in FIG. 13.

Figure 13A:
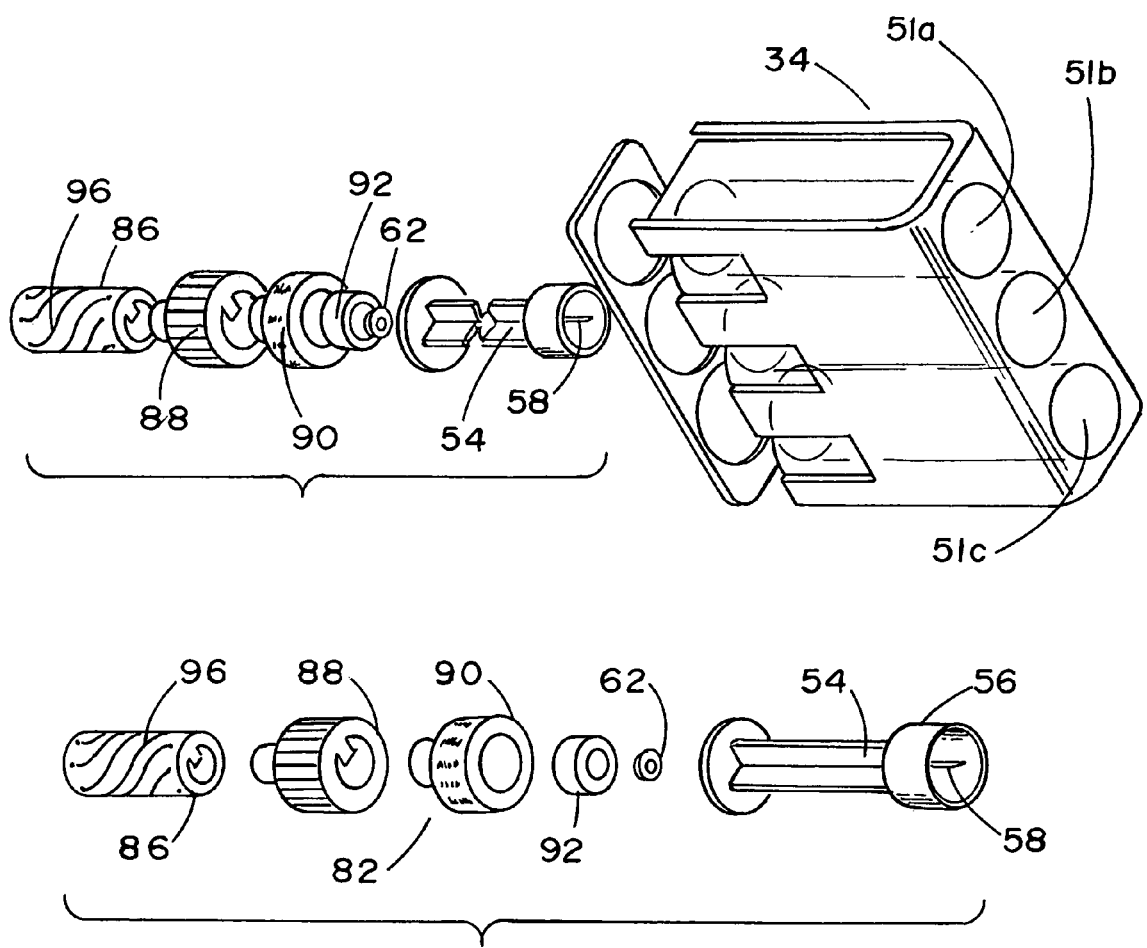

If the internal materials interface of the bellows structure and other fluid channels or surfaces are not sufficiently compatible with the planned beneficial agent to be delivered, either in terms of its biocompatibility or drug up-take characteristics, application of one or more selected coating "C" (see for example in FIGS. 13A and 22) through use of a surface modification process is appropriate. This surface modification methodology can take one of several forms. One methodology that is extremely clean, fast and efficient is plasma processing. In particular, this technique allows for any of the following: plasma activation, plasma induced grafting and plasma polymerization of molecular entities on the internal drug surface of the bellows. For cases where an inert hydrophobic interface is desired, plasmas using fluorine-containing molecules may be employed. That is, the bellows surface as well as other surfaces that may be contacted by the beneficial agent may be cleaned with an inert gas plasma, and subsequently, fluorine-containing plasma may be used to graft these molecules to the surface. Alternatively, if a hydrophobic surface is desired (e.g. for drug solutions that are highly corrosive or in oil-based solvents) an initial plasma cleaning may be first accomplished using a plasma polymerization using hydrophobic monomers.

Also disposed within second portion 38 of outer housing 24 are the novel stored energy means of the invention for acting upon expandable housings 42 in a maimer to controllably collapse the expandable housings so as to cause the fluid contained within the fluid reservoirs 44 to controllably flow outwardly of the housing. In the present form of the invention, these important stored energy means comprise compressively deformable, generally homogeneous members 50 that are carried within the second portion 38 of the outer housing in the manner shown in FIG. 5. As used herein, the term "homogeneous" means a materials member of the same general composition or structure throughout, that is, of the same kind and nature as opposed to a member consisting of different elements.

In a manner presently to be described stored energy members 50, which here comprise elastomeric polymeric elements or members, are compressed by fluid flowing into reservoir 44 and then are controllably expanded to cause fluid flow from the outer housing through the dispensing means of the invention. It is to be understood that the stored energy means can be constructed from a wide variety of solid, semisolid, and cellular materials including open cell, closed cell, syntactic forms with micro spheres, gas-filled, deformable cells, rubbers, foams, sponges, metallized foals, plastics and other thermoplastic elastomers (TPE). Other suitable materials include latex rubber, rubber polyolefins, polyisoprene (natural rubber), butyl rubber, nitrile lubber, polystyrene, polyethylene, polyvinyl chloride polyurethane, vinyls, vinyl-end-blocked polydimethylsiloxanes, other homopolymer, copolymers (random alternating, block, graft, cross-link and star block), silicones and other flouropolymers, mechanical poly-blends, polymer alloys and interpenetrating polymer networks. Suppliers of elastomeric materials suitable for construction of the polymeric members include 2 and 5 Plastics of Newark, N.J., Ludlow Composite Corp. of Fremont, Ohio and Polymer Technologies, Inc. of Newark, Del. Members 50 can also comprise a highly ductile metalized foam of the character available from various sources, including Chemetall of Frankfurt, Germany.

Forming an important aspect of the apparatus of the present invention is fill means carried by portion 34 of the outer housing for filling the reservoirs 44 with the fluid to be dispensed. Portion 34 includes three vertically spaced apart chambers 51a, 51b, and 51c each of which is constructed and arranged to telescopically receive a medicament containing fill vial, such as the closed-end glass or plastic shell via 52 depicted in FIG. 15 and the field fill vials 52b shown in FIGS. 15A and 15B. As shown in FIG. 1, vials 52 and 52b are each provided with an outer casing having medicament identifying indicia, imprinted thereon. Closure caps 94 close the ends of the casings.

Figure 25:
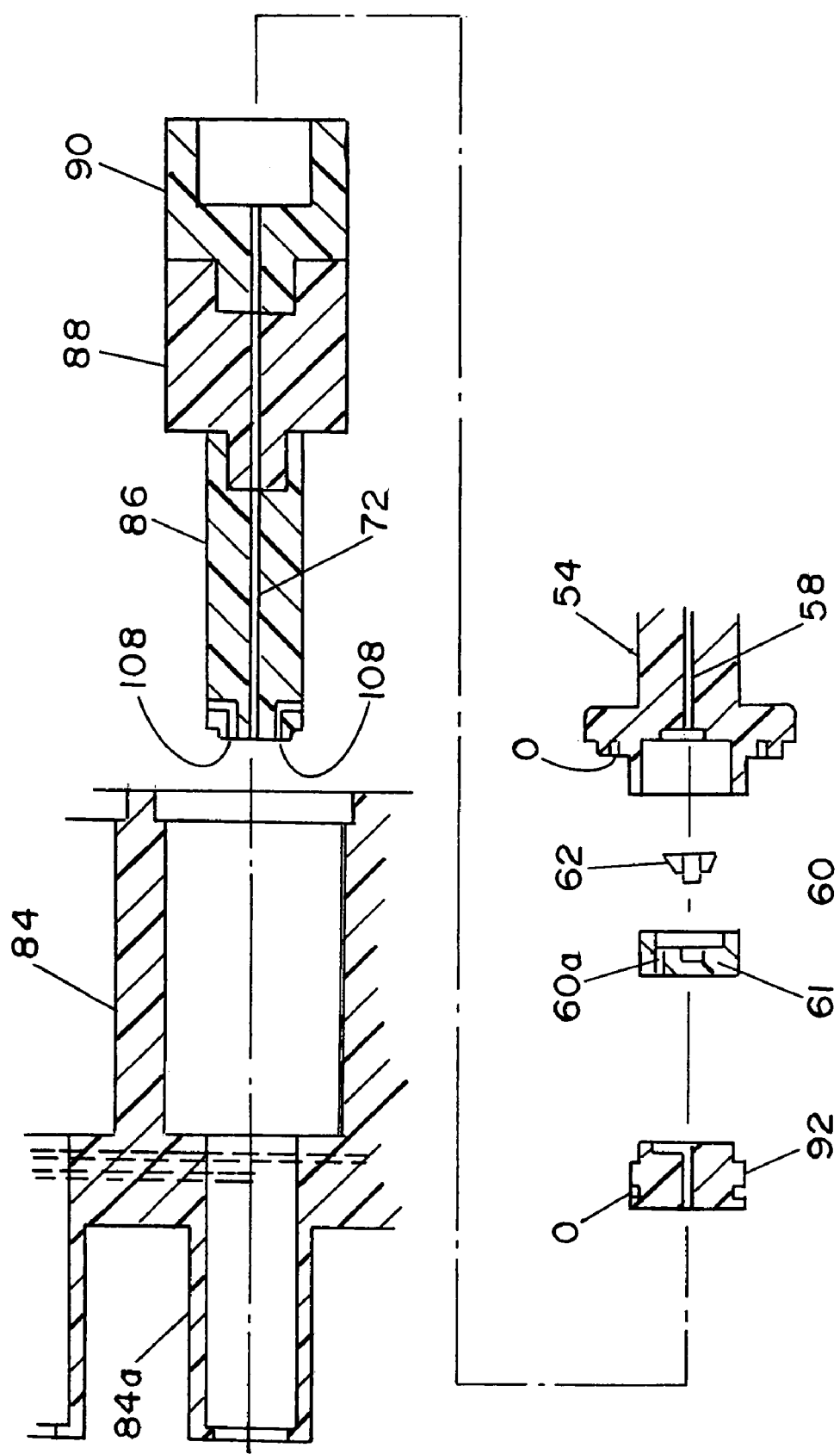
FIG. 25 is a fragmentary, exploded cross-sectional view of a portion of the apparatus housing, of the uppermost flow control assembly and a portion of the uppermost reservoir fill assembly of the apparatus of the invention shown in FIG. 5.

As described in FIGS. 5 and 13, an elongated support 54 is sealably connected to housing 36 and is mounted within each of the chambers 51a, 51b, and 51c. Each of the elongated supports 54 has a threaded end portion 56 and carries a longitudinally extending, elongated hollow needle or cannula 58. Each of the hollow needles 58 has a flow passageway that communicates with a chamber 60 formed in housing portion 61 that houses a conventional umbrella type check valve 62, the purpose of which will presently be described (FIGS. 5 and 25). Chambers 51a, 51b, and 51c, elongated supports 54, and hollow needles 58 together comprise the fill means of the apparatus of the form of the invention shown in FIGS. 1 through 13. The method of operation of this important fill means will be described in greater detail in the paragraphs which follow.

Turning particularly to FIGS. 1, 5 and 15, prefilled fill vial 52 call be seen to include a body portion 64, having a fluid chamber 66 for containing an injectable fluid. Chamber 66 is provided with a first open end 66a and second closed end 66b. First open end 66a is sealably closed by closure means here provided in the form of an externally threaded elastomeric plunger 68 which is telescopically movable within the vial from a first location shown in. FIG. 15 where the plunger is disposed proximate first open end 66a, to a second location where the fluid has been expelled and plunger is disposed proximate second closed end 66b.

After opening the uppermost closure 69 (FIG. 1A), vial 52 can be inserted into chamber 51a and the plunger 68 can be threadably interconnected with end 56 of the uppermost support 54. In so doing, the sharp end of the uppermost elongated needle 58 will pierce the central walls 68a of the elastomeric plunger. Continuous longitudinal movement of the vial into chambers 51a will cause the structural support 54 to move the elastomeric plunger inwardly of the vial chambers in a direction toward the second closed end 66b of the vial. As the plunger is moved inwardly of the vial in the manner shown in the upper portion of FIG. 5, to a position wherein the plunger resides proximate closed end 66b, the fluid contained within the vial chamber will be expelled therefrom into the uppermost hollow elongated needle 58. As illustrated in FIG. 5, the fluid will then flow past the uppermost umbrella type check valve 62 and into the uppermost elongated, central passageway 72 which communicate with the uppermost fluid reservoir 44 of the bellows component 42. With the construction shown in FIG. 5, the elastomeric, umbrella type check valves 62 will function in a traditional manner to substantially block reverse fluid flow from fluid passageways 72. It is to be understood that the vials 52 and 52b can contain the same or different medicinal fluids or diluents.

As the fluid flows into the reservoir portion of the uppermost bellows, the bellows will be expanded from a collapsed configuration into an expanded configuration, such as shown in the upper left end portion of FIG. 5. As the reservoir 44 fills with fluid, any gases trapped within the reservoirs will be vented to atmosphere via vent means "V" mounted in housing 24 proximate handle 32 (FIG. 5).

Upon opening the fluid delivery path to the of the dispensing means invention, shown here as comprising a fluid administration set 80 (FIG. 1), the stored energy means, or members 50, will tend to return to their starting configuration thereby controllably urging fluid flow outwardly of selected reservoirs 44 via the flow control means of the invention. In the present form of the invention, fluid administration set 80 comprises a part of the dispensing means of the invention for delivering medicinal fluids to the patient. As shown in FIG. 1, administration set 80, which is connected to portion 30 of housing 24, includes an administration line 81 having a proximal end 81*a* that is in communication with fluid passageway 113 (FIG. 5). Disposed between the proximal and 81*a* and the distal end 81*b* of the administration line is a conventional "Y" site injection septum or port 83, a line clamp 85 and a conventional gas vent and particulate filter 87. Provided at the distal end 81*b* of the administration line is a luer connector 89 of conventional construction.

As previously discussed, a number of beneficial agents can be contained within liquid vial containers 52 and 52*b* and can be controllably dispensed to the patient. These beneficial agents can include, by way of example, medicaments of various types, drugs, pharmaceuticals, hormones, antibodies, biologically active materials, elements, chemical compounds, or any other suitable material useful in diagnostic cure, medication, treatment or preventing of diseases or the maintenance of the good health of the patient.

As illustrated in FIGS. 15A and 15B, the fill vials 52*b*, which are received within lower chambers 51*b* and 51*c*, and which are of the identical construction, each include a body portion 91, having a fluid chamber 91*a* for containing an injectable fluid. Chamber 91*a* is closed proximate one end by an aseptic, breathable peal seal closure member 95 and is closed proximate its other end by threaded closure cap 93*a* (FIG. 15B). Following filling and prior to vial installation, member 95 is removed as shown in FIG. 15A. An externally threaded elastomeric plunger 68 which is identical to that previously described is telescopically movable within the vial from a first location shown in FIG. 15B where the plunger is disposed proximate one end of the empty vial to a second filled vial location where the plunger is disposed proximate the opposite end thereof (FIG. 15A) Provided proximate one end of the vial is a connector block 93 which includes a luer connector 93*a* and a cavity portion 93*b*. Mounted within cavity 93*b* by means of a sealably connected plug 93*c* having flow passageways 93*d* is a conventional, umbrella type check valve 95. Reservoir 91*a* can be filled by interconnecting a conventional filling syringe "S" with the luer connector 93*a* in the manner shown in FIG. 15A. As the reservoir fills with the medicinal fluid to be dispensed, plunger 68 will move into the fill position shown in FIG. 15A. The umbrella check valve 95 functions to prevent fluid flow in a reverse direction toward the luer connector 93*a*.

After opening the lower closures 69 (FIG. 1A), the field filled, fill vials 52*b* can be inserted into their respective chambers 51*b* and 51*c* (FIG. 5). If desired, the housing can be supported in the upright position shown in FIG. 1A by a pullout support member 97. When the fill vials are inserted into their chambers, plunger 68 can be threadably interconnected with ends 56 of supports 54 (FIG. 5). In so doing, the sharp ends of the elongated needles 58 will pierce the central walls 68*a* of the elastomeric plunger. Continuous longitudinal movement of the vial into the chambers will cause the plungers to move inwardly forcing the fluid to be expelled via the elongated hollow needles 58 and into the passageways 72 that communicate with the fluid reservoirs 44 of the lower bellows components.

Similar to the loading of the uppermost bellows, as the fluid flows into the reservoir portion of the lower two bellows, the bellows will likewise expand from a collapsed configuration into an expanded configuration.

Forming another very important aspect of the apparatus of the present invention is the novel flow control means if the invention that are carried proximate the central portion of housing 24. These flow control means function to precisely control the rate of fluid flow outwardly from the various reservoirs 44 toward the administration set 80 and then toward the patient. Ill the form of the invention shown in FIGS. 1 through 25 the flow control means comprises a plurality of flow control assemblies generally designated in the drawings by the numeral 82 (FIGS. 5 and 13). These novel flow control assemblies, each of which is of identical construction, comprises a strategically configured casing portion 84 that is disposed within housing 36 (FIG. 13), a flow control member 86 that is telescopically receivable within ullage portion 84*a* of casing 84, a thumbwheel 88 connected to the flow control member and an indicator drum 90 that is connected to the thumbwheel (FIG. 25). Also forming apart of the flow control means is a fluid connector 92 that is sealably mounted within indicator drum 90 and properly oriented by a key 88*k* (see also FIG. 13). As indicated in FIG. 5, fluid connector 92 functions to interconnect the flow passageways of the elongated needles 58 of the fill means of the invention with the elongated passageways 72 which carry the medicinal fluids to reservoirs 44. In the present form of the invention, the flow control means further includes mixing and dispensing means, shown here as comprising a knob 94 that is rotatably carried within housing portion 26 in the manner best seen in FIG. 5. As will presently be described, the selection or mixing and dispensing knob 94 can be manipulated by the caregiver to select the medicinal, fluid, diluent or fluid mixture that is to be delivered to the patient in accordance with the dispensing protocol.

Considering first the construction of the novel flow control members 86 of the flow control means, particular reference should be made to FIGS. 13 and 20 through 24 of the drawings. As best seen in FIGS. 20 through 24, each of the flow control members 86 is uniquely provided with a plurality of elongated, strategically configured flow control channels 96, each having an inlet 96*a* and an outlet 96*b*. As indicated in the drawings, flow channels 96 may be of different lengths, widths, depths and shapes. The flow control channels are preferably formed in individual, spaced-apart capillary segments, each of which defines a circuitous flow path. As illustrated in FIG. 22, the flow control channels may be rectangular in cross-section, or alternatively, can be semicircular in cross-section, U-shaped in cross-section, or they may have any other cross-sectional configuration that may be appropriate to achieve the desired fluid flow characteristics. As indicated by the designation "C" in FIG. 22, when necessary for drug compatibility reasons, the flow channels can be appropriately coated. Coating or surface treatment "C" can be of various types and the coating can be applied by several techniques including the earlier-described plasma processing technique.

When the flow control member is properly positioned within end 84*a* of the ullage casing 84, which is sealably connected to bellows 42 by a sealing ring 85, (see FIGS. 5, 13 and 25), the inner surface of the casing wall cooperates with channels 96 to form a plurality of shaped fluid flow passageways of different overall lengths, widths and flow capacities. As shown in FIG. 5, when the flow control member is positioned within the ullage casing, a notch 86*b* formed in member 86 (FIG. 21) receives a tongue 88*a* provided on thumbwheel 88 (FIG. 24) so that upon rotation of the thumbwheel, a selected one of the outlets 96*b* of the flow channels 96 can be precisely aligned with a selected one of a plurality of spaced apart fluid passageways formed in casing 84 (FIG. 5). In a similar manner, as shown in FIGS. 21 and 24, a notch 88*b* formed in member 88 (FIG. 21) receives a tongue 90*a* provided on indicator drum 90 (FIG. 24) so as to cause concomitant rotation of the indicator drum as the thumbwheel is rotated.

Figure 9A:
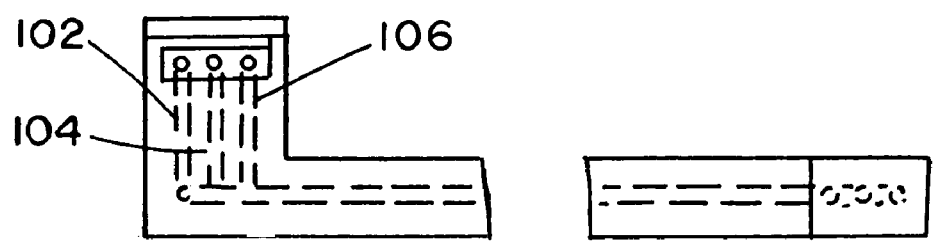
FIG. 9A is a top plan view of the construction shown in FIG. 9.
Figure 9:
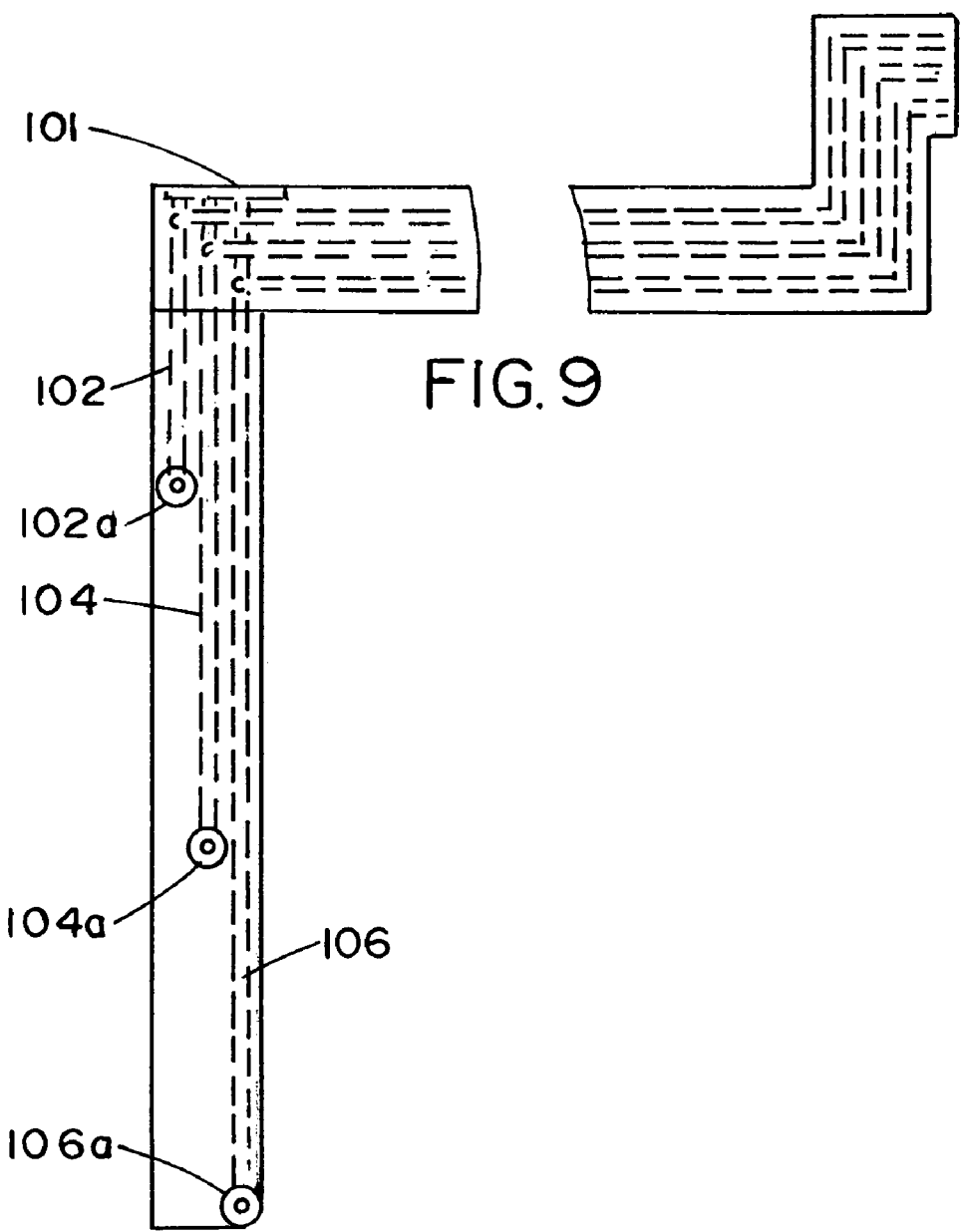
FIG. 9 is a fragmentary, generally diagrammatic view illustrating the fluid flow paths from the fluid reservoirs of the device toward the fluid outlets of the device.
Figure 8:
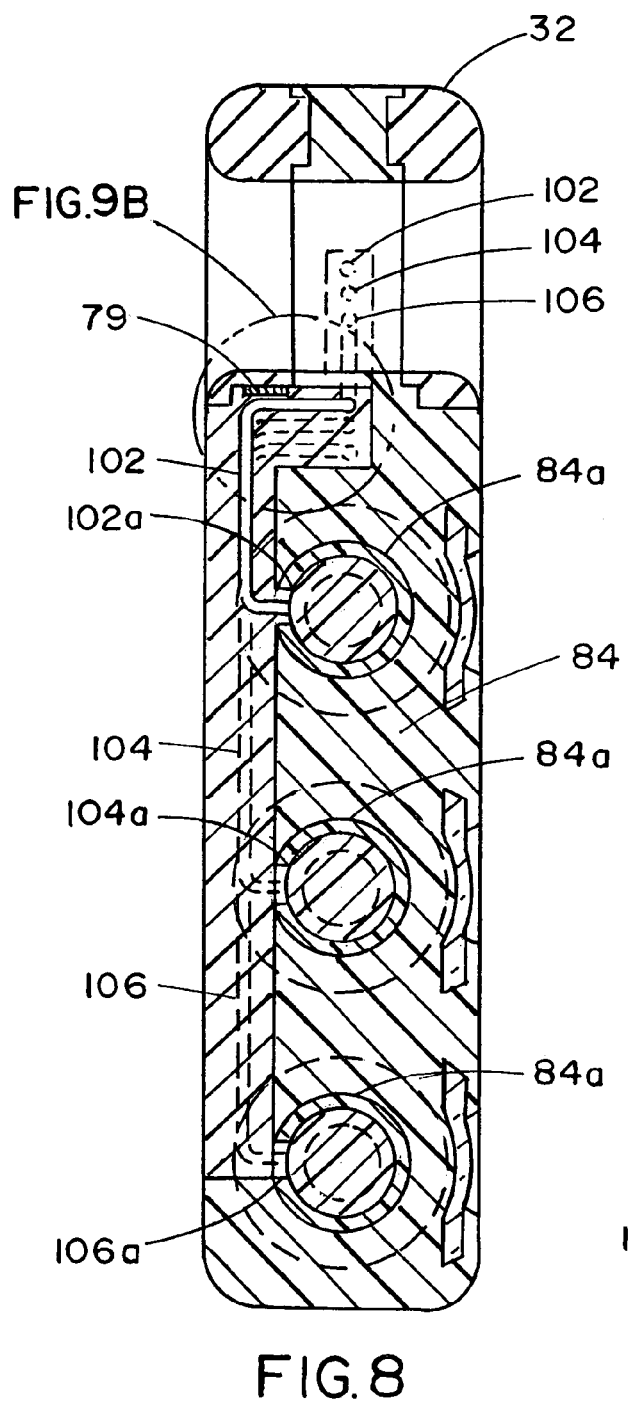
FIG. 8 is a cross-sectional view taken along lines 8—8 of FIG. 5.
Figure 9B:
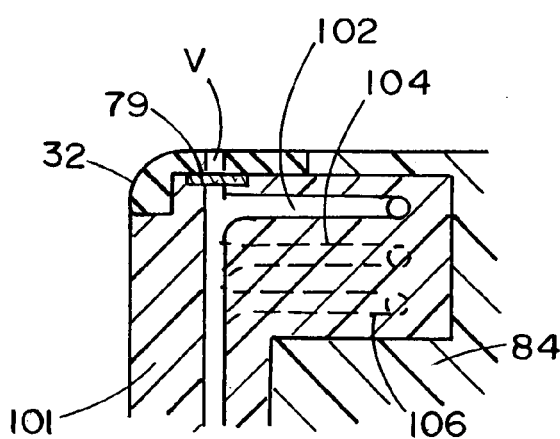
FIG. 9B is an enlarged cross-sectional view of the area designated as 9B in FIG. 8.

Referring particularly to FIGS. 8 and 9, it can be seen that a fluid transfer manifold 101 that communicates with ullage casings 84*a* is provided with a first, upper fluid passageway 102, a second, intermediate fluid passageway 104 and a third, lower passageway 106. Fluid passageway 102 communicates with a selected one of the plurality of the shaped fluid flow passageways 96 of the uppermost flow control member 86. In similar manner, fluid passageway 104 communicates with a selected one of the plurality of shaped fluid flow passageways 96 of the intermediate flow control member 86 and passageway 106 communicates with a selected one of the plurality of shaped fluid flow passageways 96 of the lowermost flow control member 86.

With the construction shown in the drawings and as described in the preceding paragraph, rotation of the uppermost thumbwheel 88 will permit a selected one of the outlets 96*b* of the flow passageways 96 of the uppermost flow control member 86 to be moved into register with the inlet 102*a* of passageway 102. This will cause the fluid flowing from the uppermost fluid reservoir through inlets 108 formed in members 86, which inlets comprise the outlets of the uppermost fluid reservoir (FIG. 23). Next, the flow will flow into passageway 102 at a selected rate of fluid flow (FIGS. 8 and 9). Similarly, rotation of the intermediate thumbwheel 88 will permit a selected one of the outlets 96*b* of the flow passageways 96 of the intermediate flow control member 86 to be moved into register with the inlet 104*a* of passageway 104. This will cause the fluid flowing from the intermediate fluid reservoir through inlets 108 formed in members 86, which inlets comprises the outlets of the intermediate fluid reservoir (FIG. 5), to flow in the passageway 104 at a selected rate of fluid flow. In like manner, rotation of the lowermost thumbwheel 88 will permit a selected one of the outlets 96*b* of the flow passageways 96 of the lowermost flow control member 86 to be moved into register with the inlet 106*a* of passageway 106. This will cause the fluid flowing front the lowermost fluid reservoir to flow into passageway 106 at a selected rate of fluid flow (FIGS. 8 and 9).

It is to be observed that, as the thumbwheels are rotated, the indicator drums 90 that are key and keyway associated therewith will also rotate. As the drums rotate, indicia 107, which is imprinted on each of the drums and which indicate fluid flow rate, can be viewed through upper, intermediate and lower viewing windows 110 provided in the apparatus housing (FIG. 1). In this way, the caregiver can precisely select the desired outward rate of fluid flow toward the administration set of the medicinal fluids contained within each of the upper, intermediate and lower fluid reservoirs. Once the flow rate has been selected, thumbwheel locking means are provided to securely lock the thumbwheel in the desired position. In the present form of the invention these thumbwheel locking means each comprises a slide member 111 (FIG. 1) that is operably associated with a selected one of the thumbwheels and is slidably carried by the apparatus housing for movement between a locked and unlocked position. Each slide member 111 is provided with a locking finger 111*a* (FIG. 6) that is movable into locking engagement with a selected one of a plurality of circumferentially spaced grooves 88*b* provided in each of the thumbwheels when the slide member is moved into the locked position. In order to reset the fluid flow rate, the appropriate locking slide rust be moved into the locked position. So long as the locking slide is in the locked position, accidental movement of the thumbwheels is positively prevented.

Figure 11:
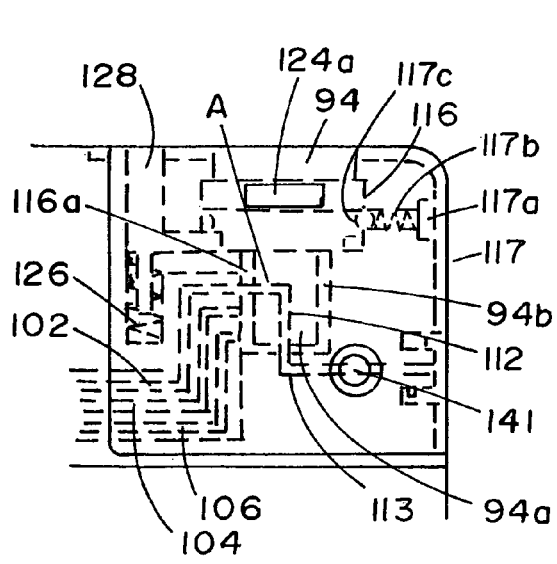
FIG. 11 is a fragmentary front view of the portion of the apparatus shown in FIG. 10, partly broken away to shown internal construction.
Figure 12:
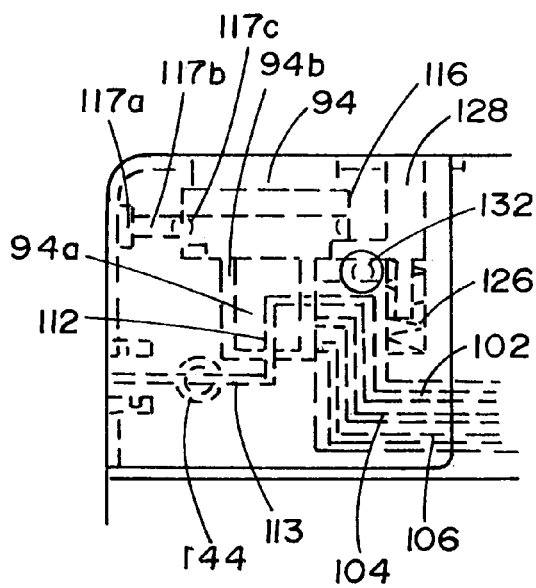
FIG. 12 is a fragmentary rear view of the portion of the apparatus shown in FIG. 10, partly broken away to shown internal construction.
Figure 16:
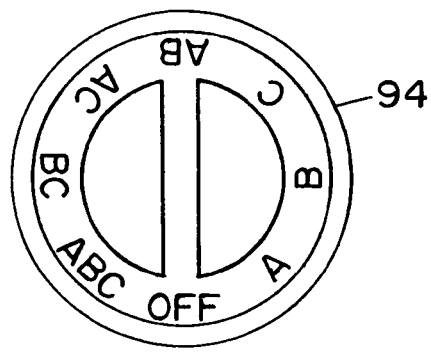
FIG. 16 is an enlarged, a top plan view of the mixing and dispensing knob of the apparatus of the invention.
Figure 17:
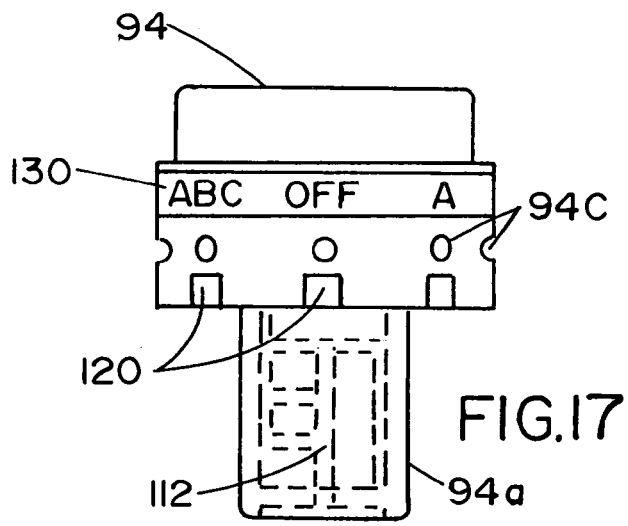
FIG. 17 is a front view of the mixing and dispensing knob shown in FIG. 16.
Figure 18:
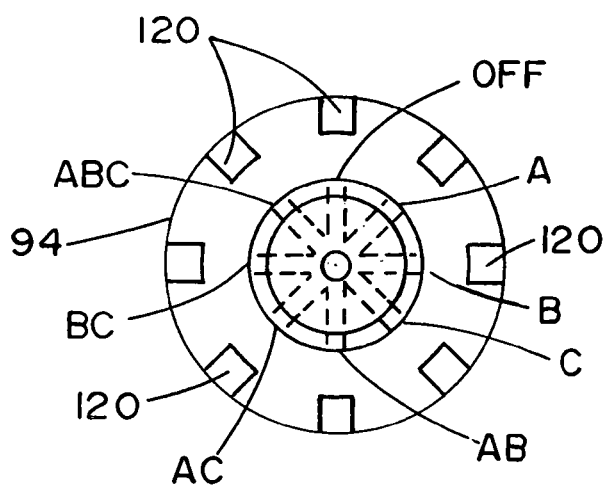
FIG. 18 is a bottom plan view of the mixing and dispensing knob shown in FIG. 17.

Turning next to FIGS. 16, 17 and 18, the construction of the important flow channel selector regulating means of the invention for selecting and regulating the flow of fluid from the various fluid reservoirs 44 toward the delivery means via the flow rate control means is there shown. As will presently be discussed, in greater detail, this important flow selecting and regulating means permits fluid flow to the patient of a single medicament from a, selected one of the fluid reservoirs 44, or alternatively permits the flow of a mixture of medicaments from two or more of the fluid reservoirs 44. In the present form of the invention this flow selecting and regulating means comprises a mixing and dispensing knob 94 that is rotatably mounted within the upper portion 26 of the apparatus housing (FIG. 13). As indicated in FIGS. 17 and 18, knob 94 has a central fluid flow passageway 112 and a plurality of radially outwardly extending fluid passageways that are in communication with the central passageway 112, with flow passageways 102,104 and 106 and also with an apparatus outlet passageway 113 (FIG. 5). The radially outwardly extending passageways of the selecting mixing and dispensing knob 94 are identified in FIG. 18 by the designations A, B, C, AB, AC, BC, ABC and OFF. As shown in FIGS. 2, 5, 11 and 12, the reduced diameter portion 94*a* of knob 94 is sealably received within a reduced diameter opening 116*a* provided in housing portion 26. Reduced diameter portion 94*a* of knob 94 is provided with an elastomeric coating 94*b* that prevents leakage of fluids between the reduced diameter portion of the knob and the wall of the reduced diameter opening 116*a*. With this construction, by controllably rotating knob 94 within opening 116, a selected one of the radial passageways can be aligned and with a selected one or more of the inlet passageways 102, 104 and 106 formed in the apparatus housing. Indexing means for indexing the position of knob 94 within opening 116 are here provided in the form of a spring-loaded indexing assembly 117 (FIGS. 11 and 12). As best seen in FIG. 13, this indexing assembly comprises a bonded head portion 117*a*, a coil spring portion 117*b* and on indexing ball 117*c* that is receivable within a selected one of a plurality of circumferentially spaced apart indexing cavities 94*c* provided on the periphery of knob 94 (FIG. 17). With this construction, spring 117*b* continuously urges indexing ball 117*c* into one of the cavities 94*c* (FIGS. 13 and 17).

Figure 19:
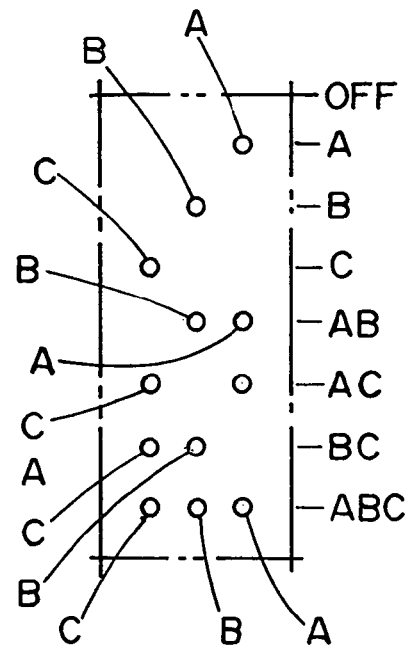
FIG. 19 is a generally diagrammatic, planar projection of a portion of the mixing and dispensing knob of the apparatus of the invention showing the arrangements of the various fluid inlet ports of the knob.

Indicia provided on the mixing and dispensing knob (FIGS. 16 and 17) indicates to the caregiver which of passageways 102, 104 and 106 are in alignment with which of the radial passageways formed in the knob 94 and in this way permits the caregiver to select the desired fluid flow protocol to the patient. For example, by rotating the knob to the position A, only fluid flow from the uppermost reservoir 44 of the apparatus will flow to the patient via passageway 102, which is then aligned with radial passageway A of the knob 94 (FIGS. 11 and 12). In this position, the fluid will flow from the upper reservoir toward the patient via passageways 112 and 113 at the rate of flow previously selected by the caregiver through rotation of the uppermost thumbwheel 88. Similarly, by rotating the knob to the position B, only fluid flow from the intermediate reservoir 44 of the apparatus will flow to the patient via passageways 112 and 113 at the rate of fluid flow previously selected by the caregiver through the rotation of the intermediate thumbwheel 88. In like manner, by rotating the knob to the position C where the radial passageway C is in alignment with passageway 106, only fluid flow from the lowermost reservoir 44 of the apparatus will flow to the patient via passageways 112 and 113 at the rate of fluid flow previously selected by the caregiver through the rotation of the lowermost thumbwheel 88. However, when the caregiver desires to deliver a mixture of medicaments to the patient, knob 94 can be rotated, by way of example, to the position AB where both passageways 102 and 104 are in communication with central passageway 112 of the knob 94 via the appropriate radial passageways formed in knob 94 and are also in communication with outlet passageway 113. FIG. 19, which is a vertically oriented, planar projection of portion 94a of the knob, further illustrates the strategic positioning of the radial passageways provided in knob 94. If, by way of example, the caregiver desires to simultaneously deliver to the patient a mixture of the medicaments contained within the upper, intermediate and lower reservoirs, the mixing and dispensing knob 94 can be rotated to the position ABC wherein all of the passageways 102, 104 and 106 are all in communication with central passageway 112, which passageway is, in turn, in communication with device outlet passageway 113.

In all cases, the rate of the flow of the fluid from each of the reservoirs is governed by the positioning of the thumbwheels 88 in the manner described in the preceding paragraph. From the foregoing, it is apparent that, through rotation of the thumbwheels 88 and rotation of the selecting, mixing and dispensing knob 94, the medicaments contained within the apparatus reservoirs can be independently delivered to the patient at a selected flow rate, or alternatively, selected mixtures of the medicaments contained within the various apparatus reservoirs can be simultaneously delivered to the patient at precisely selected delivery rates.

To maintain the selecting, mixing and dispensing knob 94 in a selected position, knob-locking means of the character best seen in FIGS. 5, 11, 12 and 17 are provided. As illustrated in FIGS. 5 and 13, the selecting mixing and dispensing knob is here provided with a plurality of circumferentially spaced apart cavities 120 that closely receive an indexing locking finger 122 that forms a part of the locking means of the invention. The locking means also here comprises a hollow cover 124 that forms a part of housing portion 26. With the construction shown in the drawings, indexing locking finger 122 is continuously urged into engagement with a selected one of the indexing cavities 120 by a coil spring 126 that also forms a pair of the indexing means of the invention. Coil spring 126 can be compressed by an inward force exerted on an indexing shaft 128 that is mounted in cover 124 and is movable from an extended position to an inward, finger release position wherein spring 126 is compressed and finger 122 is withdrawn from a selected indexing cavity 120. With locking finger 122 in its withdrawn position it is apparent that knob 94 can be freely rotated to a position wherein flow channel identification indicia 130 formed on the periphery of knob 94 (FIG. 13) can be viewed through a viewing window 124a formed in cover 124.

Selecting defeat means, here provided in the form of a locking shaft 132 (see FIGS. 10 and 13), is also contained by the cover and, when moved from an extended position into the inward position, prevents the downward movement of finger 122 of the indexing shaft 128 against the urging of spring 126. Accordingly, when locking shaft 132 is in its inward position, finger 122 cannot be moved downwardly and the selecting mixing and dispensing knob 94 cannot be rotated to select a different fluid flow channel.

As best seen in FIG. 5, as the fluid flows outwardly of the selected fluid reservoir due to the urging of the stored energy means 50, the bellows structure 42 that defines that reservoir will be collapsed and, at the same time, connecting member 78 will travel inwardly of housing portion 24. Member 78, which also forms a part of the volume indicator means of the invention is visible through a volume indicator window 137 (FIG. 1) that is provided in portion 24 of the apparatus housing and also comprises a part of the volume indicator means of the invention. Indicia 138, which is provided on indicator window 137, functions to readily indicate to the caregiver the amount of fluid remaining within each of the fluid reservoirs 44.

Figure 10:
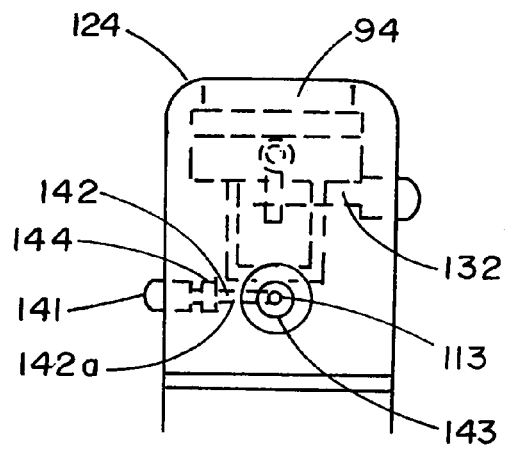
FIG. 10 is a fragmentary, a top plan view of the upper right-hand portion of the apparatus shown in FIG. 1, partly broken away to shown internal construction.

A delivery system safety disabling means, shown here as an operating button 141 and a disabling shaft 142 that is telescopically movable within a passageway 142a formed within cover 124 functions to disable the device and render it unusable. More particularly, as best seen in FIG. 10, shaft 142 has a distal end 143 which, upon insertion of the shaft, will block fluid flow through passageway 113 and on toward the delivery means or administration set 80. As indicated in FIG. 10, retainer 144 normally holds shaft 142 in the retracted position (see FIG. 10).

Fluid coupling O-rings generally designated in the drawings as "O" sealably interconnect the various components (see for example FIGS. 5 and 25).

Turning next to FIGS. 26 through 41A, another form of the multi-channel fluid dispensing apparatus of the present invention is there illustrated and generally designated by the numeral 152. This embodiment of the invention is similar in many respects to that shown in FIGS. 1 through 25 and like numerals are used in FIGS. 26 through 41 to identify like components. The preliminary differences between this latest form of the invention and the earlier described form of the invention, concerns the provision of a different type of stored energy source as well as the provision of a different type of flow control mechanism.

Figure 26:
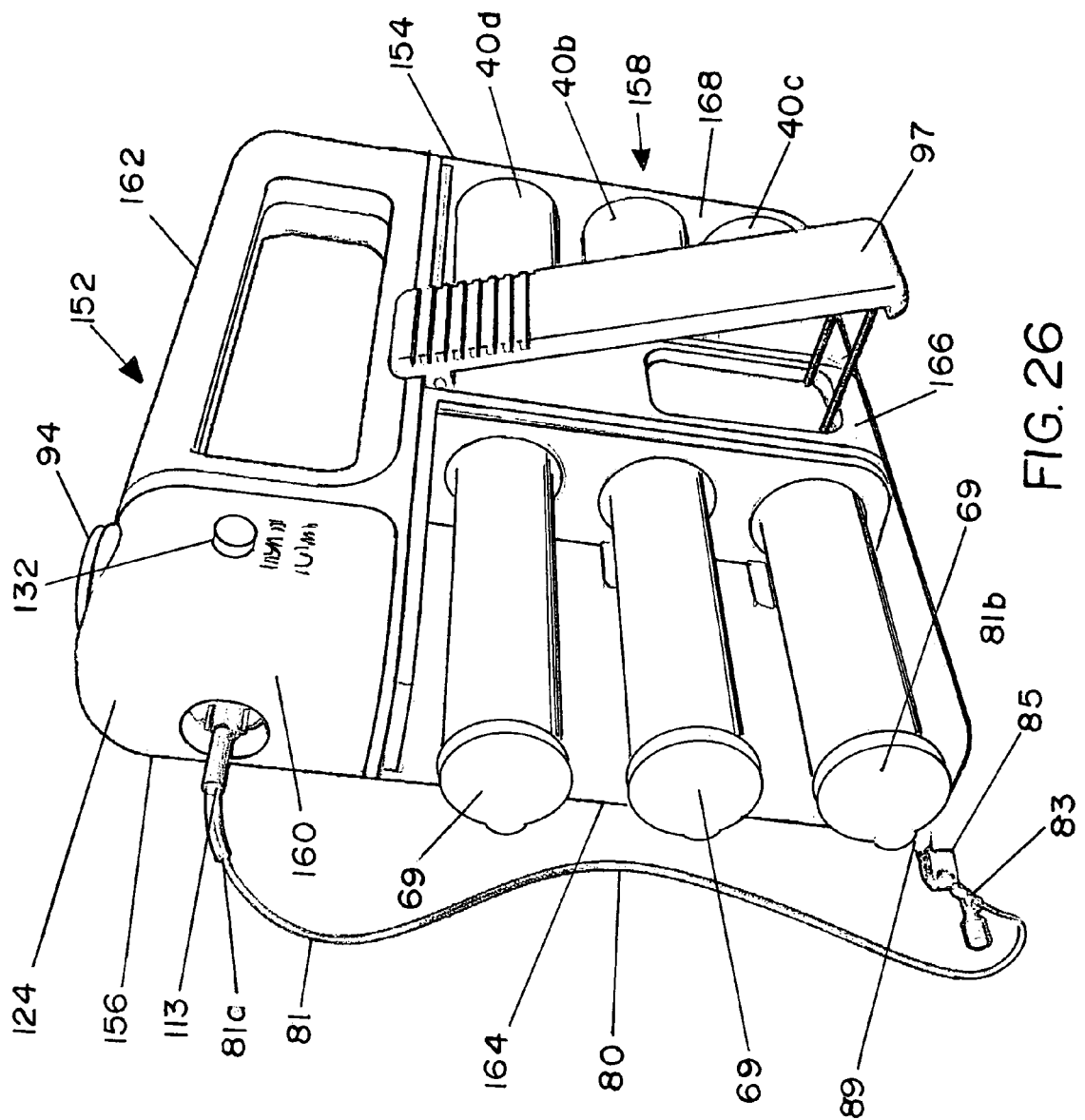
FIG. 26 is a generally perspective view of the backside of an alternate form of the dispensing portion of the multi-channel fluid delivery apparatus of the present invention for dispensing fluids at a uniform rate.
Figure 27A:
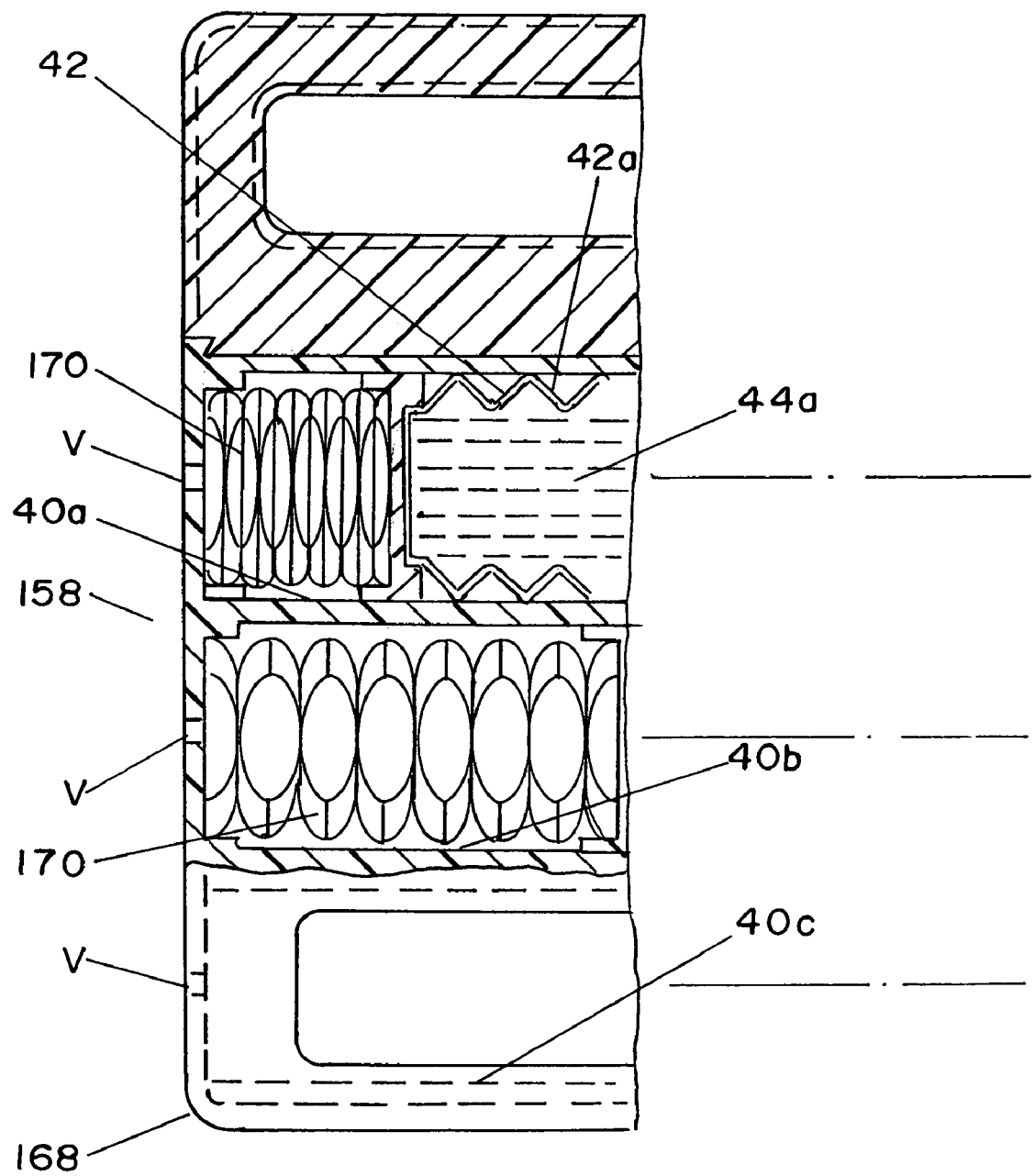
FIGS. 27A, 27B and 27C when considered together comprise a longitudinal cross-sectional view of the fluid delivery apparatus of the invention shown in FIG. 26 (hereinafter collectively referred to as FIG. 27)
Figure 27B:
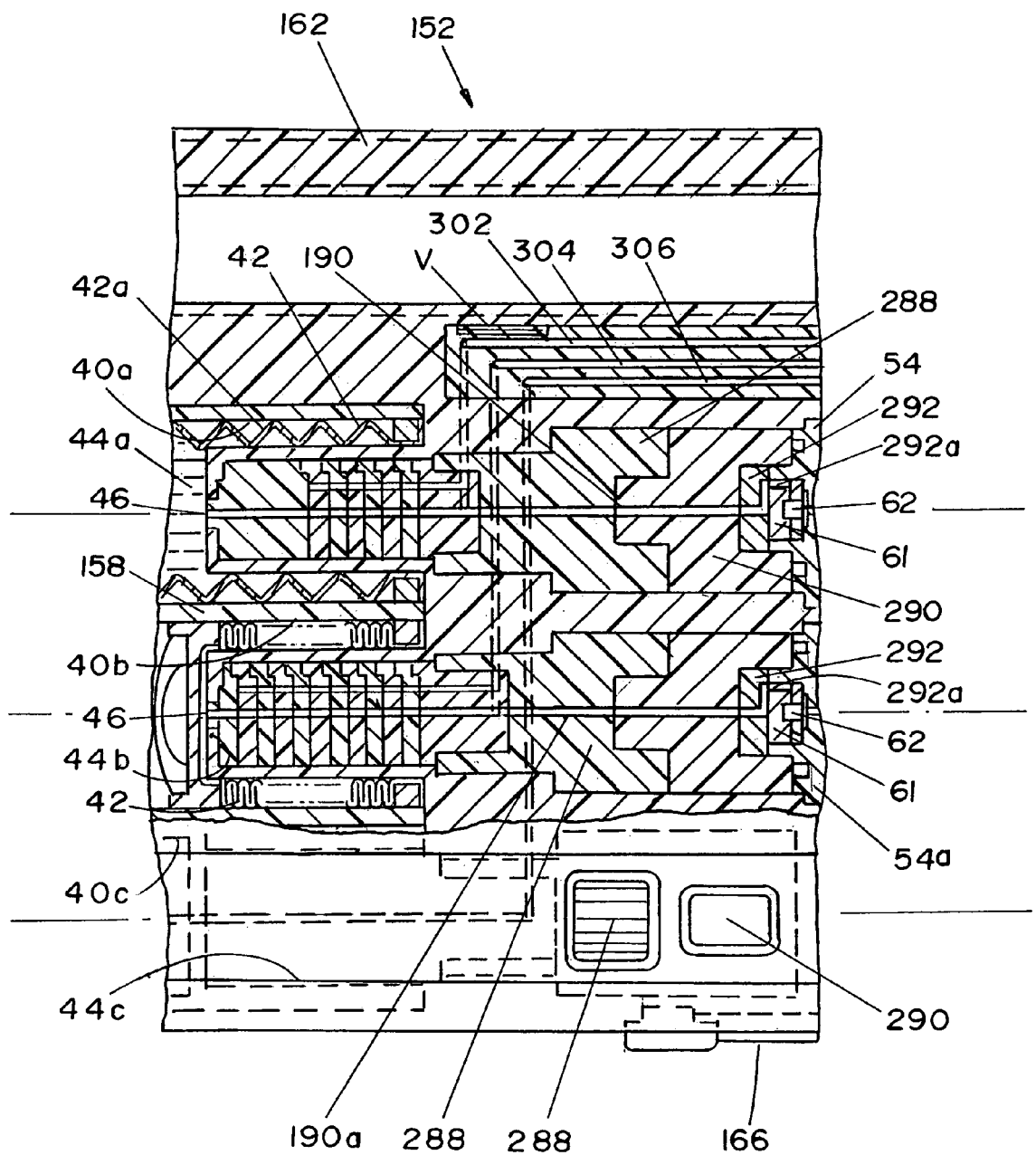
Figure 27C:
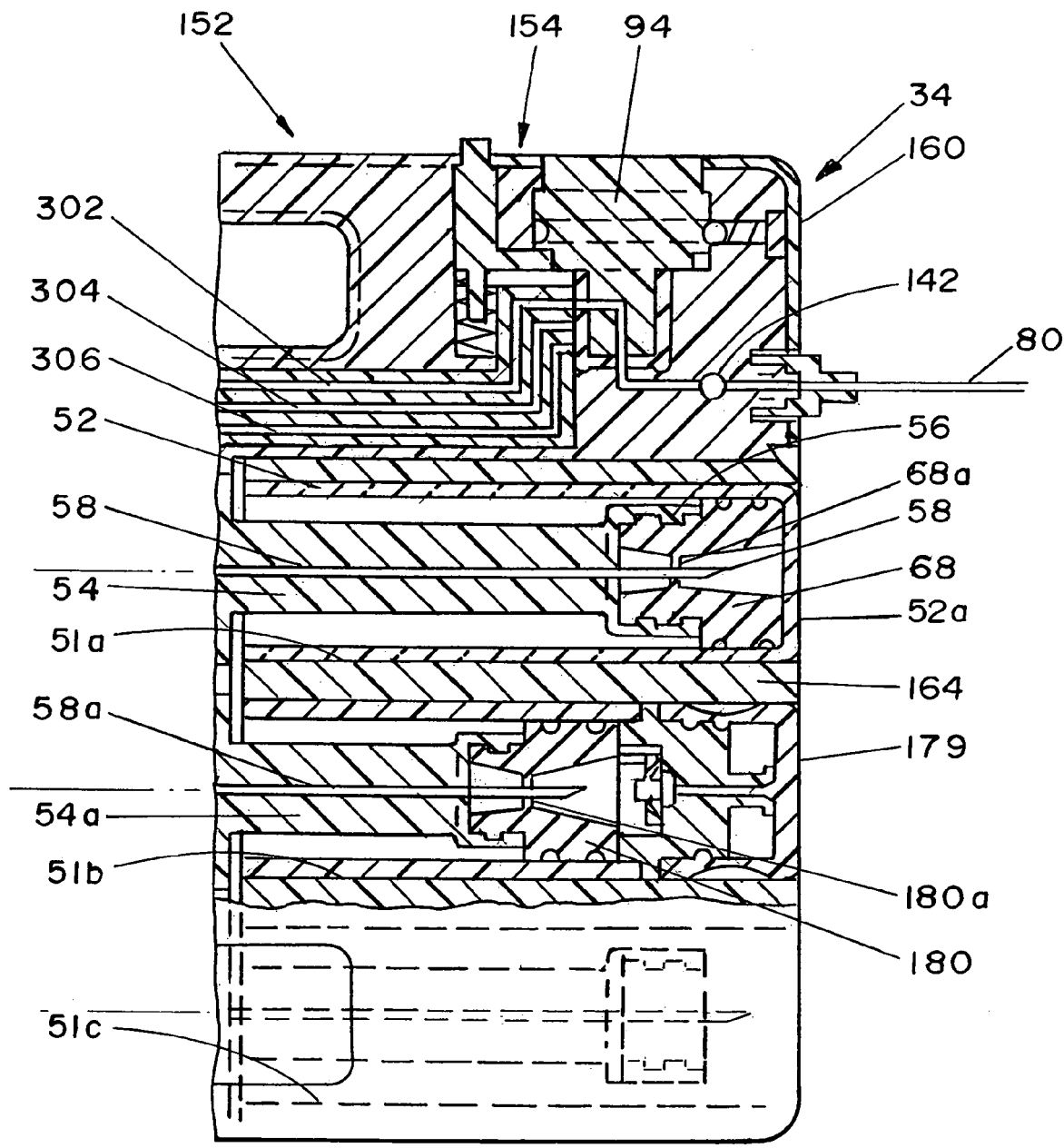

As best seen in FIGS. 26 and 27, the apparatus of this latest form of the invention comprises an outer housing 154 having upper and lower portions 156 and 158 respectively. Upper portion 156 includes a fluid dispensing portion 160 and a handle portion 162. Lower portion 158 comprises a first end, or fill portion 164, a central, or control portion 166 and a second end, or fluid reservoir portion 168.

Considering first the fluid reservoir portion 168, as best seen in FIG. 27, this portion of the apparatus houses three vertically spaced apart fluid reservoir assemblies 40a, 40b and 40c, which are of substantially identical construction and operation to each other and to the fluid reservoir assemblies previously described herein. Disposed within each of the fluid reservoir assemblies 40a, 40b and 40c is an inner, expandable housing 42 having a fluid reservoir 44 provided with an inlet 46 (FIG. 27) for permitting fluid flow into the fluid reservoir. As before, expandable housings 42, which can be constructed from a metal or plastic material, comprise a bellows structure having an expandable and compressible, accordion-like, annular-shaped sidewall 42a, the configuration of which is best seen in FIG. 28.

If the internal materials interface of the bellows structure and other fluid channels or surfaces are not sufficiently compatible with the planned beneficial agent to be delivered, either in terms of its biocompatibility or drug up-take characteristics, application of a one or more selected coating "C" (see for example in FIGS. 13A and 23) through use of a surface modification process is appropriate. This surface modification methodology can tale one of several forms of the type earlier described herein.

Figure 41A:
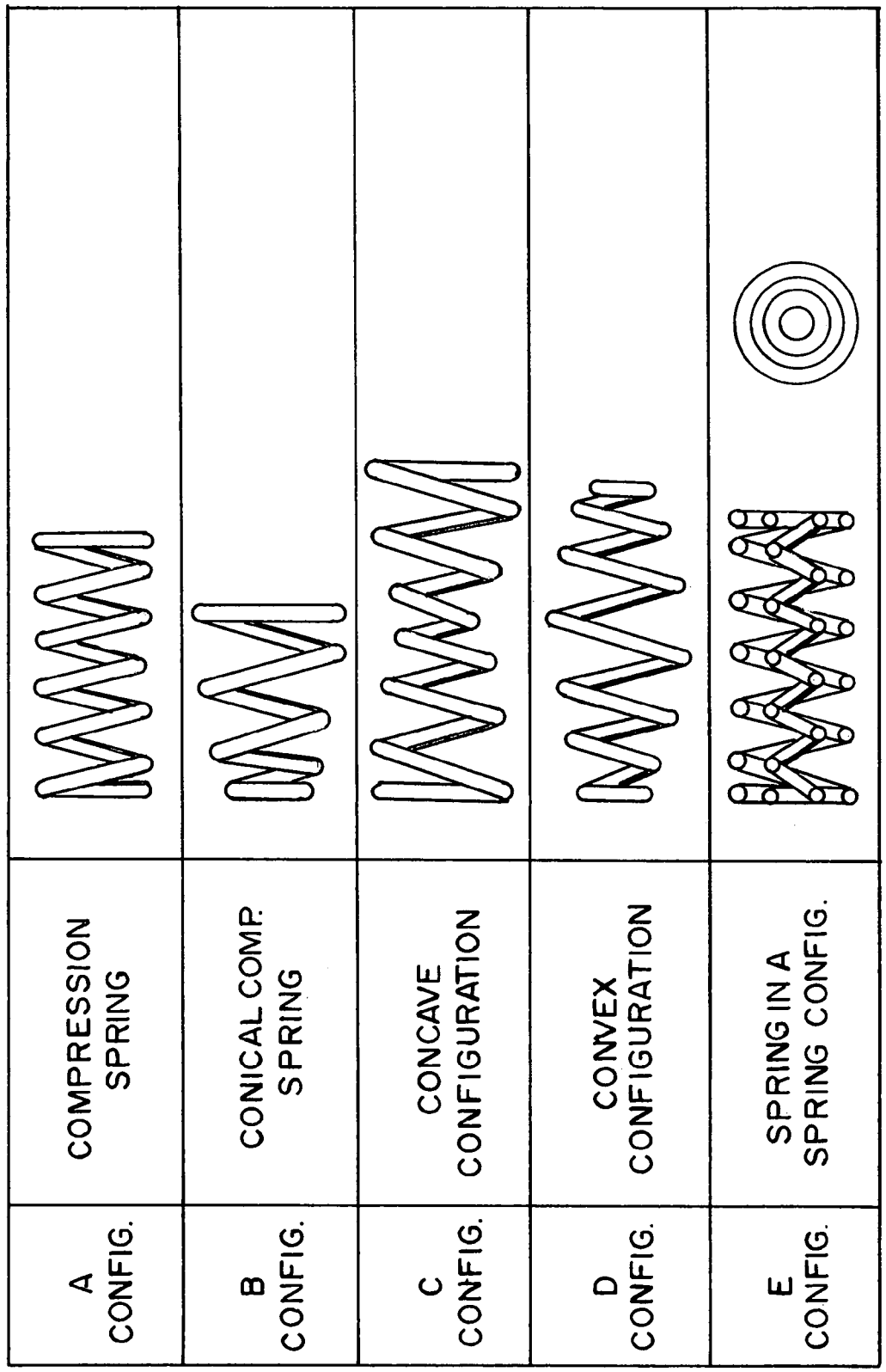
Figure 41C:
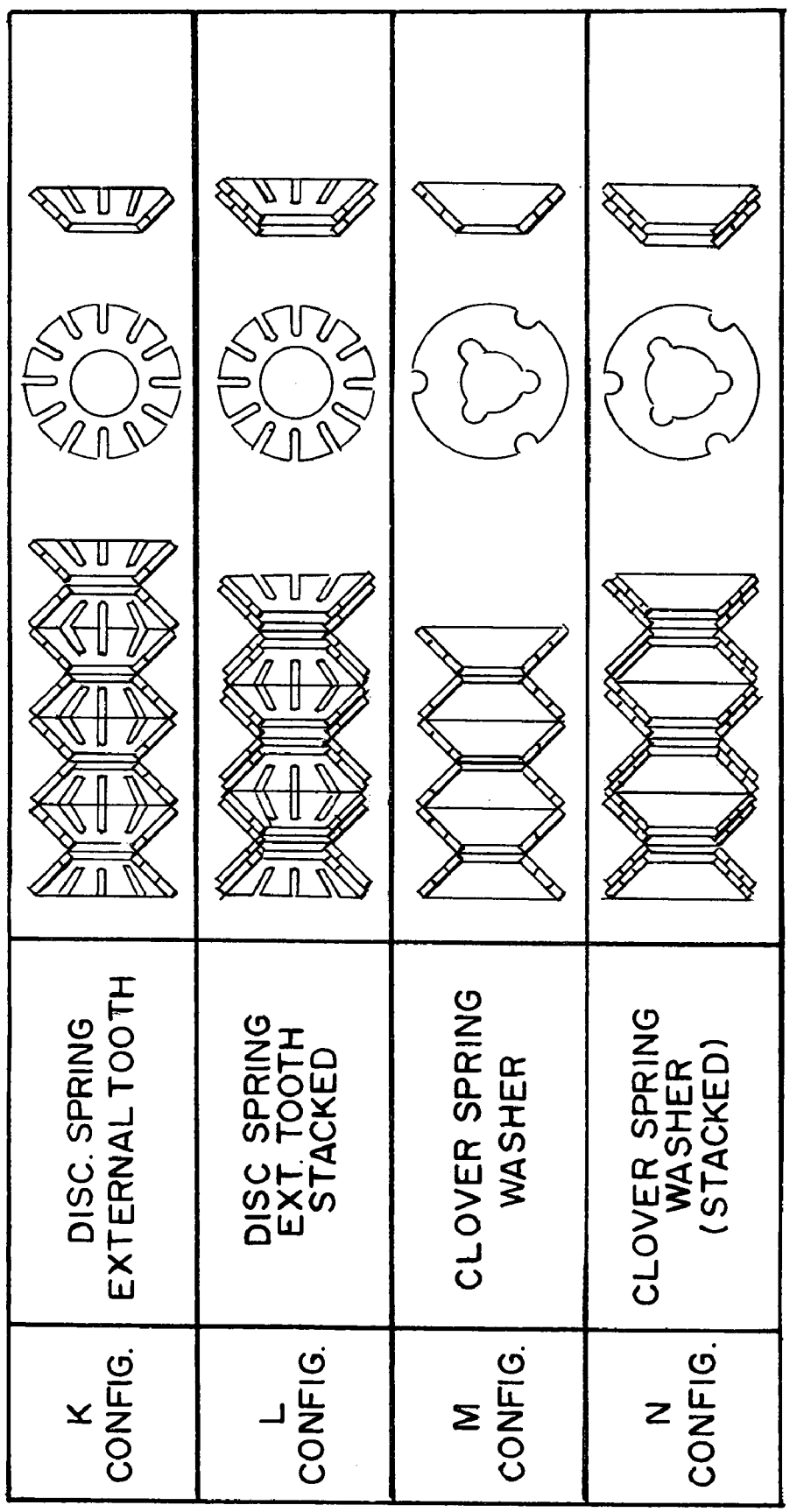
Figure 41D:
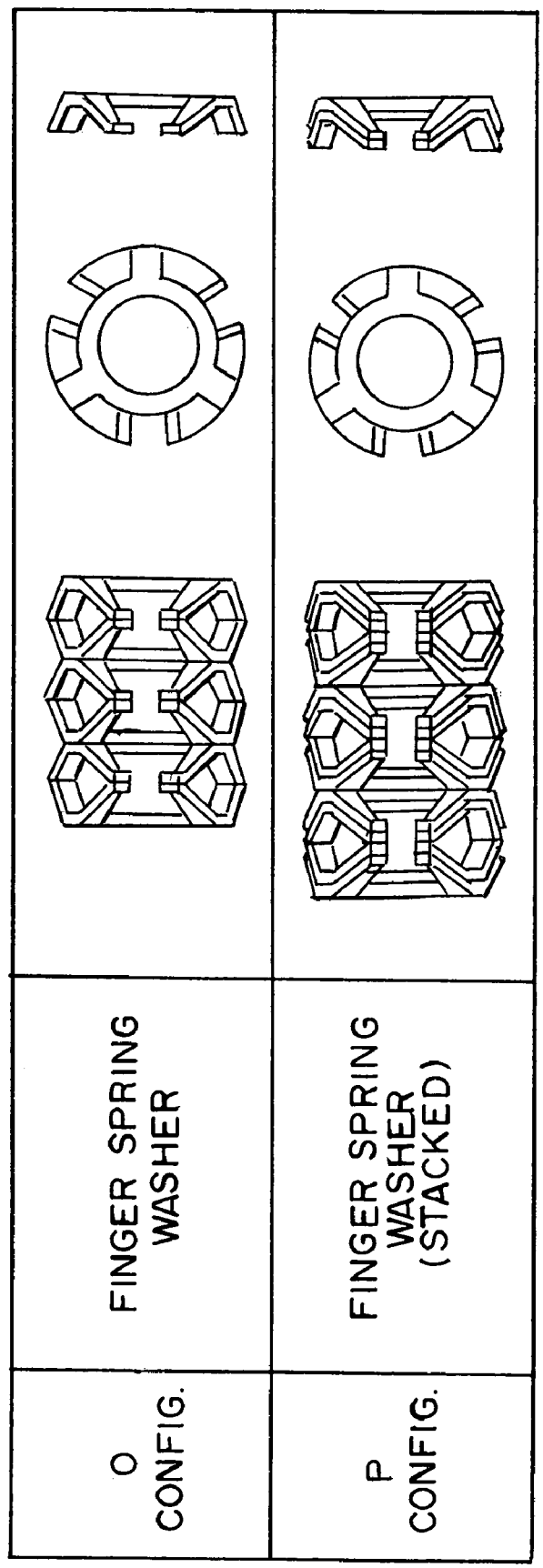

Also disposed within portion 158 of outer housing 34 are the novel stored energy means of the invention for acting upon expandable housings 42 in a manner to controllably collapse the housings so as to cause the fluid contained within the fluid reservoirs 44a, 44b, and 44c thereof to controllably flow outwardly of the housing. In this latest form of the invention, these important stored energy means, the details of construction of which will later be described, comprise compressively deformable, springs 170 that are carried within the second portion 158 of the outer housing in the manner shown in FIG. 27. As illustrated in FIGS. 41 and 41A, and as discussed hereinafter, springs 170 can be constructed in various configurations from a wide variety of materials including various metals and plastics.

In a manner presently to be described, springs 170 are compressed by fluid flowing into the fluid reservoirs and then are controllably expanded to cause fluid flow from the outer housing through the dispensing means of the invention.

Forming an important aspect of the apparatus of the present invention is fill means carried by portion 164 of the outer housing for filling the reservoirs 44 with the fluid to be dispensed. These fill means are similar in construction and operation to those previously described and comprise medicament containing fill vials 52 and 52b that are telescopically received within vertically spaced apart chambers formed in housing 154.

As illustrated in FIG. 15, fill vial 52 includes a body portion 64, having a fluid chamber 66 for containing an injectable fluid. Chamber 66 is provided with a first open end 66a and second closed end 66b. First open end 66a is sealably closed by closure means here provided in the form of an externally threaded elastomeric plunger 68 which is telescopically movable within the vial from a first location shown in FIG. 15 where the plunger is disposed proximate first open end 66a to a second device-fill location where the plunger is disposed proximate second closed end 66b.

As illustrated in FIGS. 29 and 30, the two fill vials 52b, which are of the identical construction shown in these drawings, include a body portion 174, having a fluid chamber 176 for containing an injectable fluid. Chamber 176 is provided with a first end 176a and second end 176b and is closed by a closure member 177. First end 176a is initially, sealably closed by closure means here provided in the form of a threaded closure cap 179 (FIG. 30). Second end 176b is closed by an externally threaded elastomeric plunger 180 which is telescopically movable within the vial from a first location shown in FIG. 30 where the plunger is disposed proximate first end 176a to a second device-fill location where the plunger is disposed proximate second end 176b (FIG. 29). Provided proximate first end 176a is a connector block 182 which includes a luer connector 182a and a cavity portion 182b. Mounted within cavity 182b is a conventional, umbrella type check valve 184. Reservoir 176 can be filled by interconnecting a conventional filling syringe 186 with the luer connector 182a in the manner shown in FIG. 29. As the reservoir fills with the medicinal fluid to be dispensed, plunger 180 will move into the fill position shown in FIG. 29. Check valve 184 functions to prevent fluid flow in a reverse direction toward the luer connector 182a.

After opening aseptic closures 69 (FIG. 26), the fill vials can be inserted into their respective chambers 51a, 51b, and 51c. When fill vial 52 (FIG. 27) is inserted into a chamber 51a, plunger 68 can be threadably interconnected with end 56 of support 54. In so doing, the sharp ends of the elongated needle 58 will pierce the central wall 68a of the elastomeric plunger. Continuous longitudinal movement of the vial into chamber 51a will cause the structural support 54 to move the elastomeric plunger inwardly of the vial chamber in a direction toward the second closed end 66b of the vial. As the plunger is moved inwardly of the vial, the fluid contained within the vial chamber will be expelled therefrom into a hollow elongated needle 58. As illustrated in FIG. 27, the fluid will then flow past umbrella type check valve 62 and into an elongated, central passageway 190 which communicates with the fluid reservoir 44a. Elastomeric umbrella type check valve 62 through a passageway 60a (FIG. 25) will function in a traditional manner to substantially block reverse fluid flow from fluid passageway 190.

In similar manner, the two field fill vials 52b (FIGS. 29 and 30) can be inserted into their respective chambers 51b and 51c. As they are so inserted, the sharp ends of the elongated needles 58a will pierce the central wall 180a of the elastomeric plungers 180. Continuous longitudinal movement of the vials into their respective chambers will cause the structural supports 54a to move the elastomeric plungers inwardly of the vial chambers in a direction toward the second end 176a of the vial. As the plunger is moved inwardly of the vial, the fluid contained within the vial chamber will be expelled therefrom into the hollow elongated needles 58a. As illustrated in FIGS. 25 and 27, the fluid will then flow through passageway 93d, past umbrella type check valves 62 and passageway 60a into an elongated, central passageways 190a which communicates with the fluid reservoirs 44b and 44c. It is to be understood that the vials 52 and 52b can contain the same or different medicinal fluids or diluents.

As the fluid flows into the reservoir portions of the various bellows, the bellows will be expanded from a collapsed configuration into an expanded configuration such as shown in the upper left-hand portion of FIG. 27. As the bellows members expand they will controllably compress spring members 170 (see the upper left-hand portion of FIG. 27). As the various reservoirs fill with fluid, any gases trapped within the reservoirs will be vented to atmosphere via vent means "V" mounted in the housing proximate handle 162 (FIGS. 26 and 27).

Upon opening the fluid delivery path which here comprises a conventional administration set 80 (FIG. 26), the stored energy means, or members 170, will tend to return to their starting configuration thereby controllably urging fluid flow outwardly of a selected reservoir via the flow control means of the invention. In this latest form of the invention, administration set 80, which is identical in construction and operation to that previously described, comprises a part of the dispensing means of the invention for delivering medicinal fluids to the patient. As shown in FIG. 26 administration set 80 is connected to portion 156 of the housing. At the distal end 81b of the set there is provided a luer connector 89 and cap (not shown) both of which are of conventional construction.

As previously discussed, a number of injectable beneficial agents can be contained within liquid vial contains and can be controllably dispensed to the patient including, by way of example, medicaments of various types, drugs, pharmaceuticals, hormones, antibodies, biologically active materials, elements, chemical compounds, or any other suitable material useful in diagnostic cure medication, treatment or preventing of diseases or the maintenance of the good health of the patient.

Forming another very important aspect of the apparatus of this latest form of the invention is the novel flow control means that are carried proximate the central portion of housing 154. These flow control means function to precisely control the rate of fluid flow outwardly from the various fluid reservoirs into the administration set 80 and toward the patient. In the form of the invention shown in FIGS. 26 through 36, the flow control means comprises a plurality of flow control assemblies generally designated in the drawings by the numerals 192, 193 and 194. Each of these flow control assemblies is housed within a tubular ullage means or member 195, best seen in FIG. 37 which functions to insure delivery of all of the fluid contained within the adjacent fluid reservoir. Each of the flow control assemblies is aligned within its receiving ullage by means of all indexing spine 195*a*.

Figure 36:
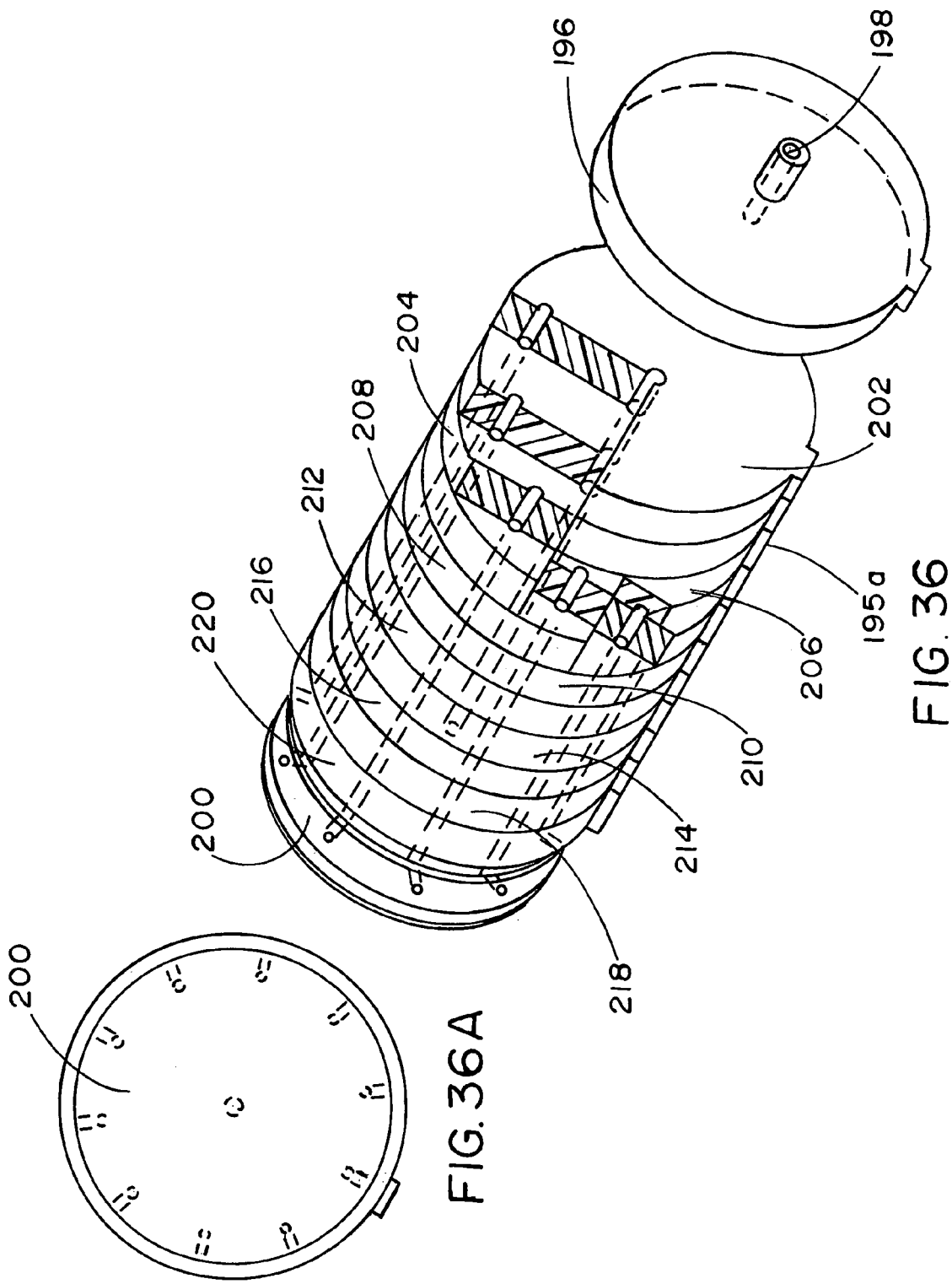
FIG. 36 is an enlarged, generally perspective, exploded view of the flow rate control assembly of the invention.
Figure 39:
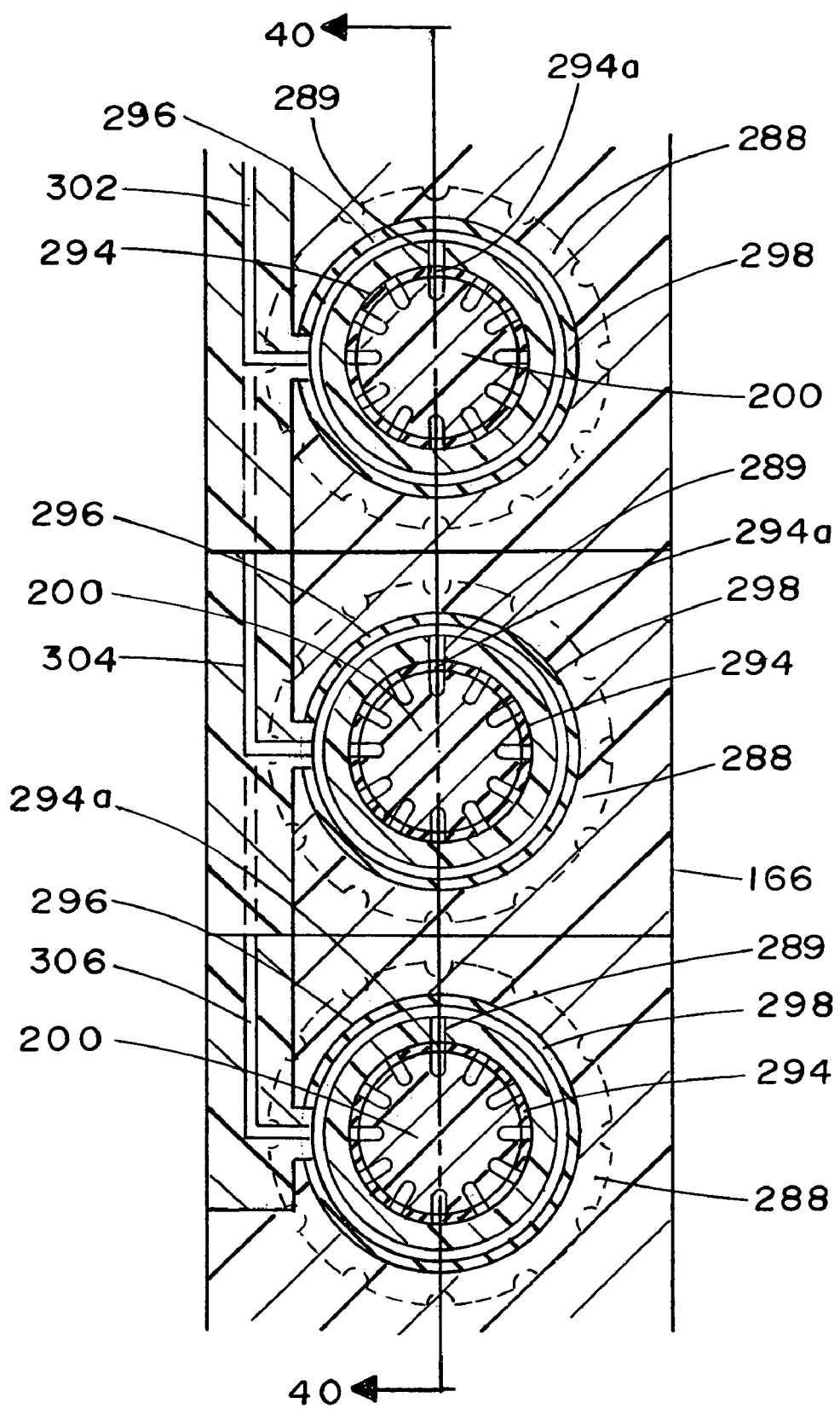
FIG. 39 is a cross-sectional view taken along lines 39—39 of FIG. 27.

Considering first flow control assemblies 192, 193, and 194 these assemblies, which are identical construction each comprise an inlet manifold 196 (FIG. 32) having an inlet port 198 that is in communication with a selected one of the outlets of the here shown fluid reservoirs 44*a*, 44*b* and 44*c* (not shown) (FIG. 27) and an outlet manifold 200 that is interconnected with inlet manifold 196 by means of a plurality of interconnected and indexedly aligned by tab key ways 197 and mating keys flow rate control plates 202, 204, 206, 208, 210, 212, 214, 216, 218 and 220 (see FIGS. 31, 31A and 36). As indicated in FIGS. 35 and 36, outlet manifold 200 has a plurality of circumferentially spaced outlet ports, each of which is in communication with an outlet port of a selected one of the rate control plates. In a manner presently to be described, these circumferentially spaced outlet ports can be selectively brought into communication with the outlet of the apparatus and with the administration line 80 of the administration set via the selector means of the apparatus, the character of which will presently be described.

As best seen by referring to FIGS. 31 and 31A, each of the flow rate control plates is provided with an elongated micro channel of a particular configuration. It is to be understood that as used herein, the terms "microchannel" and "minichannel" are interchangeable. When the rate control plates are substantially sealably interconnected and appropriately registered in the manner shown in FIG. 36, it is apparent that the micro channel formed in each of the rate control plates will cooperate with the adjacent planar surface of the next adjacent rate control plate to form a completed fluid flow control channel through which the fluid can controllably flow. As indicated in the drawings, each of the micro channels is in communication with the inlet port 198 of the inlet manifold 196 and the other end of each of the micro channels is in communication with a selected one of the circumferentially spaced outlet ports provided in the outlet manifold 200. More particularly, as can be seen by referring to FIGS. 31, 31A and 34 of the drawings, outlet 202*a* of rate control plate 202 is in communication with outlet 231 of outlet manifold 200; outlet 204*a* of rate control plate 204 is in communication with outlet 232 of outlet manifold 200; outlet 206*a* of control plate 206 is in communication with outlet 233 of manifold 200; outlet 208*a* of rate control plate 208 is in communication with outlet 234 of outlet manifold 200; outlet 210*a* of rate control plate 210 is in communication with outlet 235 of outlet manifold 200 and outlet 212*a* of rate control plate 212 is in communication with outlet 236 of outlet manifold 200. In similar fashion, outlet 214*a* of rate control plate 214 is in communication with outlet 237 of outlet manifold 200; outlet 216*a* of rate control plate 216 is in communication with outlet 238 of outlet manifold 200; outlet 218*a* of control plate 218 is in communication with outlet 239 of manifold 200 and outlet 220*a* of rate control plate 220 is in communication with outlet 240 of outlet manifold 200.

With the construction of the flow control means shown in the drawings, and by way of example, fluid will flow from reservoir 44*b* into inlet port 198, through a fitter member 243 (FIG. 31) and thence into micro channel 244 formed in plate 202. By controlling the length., width., depth and configuration of the micro channel 244, the rate of fluid flow flowing outwardly or outlet 202*a* can be precisely controlled. In a manner presently to be described, the fluid will then flow onwardly toward the administration set via the flow regulation means of the invention. It is to be understood that micro channel 244 can take various forms and can be of varying length, width and depth to precisely control the rate of fluid flow therethrough.

Fluid flowing through inlet port 198 will also flow into micro channel 246 formed in rate control plate 204. Once again, depending upon the length, width and depth of micro channel 246, the rate of fluid flowing outwardly of outlet 204*a* can be precisely controlled. In similar manner, fluid flowing through inlet port 198 (FIG. 31) will fill micro channel 248 formed in rate control plate 206, will fill micro channel 250 formed in plate 208, will fill micro channel 252 formed in rate control plate 210, will fill rate control micro channel 254 formed in rate control plate 212, will fill rate control micro channel 256 formed in rate control plate 214, will fill rate control micro channel 258 formed in rate control plate 216, will fill flow control micro channel 260 formed in rate control plate 218 and will fill rate control micro channel 262 formed in rate control plate 220. After flowing through the rate control micro channels formed in the various indexedly aligned rate control plates, the fluid will flow onwardly toward outlet manifold 200 and will fill the stub passageways 265 formed therein (FIGS. 34 and 35). The rate of flow of fluid flowing outwardly of each of the outlet ports of the various rate control plates will, of course, depend upon the individual physical parameters and the configuration of the individual rate control micro channels formed in the rate control plates. In similar maimer, fluid will flow from reservoir 44*c* through the rate control plates that makeup assemblage 192, which assemblage is housed within the lowermost bellows assembly of the apparatus (FIG. 27).

Considering next flow control assembly 194, as indicated in FIG. 37, which is an enlarged view of the area designated in FIG. 27 by the numeral 37, assembly 194 is similar in construction and operation to the previously described flow control assemblies 192 and 193, but incorporates a fewer number of cooperating rate control plates. More particularly, as illustrated in FIG. 37, flow control assembly 194 comprises an inlet manifold 266 of increased length having an inlet port 268 that is in communication with outlet 269 of the fluid reservoir 44*a* (FIG. 27) and an outlet manifold 270 that is interconnected with inlet manifold 266 by means of a plurality of interconnected flow rate control plates 272, 274, 276, 278, 280 and 282 (see FIG. 37). As indicated in FIG. 37, outlet manifold 270 has a plurality of circumferentially spaced outlet ports, each of which is in communication with an outlet port of a selected one of the rate control plates. In a manner presently to be described, these circumferentially spaced outlet ports can be selectively brought into communication with the outlet of the apparatus and with the administration line 80 of the administration set via the selector means of the apparatus, the character of which will presently be described.

As in the earlier described embodiment of the invention, each of the flow rate control plates is provided with all elongated micro channel of a particular configuration. When the rate control plates are assembled in the mauler shown in FIG. 37, the micro channel formed in each of the rate control plates will cooperate with the next adjacent rate control plate to form a completed fluid flow control channel through which the fluid can controllably flow. As indicated in the drawings, each of the micro channels is in communication with the inlet port 268 of the inlet manifold 266 and the other end of each of the micro channel is in communication with a selected one of the circumferentially spaced outlet ports provided in the outlet manifold 270.

Also forming a part of the flow control means of this latest form of the invention are identically constructed thumbwheels 288 (FIG. 27), which are selectively connected to the outlet manifolds of the apparatus flow control members and identically constructed indicator drums 290 which are connected to the thumbwheels. Additionally, the flow control means further comprises bonded fluid connectors 292 that are mounted within indicator drums 290. As indicated in FIGS. 27 and 27A, fluid connectors 292 function to interconnect, via passageways 292a, the flow passageways of the elongated needles 58 and 58a of the fill means of the invention with the elongated passageways 190 and 190a which carry the medicinal fluids to reservoir 44a. In this latest form of the invention, the flow control means also includes selection, mixing and dispensing means, shown here as comprising a knob 94, which is identical in construction in operation to that previously described and that is rotatably carried with in housing portion 156 in the manner best seen in FIG. 27. As will presently be described, mixing and dispensing knob 94 can be manipulated by the caregiver to select the medicinal fluid or fluid mixture that is to be delivered to the patient.

Figure 40:
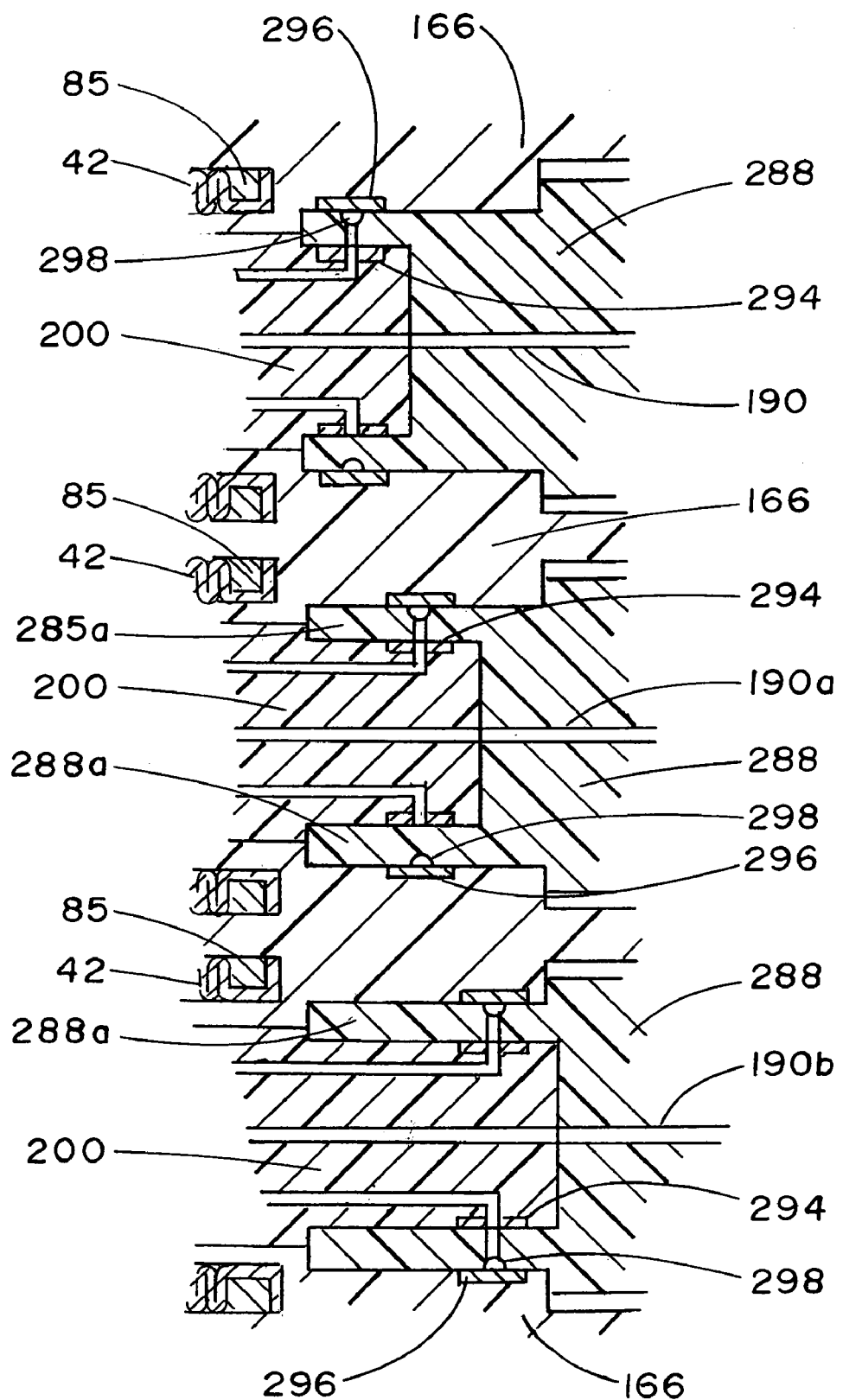
FIG. 40 is a cross-sectional view taken along lines 40—40 of FIG. 39.

Referring particularly to FIG. 40, each of the thumbwheels 288, which comprise a part of the selector means of the invention, are sealably connected to their respective outlet manifolds and are rotatable with respect thereto. This novel selector means of the invention functions to control the flow of fluid from a selected outlet manifold toward the administration set 80. More particularly, as illustrated in FIGS. 40, 40A, and 40B the rearwardly extending flange portion 288a of each of the thumbwheels circumscribes a portion of a selected outlet manifold 200 and is provided with a radially extending fluid passageway 265 and circumferentially extending, apertured elastomeric band 294 which prevents fluid leakage between then the outlet manifold and the flange 288a. Portion 166 of the housing is also provided with circumferentially extending, elastomeric band 296 to prevent leakage between the flange of the central portion 166 of the housing.

As illustrated in FIGS. 40A and 40B the flange portion 288a of each of the thumbwheels is provided with a circumferentially extending recessed flow channel 298 which can be placed in communication with a selected stub passageway 265 of outlet manifolds 200 upon rotation of the thumbwheel. As indicated in FIGS. 40A and 40B, each of the elastomeric bands 296 has a single passageway 296a that is in alignment with one of the fluid transfer outlet passageways 302, 304, or 306 (in this case passageway 304) formed in the first portion 166 of the housing (see also FIG. 27). With this construction, when the thumbwheel is rotated to a positions such as that illustrated in FIG. 40B, wherein outlet 304 of the outlet manifold is in alignment both with passageway 298 and with single passageway 294a formed in the elastomeric band 294, fluid can flow from that outlet into passageway 304 and thence to the dispensing means or administration set 80. The rate at which the fluid flows toward the administration set depends, of course, upon which rate control plate outlet is in communication with the stub passageways 265 (FIG. 40a). For example, with the thumbwheel 288 in the position shown in the upper portion of FIGS. 39 and 40, it is to be observed that the fluid flowing toward the administration set is flowing from outlet 240 of the center outlet manifold, through passageway 298 in the flange 288, through passageway 294a in elastomeric band 294 and into channel 298. The rate of fluid flow is, of course, determined by the configuration of rate control micro channel 262 of rate control plate 220 (see FIGS. 31, 31A and 34). Similarly, with the thumbwheel 288 in the position shown in the lower portion of FIGS. 39 and 40, it is to be observed that the fluid flowing toward the administration set is flowing from outlet 239 of the lower outlet manifold, through passageway 298 in flange 288, through passageway 294a in band 294 and into channel 298. In this case, the fluid will flow at a rate determined by the configuration of rate control micro channel 260 of rate control plate 218 (see FIGS. 31, 31A and 34).

Referring once again to FIGS. 41 and 41A, the various types of springs suitable for use as the stored energy source of the invention are there illustrated and described. By way of background, springs are unlike other machine/structure components in that they undergo significant deformation when loaded—their compliance enables them to store readily recoverable mechanical energy.

With respect to the specific spring configurations shown in the drawings, the following discussion amplifies the descriptive notations in the drawings.

Compression Springs:

Compression springs are open-wound helical springs that exert a load or force when compressed. Depending on the force-extension wave form desired, they may be conical or taper springs, barrel or Convex hourglass or concave, variable pitch, or standard cylindrical in shape. The ends can be closed and ground, closed but unground, open and unground and supplied in alternate lengths. They also Can include a configuration where a second compression spring of similar or different performance characteristics which can be installed inside the inside diameter of their first compression spring, i.e., a spring in a spring.

Many types of materials can be used in the manufacture with compression springs including: Commercial Wire (BS5216 HS3), Music Stainless Steel, Phosphur Bronze, Chrome Vanadium, Monel 400, Inconel 600, Inconel X750, Nimonic 90: Round wire, Square and Rectangular sections are also available. Exotic metals and their alloys with special properties can also be used for special and applications; they include such materials as beryllium copper, beryllium nickel, niobium, tantalum and titanium.

Compression springs can also be made from plastic including all thermoplastic materials used by custom spring winding service providers. Plastic springs may be used in light-to-medium duty applications for quiet and corrosion-resistant qualities.

Wave Spring:

Multi wave compression springs 170, here shown in FIGS. 27 and 41 tab F, are readily commercially available from sources, such as the Smalley Company of Lake Zurich, Ill. Such springs operate as load bearing devices. They can also take up play and compensate for dimensional variations within assemblies. A virtually unlimited range of forces can be produced whereby loads built either gradually or abruptly to reach a predetermined working height. This establishes a precise spring rate in which load is proportional to deflection, and can be turned to a particular load requirement.

Typically, a wave spring will occupy an extremely small area for the amount of work it performs. The use of this product is demanded, but not limited to tight axial and radial space restraints.

Disc Springs:

Disc springs are shown in FIG. 41 TAB G through P, are conically shaped annular discs (some with slotted or fingered configuration) which when loaded in the axial direction, change shape. In comparison to other types of springs, disc springs produce small spring deflections under high loads and, accordingly, can be structured to provide an extended level of defection. Some examples of the disc-shaped compression springs include a single or multiple stacked, Belleville washer configuration as shown more specifically in FIG. 41, TABS G and H, and depending on the requirements of the design (flow rate over time including bolus opportunity) one or more disc springs can be used of alternate individual thicknesses. Alternate embodiments of the basic disc spring design in a stacked assembly can be also utilized including specialty disc springs similar to the Belleville configuration called K disc springs manufactured by Adolf Schnorr GM8H of Singelfingen, Germany, as well as additional forms manufactured by Christian Bauer GMBH of Welzheim, Germany.

Disc springs combine high energy storage capacity with low space requirement and uniform annular loading. They can provide linear or nonlinear spring loadings with their unique ability to combine high or low forces with either high or low deflection rates. They can also be preloaded and under partial compression for an extended duration in the design application.

All these attributes, and more, come from single-component assemblies whose nontangle features (when compared to wirewound, compression springs) also made them ideal for automatic assembly procedures.

With respect to the various springs discussed in the preceding paragraphs, it is to be understood that many alternate materials can be used in the design and application of disc springs and include carbon steel, chrome vanadium steel, stainless steel, heat resistant steels, and other special alloys such as nimonic, inconel, and beryllium copper. In some special applications, plastic disc springs designs can be used.

It should be further observed that, in comparison to other types of springs, a single disc spring will produce a small spring deflection under a high load. The ability to assemble disc springs into disc spring stacks overcomes this particular limitation when a greater extension is required When disc springs are arranged in parallel (or nested), the load increases proportionate to the number of springs in parallel, while when disc springs are arranges in series (alternately) the travel will increase in proportion to the number of springs serially arranged. These assembly methods may be combined in use.

One special feature of the disc spring is, undoubtedly, the fact that the load/deflection characteristic curve can be designed to produce a wide variety of possibilities. In addition, in some arrangements, practically linear load/deflection characteristic curve or regressive characteristics can be achieved and even disc springs which exhibit increasing spring deflection while the corresponding disc spring load is decreasing are readily available (FIG. 41A).

Slotted disc springs (FIG. 41 Tabs I through P) present a completely different case. Slotting changes the load/deflection characteristic of the single disc spring, providing larger spring deflections for greatly reduced loads. The slotted part is actually functioning as a series of miniature cantilever arms. In some cases a stacked, slotted disc spring configuration, as shown in the clover dome design, will also produce a non-linear, stress strain curve with a pronounced flat region (force/deflection). Application and use of this type of spring operating in this region will provide a near constant force between 15% and 75% of compression. It is to be observed that the change in spring force has a direct relationship on the chamber pressure of the reservoir 44 and on the tolerance of the resulting system flow rate performance.

Referring to FIGS. 42 through 47, still another form of the multi-channel fluid dispensing apparatus of the present invention is there illustrated and generally designated by the numeral 312. This embodiment of the invention is similar in many respects to that shown in FIGS. 26 through 41 and like numerals are used in FIGS. 42 through 47 to identify like components. The primary differences between this latest form of the invention and the earlier described form of the invention concerns the provision of a different type of stored energy source, namely a constant force spring type energy source.

Figure 42:
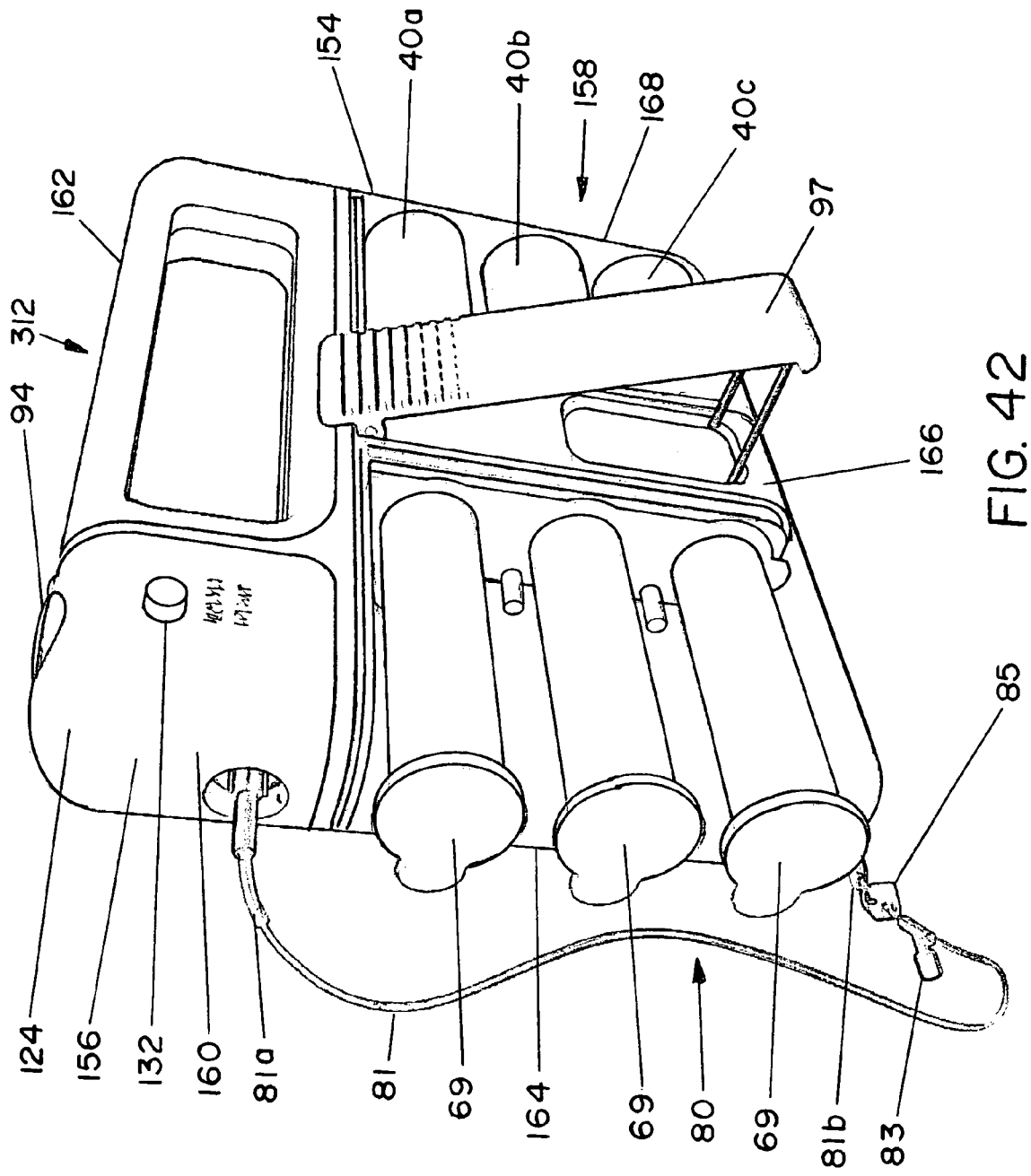
FIG. 42 is a generally perspective view of the back side of yet another form of the dispensing portion of the multi-channel fluid delivery apparatus of the present invention for dispensing fluids at a uniform rate.
Figure 43A:
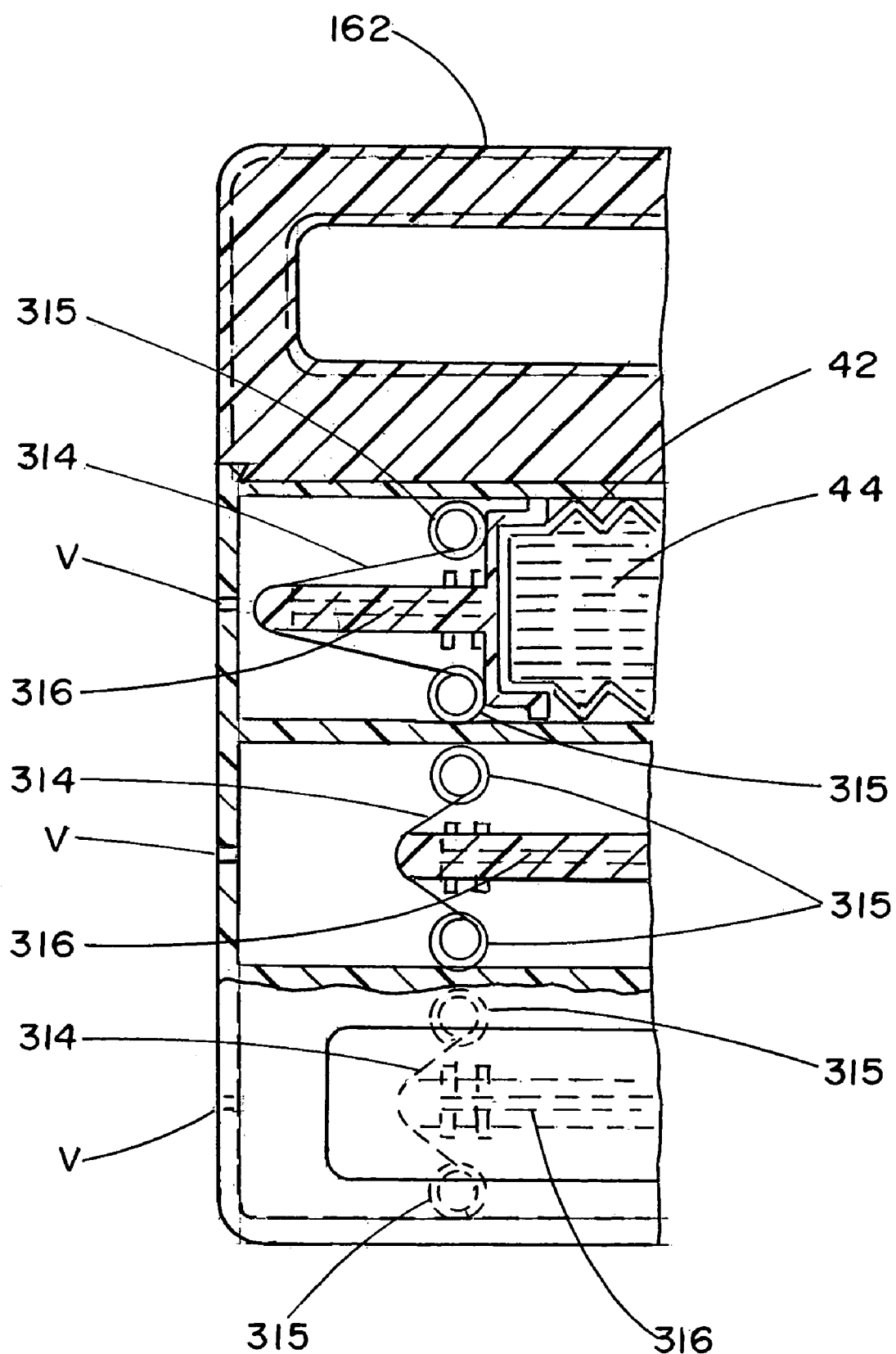
FIGS. 43A, 43B and 43C when considered together comprise a longitudinal cross-sectional view of the fluid delivery apparatus of the invention shown in FIG. 42 (hereinafter collectively referred to as FIG. 43)
Figure 43B:
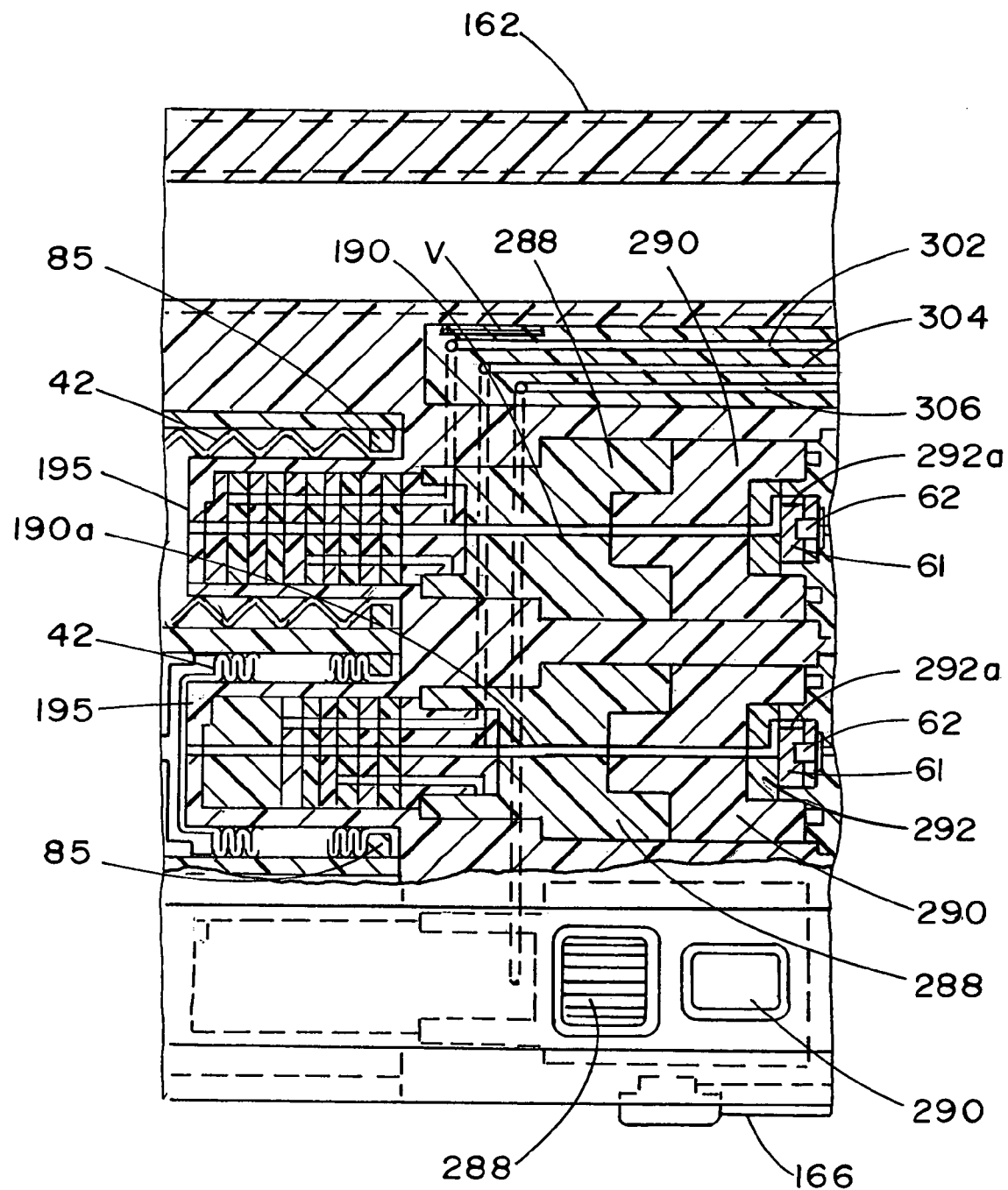
Figure 43C:
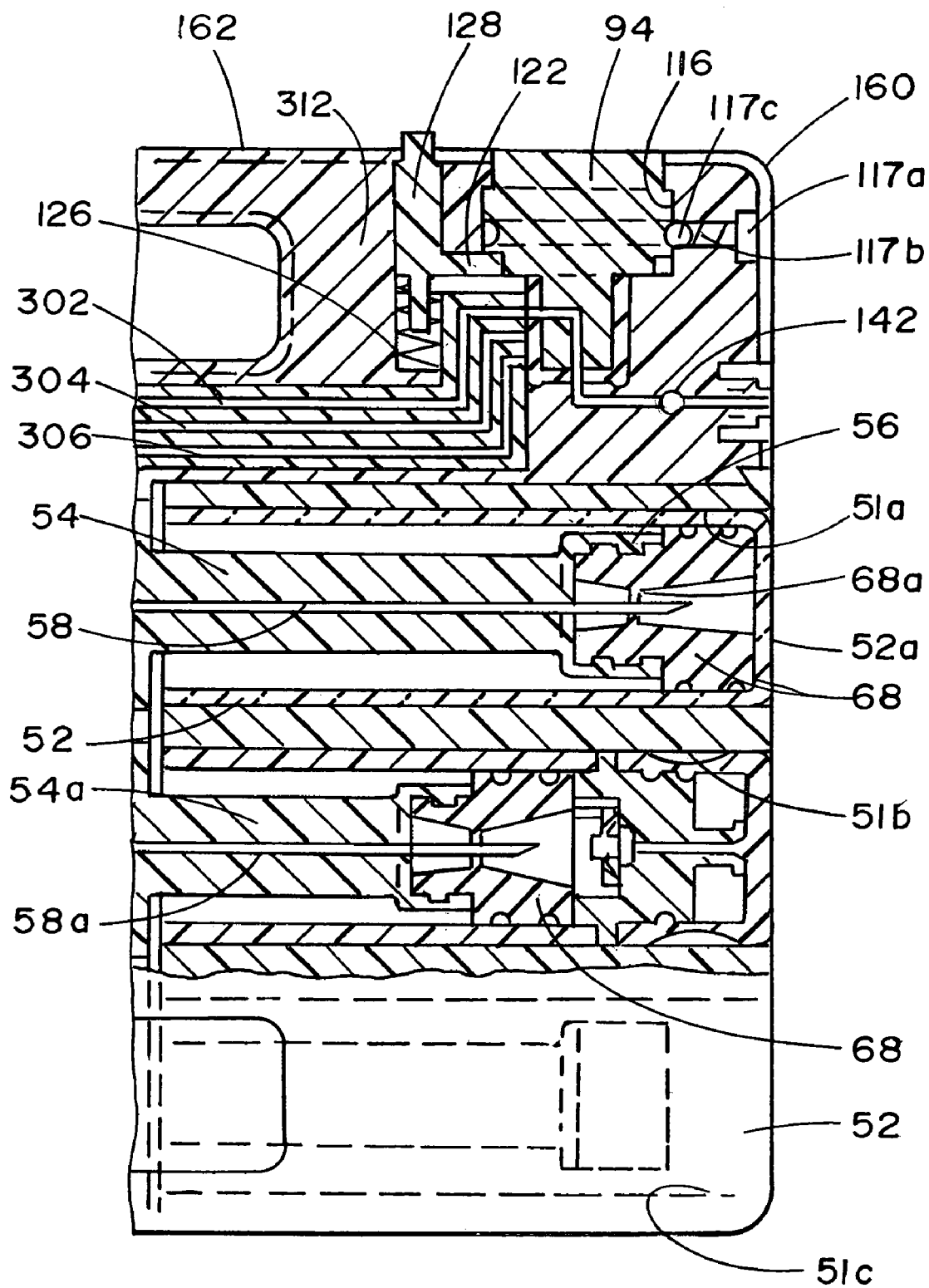
Figures 44, 44A:
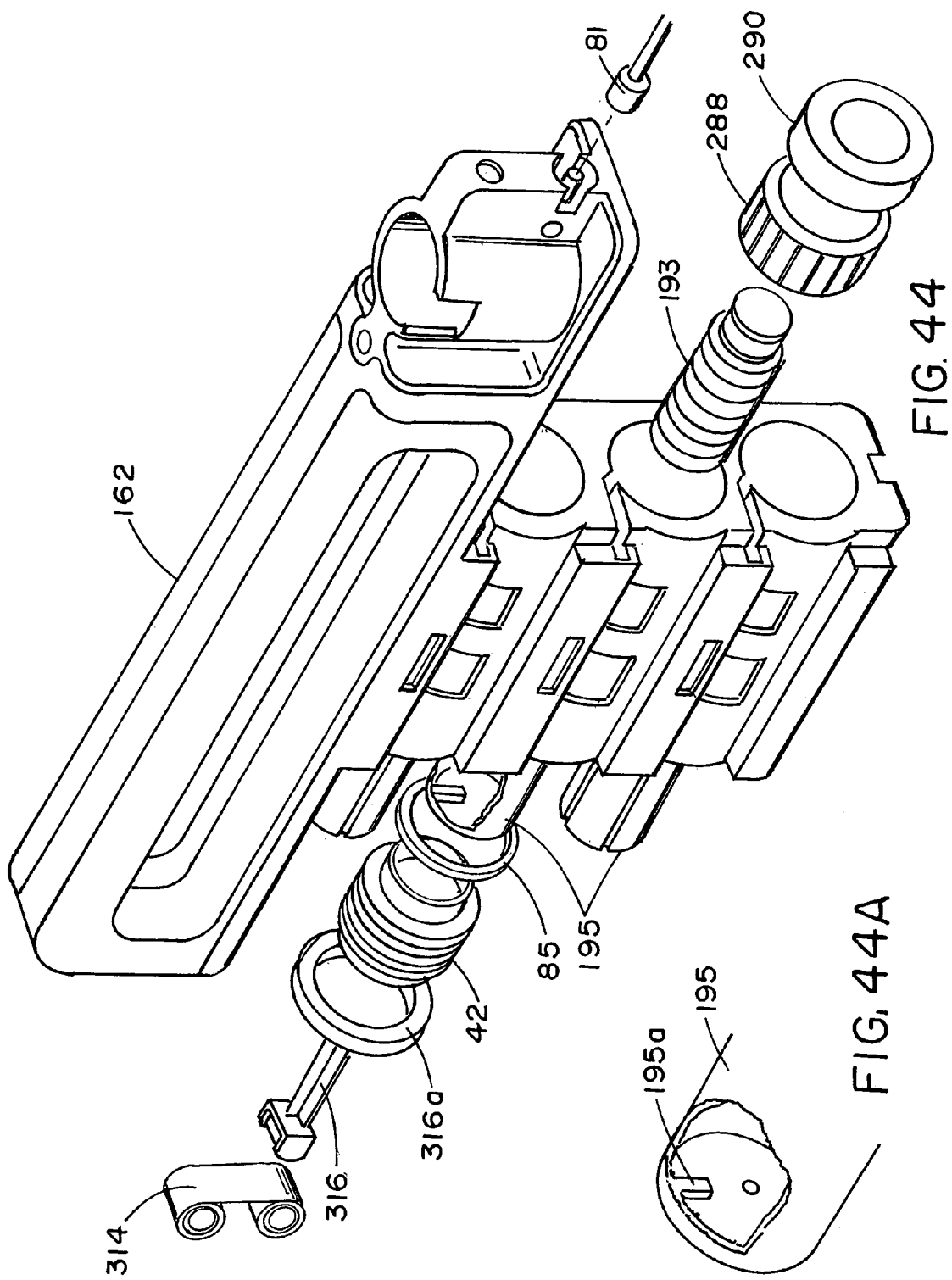
FIG. 44 is a generally perspective, exploded view of the primary operating components of the apparatus of the invention shown in FIG. 42.
FIG. 44A is a generally perspective, fragmentary view of the ullage portion of the apparatus of the invention shown in FIG. 44 for insuring the expulsion of substantially all of the fluid from the fluid reservoirs of the apparatus.
Figure 45:
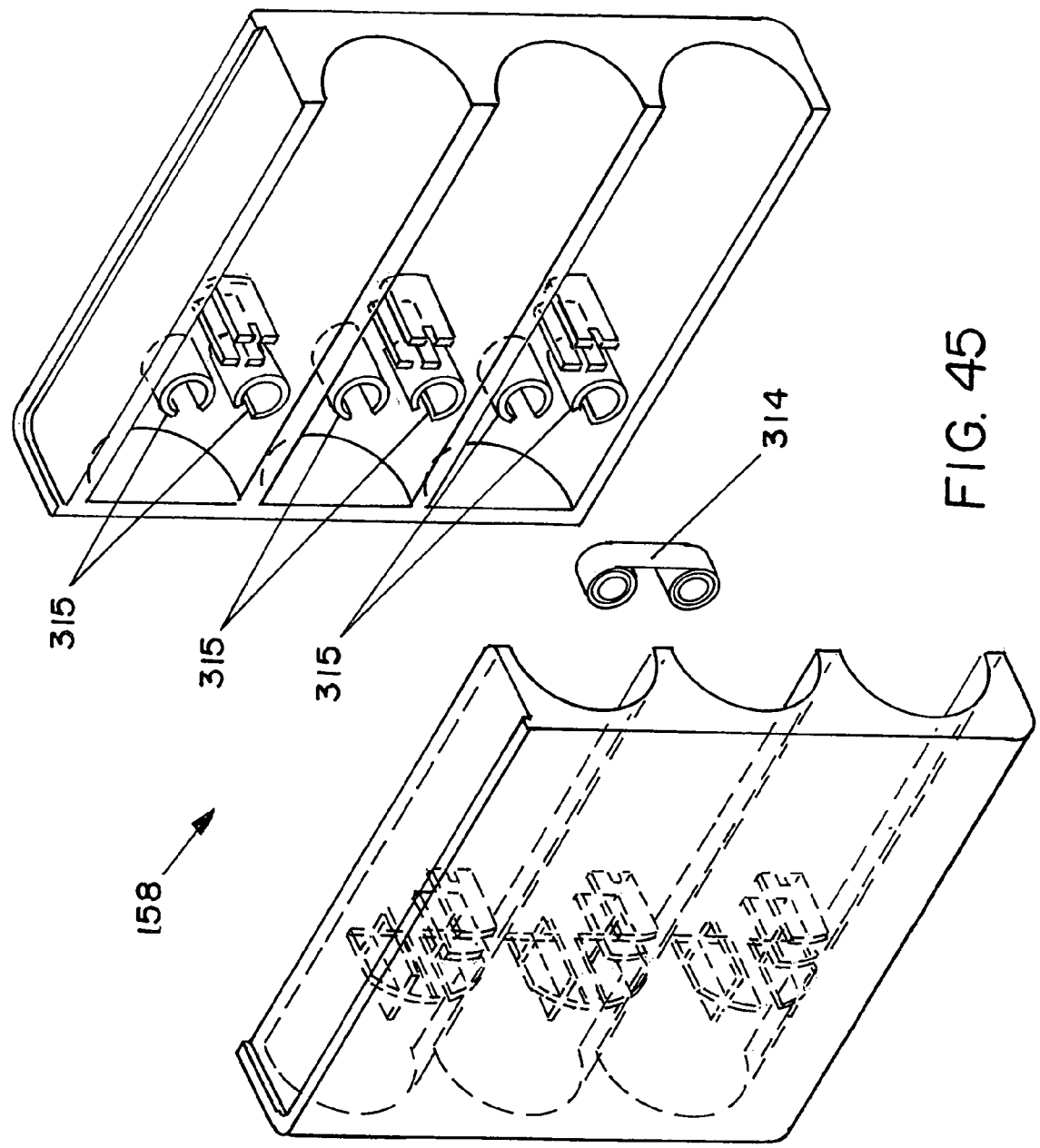
FIG. 45 is a generally perspective, exploded view of the snap together, rear portion of the housing of the apparatus shown in FIG. 42.
Figure 46:
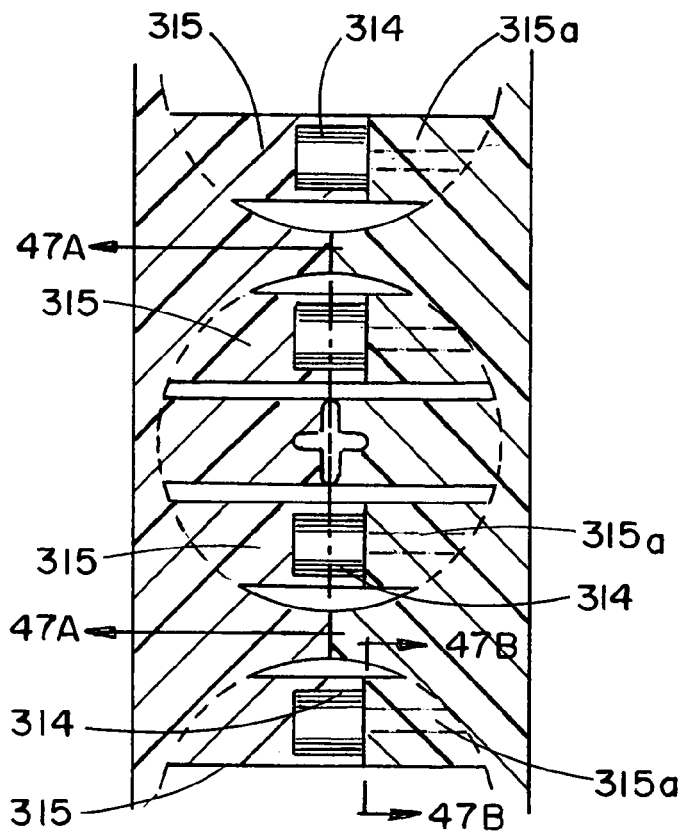
FIG. 46 is an enlarged cross-sectional view of the central, left-hand portion of the apparatus shown in FIG. 43, further illustrating the positioning of the constant force spring stored energy means of this latest form of the invention.
Figure 47A:
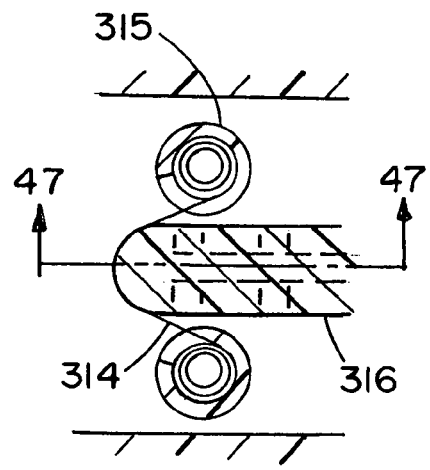
FIG. 47A is a view taken along lines 47A—47A of FIG. 46.
Figure 47B:
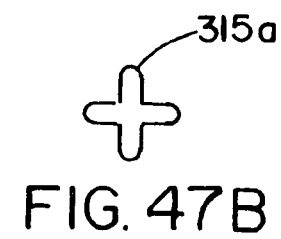
FIG. 47B is a view taken along lines 47B—47B of FIG. 46.
Figure 47:
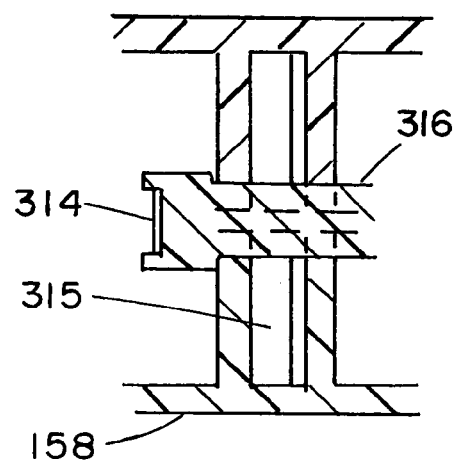
FIG. 47 is a cross-sectional view taken along lines 47—47 of FIG. 46.

As shown in FIGS. 42 and 43, the apparatus of this latest form of the invention comprises an outer housing 154 having upper and lower portions 156 and 158 respectively. Upper portion 156 includes a fluid dispensing portion 160 and a handle portion 162. Lower portion 158 of the housing comprises a first end, or fill portion 164, a central, or control portion 166 and a second end, or fluid reservoir portion 168.

Considering first the fluid reservoir portion 168 (FIGS. 42 and 43), as before, this portion of the apparatus houses three vertically spaced apart fluid reservoir assemblies 40*a*, 40*b* and 40*c*, which are of substantially identical consumption and operation to each other and to the fluid reservoir assemblies previously described herein. Disposed within each of the fluid reservoir assemblies 40*a*, 40*b* and 40*c* is an inner, expandable housing 42 having a fluid reservoir 44 provided with an inlet 46 (FIG. 43) for permitting fluid flow into the fluid reservoir.

Also disposed within second portion 168 of the outer housing are the novel stored energy means of the invention for acting upon expandable housings 42 in a manner to controllably collapse the expandable housings so as to cause the fluid contained within the fluid reservoirs 44 to controllably flow outwardly of the housing. In this latest form of the invention, these important stored energy means comprises constant force spring members 314 that are carried within the second portion 168 of the outer housing. Spring members 314 are first extended in the manner shown in the upper left-hand portion of FIG. 43 by fluid flowing into the reservoir designated as 44 and then controllably retracted to cause fluid flow from the outer housing through the dispensing means of the invention. Stored energy members or constant force springs 314, which are a special variety of extension spring, are readily commercially available from several sources, including Barnes Group Inc. of Bristol, Conn.; Stock Drive Products/Sterling Instrument of Hyde Park, N.Y. and Walker Corporation of Ontario, Calif. Constant force extension springs 314 are basically a high stress, long deflection devices that offers great advantages when used in applications such as the present application where very low or zero gradient is desired, where space is a factor and where very high reliability is required. Constant force springs, such as springs 314, provides markedly superior constant force loading when compared to conventional helical compression or like conventional types of springs. As can be seen in FIG. 43, the constant force extension spring 314 is a twin roll of a prestressed metal strip which can exert a substantially constant restraining force which resists uncoiling. As the strip is extended, the inherent stresses therein resist the loading force at a substantially constant rate. As shown in FIGS. 43, 45, 46, 47, and 47A, the strip is rotatably mounted and tightly wrapped and disposed within wells defined by elements 315 and 315*a* (see FIGS. 45 and 46). Springs 314 can be of a single laminate construction, such a shown in the drawings, where the twin roll spring acts on a pusher member 316 which is of the character shown in FIGS. 43, 44, 47 and 47*a*. Springs 314 can be constructed from a wide variety of materials including stainless steel. After the springs are extended in the manner shown in the upper left-hand portion of FIG. 43, the constant force springs will tend to uniformly return toward their starting configuration and in so doing will exert a substantially constant force on the pusher members 316 which are operably coupled with the expandable housings 42 via indicator collars 316*a*. As the springs return to their starting configuration, the fluid contained within the fluid reservoirs 44 will be caused to flow outwardly through outlet 318 at a substantially constant rate. It should be noted that in some instances the springs 314 can be preloaded. Springs 314 are mounted within snap-together sides of housing portion 158 in the manner illustrated in FIGS. 45, 46, and 47 with each spring being supported within the cavities or wells defined by elements 315 and 315*a*.

Forming an important aspect of this latest form of the apparatus of the present invention is fill means carried by portion 164 of the outer housing for filling the reservoirs 44 with the fluid to be dispensed. These fill means, which comprise fill vials 52 and 52*b*, are substantially identical in construction and operation to those previously described herein and, therefore, will not here be redescribed.

As the fluid flows into the reservoir portions of the bellows during the filling step, the bellows will be expanded from a collapsed configuration into all expanded configuration such as shown in the upper left-hand portion of FIG. 43. As the bellows members expand they will controllably extend, and continually load spring members 314 (see the upper left-hand portion of FIG. 43). As the reservoirs 44 fill with Fluid, any gases trapped within the reservoirs will be vented to atmosphere via vent means "V" mounted in the housing proximate handle 162 (FIG. 43).

Upon opening the fluid delivery path to the of the invention, shown here as comprising a conventional administration set 80 (FIG. 42), the stored energy means, or members 314, will tend to return to their starting configuration thereby controllably urging fluid flow outwardly of selected reservoirs 44 via the flow control means of the invention. Once again, in this latest form of the invention, administration set 80, which is identical and construction and operation to that previously described, comprises a part of the dispensing means of the invention for delivering medicinal fluids to the patient.

Forming another important aspect of the apparatus of this latest form of the invention is the novel flow control means that are carried proximate the central portion of housing 166. These flow control means, which are identical in construction and operation to those described in connection with the embodiment shown in FIGS. 26 through 47, function to precisely control the rate of fluid flow outwardly from the various fluid reservoirs into the administration set 80 and toward the patient. The details of construction of the flow control means are illustrated in FIGS. 31 through 38 and will not here be redescribed. Suffice to say that the flow control means comprises a plurality of flow control assemblies generally designated in the earlier described figure drawings by the numerals 192, 193 and 194. Each of these flow control assemblies comprise an inlet manifold 196 having an inlet port 198 that is in communication with a selected one of the outlets 199 of the fluid reservoirs 44*b* and 44*c* (FIG. 43) and an outlet manifold 200 that is interconnected with inlet manifold 196 by means of a plurality of interconnected flow rate control plates 202, 204, 206, 208, 210, 212, 214, 216, 218 and 220 (see particularly FIG. 37). As in the earlier described embodiments of the invention, the rate of flow of fluid flowing outwardly of each of the outlet ports of the various rate control plates will, of course, depend upon the individual parameters and configuration of the individual rate control micro channels formed in the various rate control plates.

Also forming a part of the flow control means of this latest form of the invention are identically constructed thumbwheels 288, which are selectively connected to the outlet manifolds of the apparatus flow control member and identically constructed indicator drams 290 which are securely keyed and connected to the thumbwheels. As indicated in FIG. 43, fluid connectors 292 function to interconnect via passageway 292*a* the flow passageways of the elongated needles 58 and 58*a* of the fill means of the invention with the elongated passageways 190 and 190*a* which carry the medicinal fluids to reservoirs 44*a*, 44*b* and 44*c*. In this latest form of the invention, the flow control means further includes selection., mixing and dispensing means, shown here as comprising a knob 94, which is identical in construction and operation to that previously described and that is rotatably carried with in housing portion 156 in the manner best seen in FIG. 43. As previously described, mixing and dispensing knob 94 can be manipulated by the caregiver to select the medicinal fluid or fluid mixture that is to be delivered to the patient.

It is to be understood that, as the thumbwheels 288 are rotated, the indicator drums 290 that are associated therewith will also rotate. As the drums rotate, indicia, which are imprinted in each of the drums and which indicate fluid flow rate, can be viewed through upper, intermediate and lower viewing windows 110 provided in the apparatus housing (FIGS. 1 and 43). In this way, the caregiver can precisely select the desired outward rate of fluid flow toward the administration set of the medicinal fluids contained within each of the upper, intermediate and lower fluid reservoirs.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A dispensing apparatus for dispensing fluids to a patient comprising:
    (a) an outer housing;
    (b) a plurality of inner, expandable housings disposed within said outer housing, each of said inner expandable housings having a fluid reservoir provided with an inlet for permitting fluid flow into said fluid reservoir and an outlet for permitting fluid flow from said fluid reservoir;
    (c) a plurality of stored energy means disposed within said outer housing and operably associated with said plurality of inner expandable housings for acting upon said housings to cause the fluid contained within the fluid reservoirs thereof to controllably flow through said outlets, each of said stored energy means comprising a yieldably deformable member carried within said outer housing, each of said compressively deformable members being expandable to cause fluid flow from said fluid reservoirs;

(d) at least one fill means carried by said outer housing and being in communication with said inlets of said fluid reservoirs for filling said reservoirs with the fluid to be dispensed;

(e) fluid delivery means connected to said outer housing and being in communication with said outlets of said fluid reservoirs for delivering fluids to the patient; and (f) flow control means carried by said outer housing for controlling fluid flow from said reservoirs toward said fluid delivery means, said flow control means being in communication with said outlets of said fluid reservoirs and being in communication with said fluid delivery means, said flow control means comprising:

(i) flow rate control means carried within said outer housing and being in communication with said outlets of said fluid reservoirs for controlling the rate of fluid flow toward said fluid delivery means; and (ii) flow regulating means carried within the said outer housing and being in communication with said flow rate control means for regulating the flow of fluids flowing from said flow rate control means toward said fluid delivery means.

2. The apparatus as defined in claim 1 in which said yieldably deformable members each comprise a flexible polymeric member.

3. The apparatus as defined in claim 1 in which each said yieldably definable member comprises a spring.

4. The apparatus as defined in claim 1 in which said inner expandable housing each comprise a bellows structure having an accordion like side wall movable from a substantially collapsed configuration to a substantially expanded configuration by fluid flowing into said fluid reservoir defined by said bellows structure.

5. The apparatus as defined in claim 1 in which said flow rate control means comprises a plurality of flow control members, each said flow control member having a plurality of elongated flow control channels formed therein and each being rotatable within a selected one of said inner expandable housings.

6. The apparatus as defined in claim 1 in which said flow regulating means comprises a mixing and dispensing knob rotatably carried by said outer housing, said mixing and dispensing knob having inlets in communication with said flow rate control means.

7. The apparatus as defined in claim 1 in which said fill means comprises a plurality of fill vials receivable within said outer housing.

8. The apparatus as defined in claim 7 in which said outer housing includes:

(a) a plurality of spaced apart receiving chambers for telescopically receiving said plurality of fill vials; and (b) an elongated support mounted within each of said receiving chambers, each said elongated support having an elongated hollow needle, said hollow needle defining a flow passageway in communication with a selected one of said fluid reservoirs.

9. The apparatus as defined in claim 8 in which each of said fill vials has a first open end, a closed second end and in which each includes;

(a) a fluid reservoir disposed between said first and second ends; and (b) a pierceable plunger disposed within said fluid reservoir for movement between first and second positions.

10. A dispensing apparatus for dispensing fluids to a patient comprising:

(a) an outer housing having an upper portion and a lower portion, said lower portion having a plurality of spaced apart vial receiving chambers;

(b) a plurality of inner, expandable housings disposed within said lower portion of said outer housing, each of said inner expandable housings comprising a bellows structure having an accordion like side wall defining a fluid reservoir, each said accordion like side wall being movable from a substantially collapsed configuration to a substantially expanded configuration by fluid flowing into said fluid reservoir, each said vial reservoir having an inlet for permitting fluid flow into said fluid reservoir and an outlet for permitting fluid flow from said fluid reservoir;

(c) a plurality of stored energy means disposed within said lower portion of said outer housing for acting upon said plurality of inner expandable housings to cause the fluid contained within said fluid reservoirs thereof to controllably flow through said outlets, each of said stored energy means comprising a compressively deformable, cellular member carried within said outer housing, each of said cellular members being expandable to cause fluid flow from said fluid reservoirs;

(d) a plurality of fill means carried by said lower portion of said outer housing and in communication with said inlets of said fluid reservoirs for filling said reservoirs with the fluid to be dispensed, each said fill means comprising a fill vial receivable within a selected one said vial receiving chambers of said lower portion of said outer housing;

(e) fluid delivery means in communication with said outlets of said fluid reservoirs for delivering fluids to the patient; and (f) flow control means carried by said outer housing for controlling fluid flow from said reservoirs toward said fluid delivery means, said flow control means being in communication with said outlets of said fluid reservoirs and being in communication with said fluid delivery means, said flow control means comprising:

(i) flow rate control means carried within said lower portion of said outer housing and being in communication with said outlets of said fluid reservoirs for controlling the rate of fluid flow toward said fluid delivery means, said flow rate control means comprising a plurality of flow control members, each said flow control member having a plurality of elongated flow control channels formed therein and each being rotatable within a selected one of said inner expandable housings; and (ii) flow regulating means carried within the said upper portion of said outer housing and in communication with said flow rate control means for regulating the fluids flowing from said flow rate control means toward said fluid delivery means, said flow regulating means comprising a mixing and dispensing knob rotatably carried by said upper portion of said outer housing, said mixing and dispensing knob having a plurality of inlets in communication with said flow rate control means.

11. The apparatus as defined in claim 10 further including an elongated support disposed within each of said lower receiving chambers, each said elongated support having an elongated hollow needle defining a flow passageway in communication with a selected one of said fluid reservoirs.

12. The apparatus as defined in claim 10 in which each of said fill vials has a first open end, a closed second end and in which each includes:
   (a) a fluid reservoir disposed between said first and second ends; and
   (b) a pierceable plunger disposed within said fluid reservoir for movement between first and second positions.

13. The apparatus as defined in claim 10 in which said mixing and dispensing knob has a central fluid flow passageway and a plurality of radially extending fluid flow passageways in communication with said central flow passageway, said radially extending flow passageways being in communication with said flow rate control means.

14. The apparatus as defined in claim 10 in which said flow rate control means further includes a plurality of thumbwheels rotatably carried by said lower portion of said outer housing, said thumbwheels being interconnected with said flow control members for imparting rotation thereto.

15. The apparatus as defined in claim 10 in which said flow rate control means further includes a plurality of indicator drums carried by said lower portion of said outer housing, each of said indicator drums having flow rate indicia imprinted thereon each and being interconnected with a selected one of said thumbwheels for rotation thereby.

16. The apparatus as defined in claim 10 further including knob-locking means carried by said upper portion of said outer housing for locking said mixing and dispensing knob against rotation.

17. The apparatus as defined in claim 10 further including safety disabling means carried by said upper portion of said outer housing for blocking fluid flow toward said delivery means.

18. The apparatus as defined in claim 10 in which said elongated flow control channels formed in said fluid control members are coated with a coating that is compatible with the fluids contained within the fluid reservoirs.

19. A dispensing apparatus for dispensing fluids to a patient comprising:
   (a) an outer housing having an upper portion and a lower portion, said lower portion having a plurality of spaced apart vial receiving chambers each said vial receiving chamber having an elongated support having an elongated hollow needle defining a flow passageway;
   (b) a plurality of inner, expandable housings disposed within said lower portion of said outer housing, each of said inner expandable housings comprising a bellows structure having an accordion like side wall defining a fluid reservoir, each said accordion like side wall being movable from a substantially collapsed configuration to a substantially expanded configuration by fluid flowing into said fluid reservoir each said load reservoir having an inlet for permitting fluid flow into said fluid reservoir and an outlet for permitting fluid flow from said fluid reservoir;
   (c) a plurality of stored energy means disposed within said lower portion of said outer housing for acting upon said plurality of inner expandable housing to cause the fluid contained within said fluid reservoirs thereof to controllably flow through said outlets, each of said stored energy means comprising a yieldably deformable spring that is expandable to cause fluid flow from said fluid reservoirs;
   (d) a plurality of fill means carried by said lower portion of said outer housing and in communication with said inlets of said fluid reservoirs for filling said reservoirs with the fluid to be dispensed, each said fill means comprising a fill vial receivable within a selected one said vial receiving chambers of said lower portion of said outer housing;
   (e) fluid delivery means in communication with said outlets of said fluid reservoirs for delivering fluids to the patient; and
   (f) flow control means carried by said outer housing for controlling fluid flow from said reservoirs toward said fluid delivery means, said flow control means being in communication with said outlets of said fluid reservoirs and being in communication with said fluid delivery means, said flow control means comprising flow rate control means carried within said lower portion of said outer housing and being in communication with said outlets of said fluid reservoirs for controlling the rate of fluid flow toward said fluid delivery means.

20. The apparatus as defined in claim 19 in which said flow rate control means comprises:
   (a) a plurality of flow control members, each said flow control member having a plurality of elongated flow control channels formed therein and each being rotatable within a selected one of said inner expandable housings;
   (b) a plurality of thumbwheels rotatably carried by said lower portion of said outer housing, said thumbwheels being interconnected with said flow control members for imparting rotation thereto; and
   (c) a plurality of indicator drums carried by said lower portion of said outer housing, said indicator drums having flow rate indicia imprinted thereon and being interconnected with said thumbwheels for rotation thereby.

21. The apparatus as defined in claim 19 in which said flow rate control means comprises at least one flow control plate, having a fluid flow channel formed therein.

22. The apparatus as defined in claim 19 in which said flow rate control means comprises a plurality of flow control plates each having a fluid flow microchannel formed therein.

23. The apparatus as defined in claim 19 in which said flow rate control means comprises a plurality of flow control plates each having a fluid flow capillary.

24. The apparatus as defined in claim 19 in which said fluid flow channel is coated.

25. The apparatus as defined in claim 19 further including flow regulating means carried within the said upper portion of said outer housing and in communication with said flow rate control means for regulating the fluids flowing from said flow rate control means toward said fluid delivery means, said flow regulating means comprising a mixing and dispensing knob rotatably carried within said upper portion of said outer housing, said mixing and dispensing knob having a plurality inlets in communication with said flow rate control means.

26. The apparatus as defined in claim 25 in which said mixing and dispensing knob has a central fluid flow passageway and a plurality of radially extending fluid flow passageways being in communication with said central flow passageway, said radially extending flow passageways being in communication with said flow rate control means.

27. The apparatus as defined in claim 25 in which each of said fill vials has a first open end, a closed second end and in which each includes:
   (a) a fluid reservoir disposed between said first and second ends; and
   (b) a pierceable plunger disposed within said fluid reservoir for movement between first and second positions.

28. The apparatus as defined in claim 27 in which at least one of said fill vials comprises a field fill vial.

29. The apparatus as defined in claim 27 further including safety disabling means carried by said upper portion of said outer housing for blocking fluid flow toward said delivery means.

30. The apparatus as defined in claim 27 in which said elongated flow control channels formed in said fluid control members are coated with a coating that is compatible with said fluids contained within the fluid reservoirs.

31. The apparatus as defined in claim 27 further including knob-locking means carried by said upper portion of said outer housing for locking said mixing and dispensing knob against rotation.

32. The apparatus as defined in claim 27 in which said spring member comprises a metal spring.

33. The apparatus as defined in claim 27 in which said spring member comprises a constant force extension spring.

34. The apparatus as defined in claim 27 in which said spring member comprises a wave spring.

35. The apparatus as defined in claim 27 in which said spring member comprises a plastic spring.

36. The apparatus as defined in claim 27, further including volume indicator means carried by said outer housing for indicating the volume of fluid remaining in said fluid reservoir.

37. The apparatus as defined in claim 36 in which said according-like side walls of said expandable housings are coated with a coating that is compatible with the fluids contained within said fluid reservoirs.

* * * * *